（12） United States Patent
Ushikura et al.

(10) Patent No.: US 11,624,716 B2
(45) Date of Patent: Apr. 11, 2023

(54) RADIATION DETECTOR AND RADIOGRAPHIC IMAGING DEVICE

(71) Applicant: FUJIFILM Corporation, Tokyo (JP)

(72) Inventors: Shinichi Ushikura, Kanagawa (JP); Munetaka Kato, Kanagawa (JP); Haruyasu Nakatsugawa, Kanagawa (JP); Keiichi Akamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 59 days.

(21) Appl. No.: 17/025,098

(22) Filed: Sep. 18, 2020

(65) Prior Publication Data

US 2021/0003515 A1    Jan. 7, 2021

Related U.S. Application Data

(63) Continuation of application No. PCT/JP2019/009425, filed on Mar. 8, 2019.

(30) Foreign Application Priority Data

Mar. 19, 2018   (JP) .............................. JP2018-051690
Nov. 22, 2018   (JP) .............................. JP2018-219696
Feb. 8, 2019    (JP) .............................. JP2019-022148

(51) Int. Cl.
  *G01T 1/20*   (2006.01)
  *G01N 23/04*  (2018.01)
  *G01N 23/06*  (2018.01)

(52) U.S. Cl.
  CPC ............. *G01N 23/04* (2013.01); *G01N 23/06* (2013.01); *G01T 1/2018* (2013.01);
  (Continued)

(58) Field of Classification Search
  CPC .... G01N 23/04; G01N 23/06; G01N 2223/04; G01N 2223/40; G01N 2223/505;
  (Continued)

(56) References Cited

U.S. PATENT DOCUMENTS

2002/0181659 A1    12/2002   Watanabe et al.
2004/0211911 A1*   10/2004   Hata ..................... G01T 1/2928
                                                          250/370.11
(Continued)

FOREIGN PATENT DOCUMENTS

JP    2002-082172 A    3/2002
JP    2012-047723 A    3/2012
(Continued)

OTHER PUBLICATIONS

Data sheet by Nagase "A new dimensionally stable polyimide film, XENOMAX", 1 page, downloaded from https://www.nagase.co.jp/display/english/pdf/fpd2014/toyobo.pdf (Year: 2014).*
(Continued)

*Primary Examiner* — Kiho Kim
(74) *Attorney, Agent, or Firm* — Studebaker & Brackett PC

(57) ABSTRACT

A radiation detector including: a sensor substrate including a flexible base member and a layer provided on a first surface of the base member and formed with plural pixels that accumulates electrical charge generated in response to light converted from radiation; a conversion layer provided on the first surface side of the sensor substrate, the conversion layer converts radiation into the light; and an elastic layer provided on the opposite side of the conversion layer to a side provided with the sensor substrate, the elastic layer having a greater restoring force with respect to bending than the sensor substrate.

22 Claims, 28 Drawing Sheets

(52) U.S. Cl.
CPC ..... *G01N 2223/04* (2013.01); *G01N 2223/40* (2013.01); *G01N 2223/505* (2013.01)

(58) Field of Classification Search
CPC . G01T 1/2018; G01T 1/20188; G01T 1/2023; G01T 1/208; A61B 6/00; A61B 6/4208
See application file for complete search history.

(56) References Cited

U.S. PATENT DOCUMENTS

| | | | |
|---|---|---|---|
| 2012/0219114 A1 | 8/2012 | Iwakiri et al. | |
| 2013/0019462 A1* | 1/2013 | Shoji | G01T 1/2018 29/595 |
| 2013/0154039 A1* | 6/2013 | Furui | H01L 27/14663 257/428 |
| 2014/0103216 A1 | 4/2014 | Sasaki et al. | |
| 2016/0077220 A1* | 3/2016 | Maeda | G01T 1/2012 250/484.4 |
| 2016/0202362 A1* | 7/2016 | Ichimura | G01T 1/2023 250/366 |
| 2017/0261621 A1* | 9/2017 | Nagata | G01T 1/2023 |
| 2017/0329023 A1* | 11/2017 | Homma | G01T 1/2018 |
| 2018/0017721 A1 | 1/2018 | Nagaya et al. | |
| 2018/0178492 A1* | 6/2018 | Nagao | B32B 9/041 |
| 2019/0324159 A1* | 10/2019 | Inoue | H01L 27/146 |

FOREIGN PATENT DOCUMENTS

| | | | |
|---|---|---|---|
| JP | 2012-128091 A | 7/2012 | |
| JP | 2012-189487 A | 10/2012 | |
| JP | 2013217769 A * | 10/2013 | ............... G01T 1/17 |
| JP | 2014-077735 A | 5/2014 | |
| JP | 2015-049045 A | 3/2015 | |
| TW | 201710715 A | 3/2017 | |
| WO | 2010/070735 A1 | 6/2010 | |

OTHER PUBLICATIONS

An Office Action; "Notice of Reasons for Refusal," mailed by the Japanese Patent Office dated Nov. 24, 2020, which corresponds to Japanese Patent Application No. 2020-508195 and is related to U.S. Appl. No. 17/025,098; with English language translation.

The extended European search report issued by the European Patent Office dated Mar. 23, 2021, which corresponds to European Patent Application No. 19772587.2-1001 and is related to U.S. Appl. No. 17/025,098.

An Office Action; "Notice of Reasons for Refusal," mailed by the Japanese Patent Office dated Apr. 6, 2021, which corresponds to Japanese Patent Application No. 2020-508195 and is related to U.S. Appl. No. 17/025,098; with English language translation.

International Search Report issued in PCT/JP2019/009425; dated Jun. 4, 2019.

Written Opinion issued in PCT/JP2019/009425; dated Jun. 4, 2019.

An Office Action; "Notice of Reasons for Refusal", mailed by the Japanese Patent Office dated Mar. 29, 2022, which corresponds to Japanese Patent Application No. 2021-084917 and is related to U.S. Appl. No. 17/025,098 with English language translation.

An Office Action issued by Taiwan Intellectual Property Office dated Sep. 2, 2022, which corresponds to Taiwanese Patent Application No. 108108543 and is related to U.S. Appl. No. 17/025,098; with English language translation.

* cited by examiner

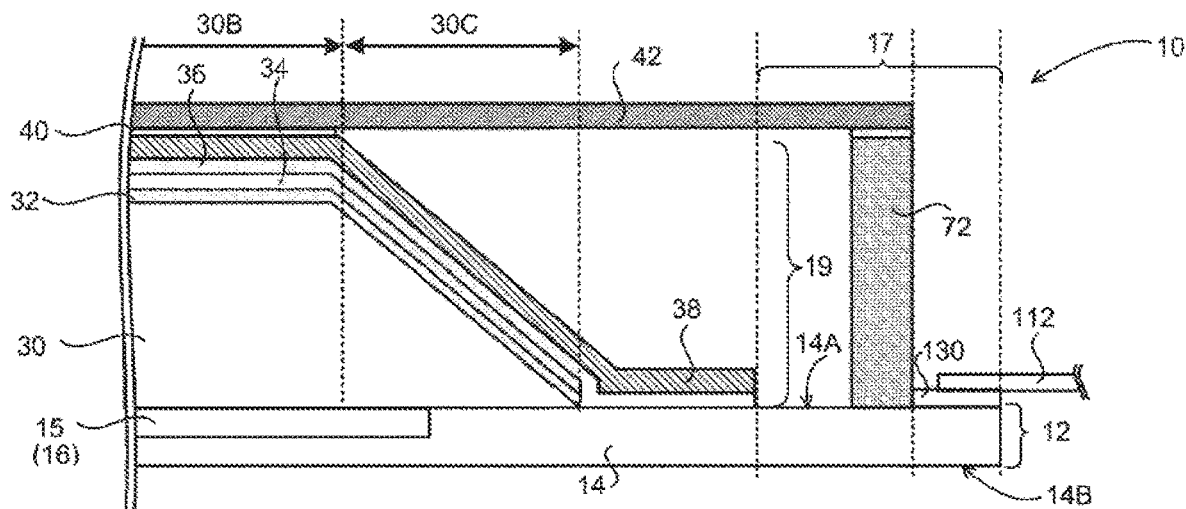
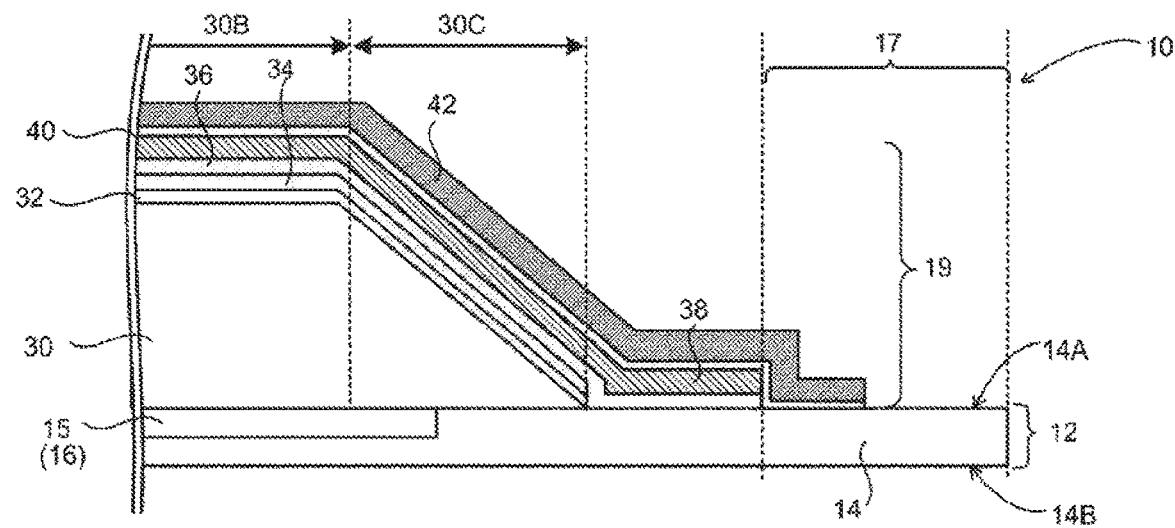

RADIATION DETECTOR AND RADIOGRAPHIC IMAGING DEVICE

CROSS-REFERENCE TO RELATED APPLICATIONS

This application is a continuation application of International Application No. PCT/JP2019/009425, filed on Mar. 8, 2019, which is incorporated herein by reference in its entirety. Further, this application claims priority from Japanese Patent Application No. 2018-051690, filed on Mar. 19, 2018, Japanese Patent Application No. 2018-219696, filed on Nov. 22, 2018, and Japanese Patent Application No. 2019-022148, filed on Feb. 8, 2019, the disclosure of which are incorporated by reference herein.

BACKGROUND

Technical Field

The present disclosure relates to a radiation detector and a radiographic imaging device.

Related Art

Radiographic imaging devices that perform radiographic imaging for medical diagnostic purposes are known. In such radiographic imaging devices, a radiation detector is employed to generate radiographic images by detecting radiation that has passed through an imaging subject.

Radiation detectors may include a conversion layer such as a scintillator to convert radiation into light, and a sensor substrate provided with plural pixels that accumulate electrical charges generated in response to light converted by the conversion layer. Some such known radiation detectors employ a flexible base member for the sensor substrate (see for example International Publication (WO) No. 2010/070735). Employing a flexible base member may for example enable a reduction in weight of the radiographic imaging device (radiation detector) or facilitate imaging of the imaging subject.

Methods referred to as coating methods and methods referred to as lamination methods are known examples of manufacturing methods for radiation detectors that employ a flexible base member for a sensor substrate. In a coating method, the flexible base member is formed by being coated onto a support body such as a glass substrate, after which the sensor substrate and the conversion layer are formed. The sensor substrate formed with the conversion layer is then separated from the support body by laser separation. In a lamination method, a sheet that is to form the flexible base member is affixed to a support body such as a glass substrate, after which the sensor substrate and the conversion layer are formed. The sensor substrate formed with the conversion layer is then separated from the support body either by mechanical separation or laser separation.

Thus, whichever out of the coating method or the lamination method is applied, the manufacturing processes include a process to separate the sensor substrate from the support body. However, the flexible base member employed as the sensor substrate sometimes bends during separation of the sensor substrate from the support body. This bending of the flexible base member might for example result in damage to pixels on the sensor substrate, or damage to the conversion layer.

SUMMARY

The present disclosure provides a radiation detector and a radiographic imaging device that may suppress the effects of bending occurring during separation of a sensor substrate from a support body during a manufacturing process of the radiation detector provided with the sensor substrate including a flexible base member manufactured using the support body, compared to configurations in which a layer that has a greater restoring force with respect to bending than the sensor substrate is not provided on the opposite side of a conversion layer to a side provided with the sensor substrate.

A first aspect of the present disclosure is a radiation detector including: a sensor substrate including a flexible base member and a layer provided on a first surface of the base member and formed with plural pixels that accumulates electrical charge generated in response to light converted from radiation; a conversion layer provided on the first surface side of the sensor substrate, the conversion layer converts radiation into the light; and an elastic layer provided on the opposite side of the conversion layer to a side provided with the sensor substrate, the elastic layer having a greater restoring force with respect to bending than the sensor substrate.

A radiation detector of a second aspect of the present disclosure is the radiation detector of the first aspect, wherein the elastic layer has a bending elastic modulus of from 150 MPa to 2500 MPa.

A radiation detector of a third aspect of the present disclosure is the radiation detector of the first aspect or the second aspect, wherein a material of the elastic layer includes at least one material out of polycarbonate, polyethylene terephthalate, or low density polyethylene.

A radiation detector of a fourth aspect of the present disclosure is the radiation detector of any one of the first aspect to the third aspect, wherein a ratio of a coefficient of thermal expansion of the elastic layer with respect to a coefficient of thermal expansion of the conversion layer is from 0.5 to 4.

A radiation detector of a fifth aspect of the present disclosure is the radiation detector of any one of the first aspect to the fourth aspect, wherein the elastic layer has a coefficient of thermal expansion of from 30 ppm/K to 200 ppm/K.

A radiation detector of a sixth aspect of the present disclosure is the radiation detector of any one of the first aspect to the fifth aspect, wherein the sensor substrate further includes a terminal portion provided at an outer peripheral portion of the first surface of the base member, the terminal portion being connected to a cable for reading electrical charge from the pixels; and an end portion of the elastic layer is positioned at an inner side of a region provided with the terminal portion.

A radiation detector of a seventh aspect of the present disclosure is the radiation detector of the sixth aspect, wherein: the conversion layer includes a peripheral edge portion having a slope that decreases in thickness on progression toward an outer side, and a central portion surrounded by the peripheral edge portion; and the elastic layer covers at least the central portion.

A radiation detector of an eighth aspect of the present disclosure is the radiation detector of the sixth aspect, wherein the conversion layer includes a peripheral edge portion having a slope that decreases in thickness on progression toward an outer side, and a central portion surrounded by the peripheral edge portion, and the elastic layer covers the central portion and at least part of the peripheral edge portion.

A radiation detector of a ninth aspect of the present disclosure is the radiation detector of the sixth aspect, wherein: the conversion layer includes a peripheral edge portion having a slope that decreases in thickness on progression toward an outer side, and a central portion surrounded by the peripheral edge portion; and an end portion of the elastic layer is provided to reach at least from a region covering the central portion to a region corresponding to an outer periphery of the peripheral edge portion.

A radiation detector of a tenth aspect of the present disclosure is the radiation detector of any one of the first aspect to the fifth aspect, wherein: the sensor substrate further includes a terminal portion provided at an outer peripheral portion of the first surface of the base member, the terminal portion being connected to a cable for reading electrical charge from the pixels; and the elastic layer is provided so as to reach a region opposing part or all of a region provided with the terminal portion.

A radiation detector of an eleventh aspect of the present disclosure is the radiation detector of any one of the first aspect to the fifth aspect, wherein the elastic layer is provided in a wider region than a region of the sensor substrate provided with the conversion layer.

A radiation detector of a twelfth aspect of the present disclosure is the radiation detector of any one of the first aspect to the fifth aspect, wherein an end portion of the elastic layer projects further toward an outer side than an end portion of the sensor substrate.

A radiation detector of a thirteenth aspect of the present disclosure is the radiation detector of any one of the first aspect to the fifth aspect, wherein the elastic layer is provided so as to reach a region outside the conversion layer, and the elastic layer further includes a support portion that supports between an end portion of the elastic layer and the sensor substrate.

A radiation detector of a fourteenth aspect of the present disclosure is the radiation detector of any one of the first aspect to the fifth aspect, further including a filler that fills a space between the sensor substrate and the elastic layer where the conversion layer is not present.

A radiation detector of a fifteenth aspect of the present disclosure is the radiation detector of the fourteenth aspect, wherein the filler contacts the sensor substrate and the elastic layer.

A radiation detector of a sixteenth aspect of the present disclosure is the radiation detector of any one of the first aspect to the fifteenth aspect, further including a cohesion layer provided between the sensor substrate and the conversion layer.

A radiation detector of a seventeenth aspect of the present disclosure is the radiation detector of any one of the first aspect to the fifteenth aspect, further including a buffer layer provided between the sensor substrate and the conversion layer, the buffer layer buffers a difference between a coefficient of thermal expansion of the conversion layer and a coefficient of thermal expansion of the sensor substrate.

A radiation detector of an eighteenth aspect of the present disclosure is the radiation detector of any one of the first aspect to the seventeenth aspect, further including an elastic member provided on a second surface side of the base member on the opposite side to the first surface, the elastic member having a greater restoring force with respect to bending than the sensor substrate.

A radiation detector of a nineteenth aspect of the present disclosure is the radiation detector of the eighteenth aspect, wherein at least part of the elastic layer and at least part of the elastic member oppose each other across the sensor substrate and the conversion layer.

A radiation detector of a twentieth aspect of the present disclosure is the radiation detector of the eighteenth aspect or the nineteenth aspect, wherein a material of the elastic member includes at least one material out of polycarbonate, polyethylene terephthalate, or low density polyethylene.

A radiation detector of a twenty-first aspect of the present disclosure is the radiation detector of any one of the eighteenth aspect to the twentieth aspect, wherein a ratio of a coefficient of thermal expansion of the elastic member with respect to a coefficient of thermal expansion of the conversion layer is from 0.5 to 4.

A radiation detector of a twenty-second aspect of the present disclosure is the radiation detector of any one of the eighteenth aspect to the twenty-first aspect, wherein the elastic member has a coefficient of thermal expansion of from 30 ppm/K to 200 ppm/K.

A radiation detector of a twenty-third aspect of the present disclosure is the radiation detector of any one of the first aspect to the twenty-second aspect, wherein the base member is made of resin and includes a fine particle layer containing inorganic fine particles having a mean particle size of from 0.05 µm to 2.5 µm.

A radiation detector of a twenty-fourth aspect of the present disclosure is the radiation detector of the twenty-third aspect, wherein the base member includes the fine particle layer provided on the second surface side.

A radiation detector of a twenty-fifth aspect of the present disclosure is the radiation detector of the twenty-third aspect or the twenty-fourth aspect, wherein the fine particles include an element having an atomic number that is greater than an atomic number of elements configuring the base member and that is an atomic number not exceeding 30.

A radiation detector of a twenty-fifth aspect of the present disclosure is the radiation detector of any one of the first aspect to the twenty-fifth aspect, wherein the base member has a coefficient of thermal expansion no greater than 20 ppm/K at 300° C. to 400° C.

A radiation detector of a twenty-seventh aspect of the present disclosure is the radiation detector of any one of the first aspect to the twenty-sixth aspect, wherein the base member satisfies at least one condition out of having a heat shrinkage ratio in a machine direction at 400° C. and at a thickness of 25 µm of no greater than 0.5%, or having a modulus of elasticity at 500° C. of no less than 1 GPa.

A radiation detector of a twenty-eighth aspect of the present disclosure is the radiation detector of any one of the first aspect to the twenty-seventh aspect, wherein the elastic layer has a higher rigidity than the base member.

A radiation detector of a twenty-ninth aspect of the present disclosure is the radiation detector of any one of the first aspect to the twenty-eighth aspect, wherein the conversion layer includes CsI.

A radiographic imaging device of a thirtieth aspect of the present disclosure includes: the radiation detector of any one of the first aspect to the twenty-ninth aspect, a control section that output a control signal in order to read the electrical charges accumulated in the plural pixels; a drive section that output a drive signal in order to read the electrical charges from the plural pixels in response to the control signal; and a signal processing section that generates and output image data in response to an input electrical signal in a case in which input with the electrical signal according to the electrical charges read from the plural pixels.

A radiographic imaging device of a thirty-first aspect of the present disclosure is the radiographic imaging device of the thirtieth aspect, wherein the control section and the radiation detector are provided arranged in a direction intersecting a stacking direction of the base member, the layer formed with the plural pixels, and the conversion layer in the radiation detector.

A radiographic imaging device of a thirty-second aspect of the present disclosure is the radiographic imaging device of the thirtieth aspect, further including a power source section supplying electric power to at least one out of the control section, the drive section, or the signal processing section, wherein the power source section, the control section, and the radiation detector are provided arranged in a direction intersecting a stacking direction of the sensor substrate, the conversion layer, and the elastic layer in the radiation detector.

A radiographic imaging device of a thirty-third aspect of the present disclosure is the radiographic imaging device of the thirtieth aspect, further including a case that includes an irradiated face for irradiation with radiation, the case houses the radiation detector in a state in which out of the sensor substrate and the conversion layer of the radiation detector it is the sensor substrate that opposes the irradiated face.

The first aspect of the present disclosure may suppress the effects of bending occurring during separation of the sensor substrate from a support body during a manufacturing process of the radiation detector provided with the sensor substrate including the flexible base member manufactured using the support body, compared to configurations in which a layer that has a greater restoring force with respect to bending than the sensor substrate is not provided on the opposite side of the conversion layer to the side provided with the sensor substrate.

The second aspect may suppress the thickness of the elastic layer required to obtain the desired rigidity, in comparison to cases in which the bending elastic modulus is less than 150 MPa or greater than 2500 MPa.

The third aspect may suppress the sensor substrate and the conversion layer to be from detaching from one another, in comparison to cases that do not include at least one material out of polycarbonate, polyethylene terephthalate, or low density polyethylene.

The fourth aspect may suppress the sensor substrate and the conversion layer from detaching from one another, than in cases in which the coefficient of thermal expansion ratio is less than 0.5 or greater than 4.

The fifth aspect may suppress the sensor substrate and the conversion layer from detaching from one another, than in cases in which this coefficient of thermal expansion is less than 30 ppm/K or greater than 200 ppm/K.

The sixth aspect of the present disclosure may more easily provide terminals at a terminal portion, than in cases in which the end portion of the elastic layer is positioned further toward the outer side than a region provided with the terminal portion.

The seventh aspect of the present disclosure may suppress the effects of bending during separation of the sensor substrate from the support body, than in cases in which the elastic layer does not cover the central portion of the conversion layer.

The eighth aspect of the present disclosure may suppress the effects of bending during separation of the sensor substrate from the support body, than in cases in which the elastic layer does not cover the central portion and at least part of the peripheral edge portion of the conversion layer.

The ninth aspect of the present disclosure may suppress the effects of bending during separation of the sensor substrate from the support body, than in cases in which the end portion of the elastic layer is not provided to reach at least from a region covering the central portion to a region corresponding to an outer periphery of the peripheral edge portion of the conversion layer.

The tenth aspect of the present disclosure may enable a high restoring force with respect to bending to be imparted further toward the end portion of the sensor substrate, than in cases in which the elastic layer is not provided in the region provided with the terminal portion.

The eleventh aspect of the present disclosure may suppress the end portion of the conversion layer from detaching from the sensor substrate, than in cases in which the elastic layer is provided in a region narrower than a region of the sensor substrate provided with the conversion layer.

The twelfth aspect of the present disclosure may enable a high restoring force with respect to bending to be imparted further toward the end portion of the sensor substrate, than in cases in which the end portion of the elastic layer is further toward the inner side than the end portion of the sensor substrate.

The thirteenth aspect of the present disclosure may enable a high restoring force with respect to bending to be imparted further toward the end portion of the sensor substrate, than in cases in which a support portion does not provide support between the end portion of the elastic layer and the sensor substrate.

The fourteenth aspect of the present disclosure may enable a high restoring force with respect to bending to be imparted further toward the end portion of the sensor substrate, than in cases in which the space between the sensor substrate and the elastic layer where the conversion layer is not present is not filled with a filler.

The fifteenth aspect of the present disclosure may stably provide the elastic layer, than in cases in which the filler does not contact the sensor substrate and the elastic layer.

The sixteenth aspect of the present disclosure may enable the conversion layer to detach from the sensor substrate less readily, than in cases in which the cohesion layer is not provided.

The seventeenth aspect of the present disclosure may suppress the sensor substrate and the conversion layer from detaching from one another, than in cases in which the buffer layer is not provided.

The eighteenth aspect of the present disclosure may suppress the effects of bending occurring in the sensor substrate, than in cases in which an elastic member having a higher restoring force with respect to bending than the sensor substrate is not provided on the second surface side of the base member.

The nineteenth aspect of the present disclosure may suppress the effects of bending occurring in the sensor substrate due to the elastic layer and the elastic member augmenting one another, in comparison to cases in which at least part of the elastic layer and at least part of the elastic member do not oppose each other across the sensor substrate and the conversion layer.

The twentieth aspect of the present disclosure may suppress the sensor substrate and the conversion layer from detaching from one another, in comparison to cases that do not include at least one material out of polycarbonate, polyethylene terephthalate, or low density polyethylene.

The twenty-first aspect of the present disclosure may suppress the sensor substrate and the conversion layer from detaching from one another, than in cases in which the coefficient of thermal expansion ratio is less than 0.5 or greater than 4.

The twenty-second aspect of the present disclosure may suppress the sensor substrate and the conversion layer detaching from one another, than in cases in which this coefficient of thermal expansion is less than 30 ppm/K or greater than 200 ppm/K.

The twenty-third aspect of the present disclosure may suppress back-scattered radiation generated within the base member, in comparison to cases in which the base member does not include the fine particle layer containing inorganic fine particles having a mean particle size of from 0.05 μm to 2.5 μm.

The twenty-fourth aspect of the present disclosure may form the pixels with better precision, than in cases in which the base member includes the fine particle layer on the first surface side.

The twenty-fifth aspect of the present disclosure may effectively suppress back-scattered radiation and may suppress absorption of radiation in the fine particle layer, than in cases in which the fine particles do not include an element having an atomic number that is greater than an atomic number of the elements configuring the base member and that is an atomic number not exceeding 30.

The twenty-sixth aspect of the present disclosure may enable the base member to be better suited to manufacture of the pixels, than in cases in which the base member has a coefficient of thermal expansion greater than 20 ppm/K at 300° C. to 400° C.

The twenty-seventh aspect of the present disclosure may enable the base member to be better suited to manufacture of the pixels, than in cases in which the base member has a heat shrinkage ratio in a machine direction at 400° C. and at a thickness of 25 μm of greater than 0.5%, or has a modulus of elasticity at 500° C. of less than 1 GPa.

The twenty-eighth aspect of the present disclosure may suppress bending of the base member, than in cases in which the rigidity of the elastic layer is no higher than the rigidity of the base member.

The twenty-ninth aspect of the present disclosure may enhance the efficiency of radiation to visible light conversion, in comparison to cases in which the conversion layer does not include CsI.

The thirtieth aspect of the present disclosure may suppress the sensor substrate and the conversion layer from detaching from one another, than in cases in which a radiation detector that is different to the radiation detector of any one of the first aspect to the twenty-ninth aspect is provided.

The thirty-first aspect of the present disclosure may suppress the sensor substrate and the conversion layer from detaching from one another even in cases in which the control section and the radiation detector are provided arranged in a direction intersecting the stacking direction of the base member, the layer formed with the plural pixels, and the conversion layer in the radiation detector, than in cases in which a radiation detector that is different to the radiation detector of any one of the first aspect to the twenty-ninth aspect is provided.

The thirty-second aspect of the present disclosure may suppress the sensor substrate and the conversion layer from detaching from one another, even in cases in which the power source section, the control section, and the radiation detector are provided arranged in a direction intersecting the stacking direction of the sensor substrate, the conversion layer, and the elastic layer in the radiation detector, than in cases in which a radiation detector that is different to the radiation detector of any one of the first aspect to the twenty-ninth aspect is provided.

The thirty-third aspect of the present disclosure may enhance the image quality of radiographic images, in comparison to cases in which the case houses the radiation detector in a state in which the irradiated face and the conversion layer oppose each other.

BRIEF DESCRIPTION OF DRAWINGS

FIG. 22 is a cross-sectional view illustrating an example of configuration of a radiation detector of an exemplary embodiment of technology disclosed herein.

FIG. 23 is a cross-sectional view illustrating an example of configuration of a radiation detector of an exemplary embodiment of technology disclosed herein.

DESCRIPTION OF EMBODIMENTS

Detailed explanation follows regarding exemplary embodiments of the present invention, with reference to the drawings. Note that the present invention is not limited by these exemplary embodiments.

First Exemplary Embodiment

A radiographic imaging device of the present exemplary embodiment has a function of capturing radiographic images of an imaging target by detecting radiation that has passed through an imaging subject configuring the imaging target, and outputting image information expressing a radiographic image of the imaging subject.

Figure 1:
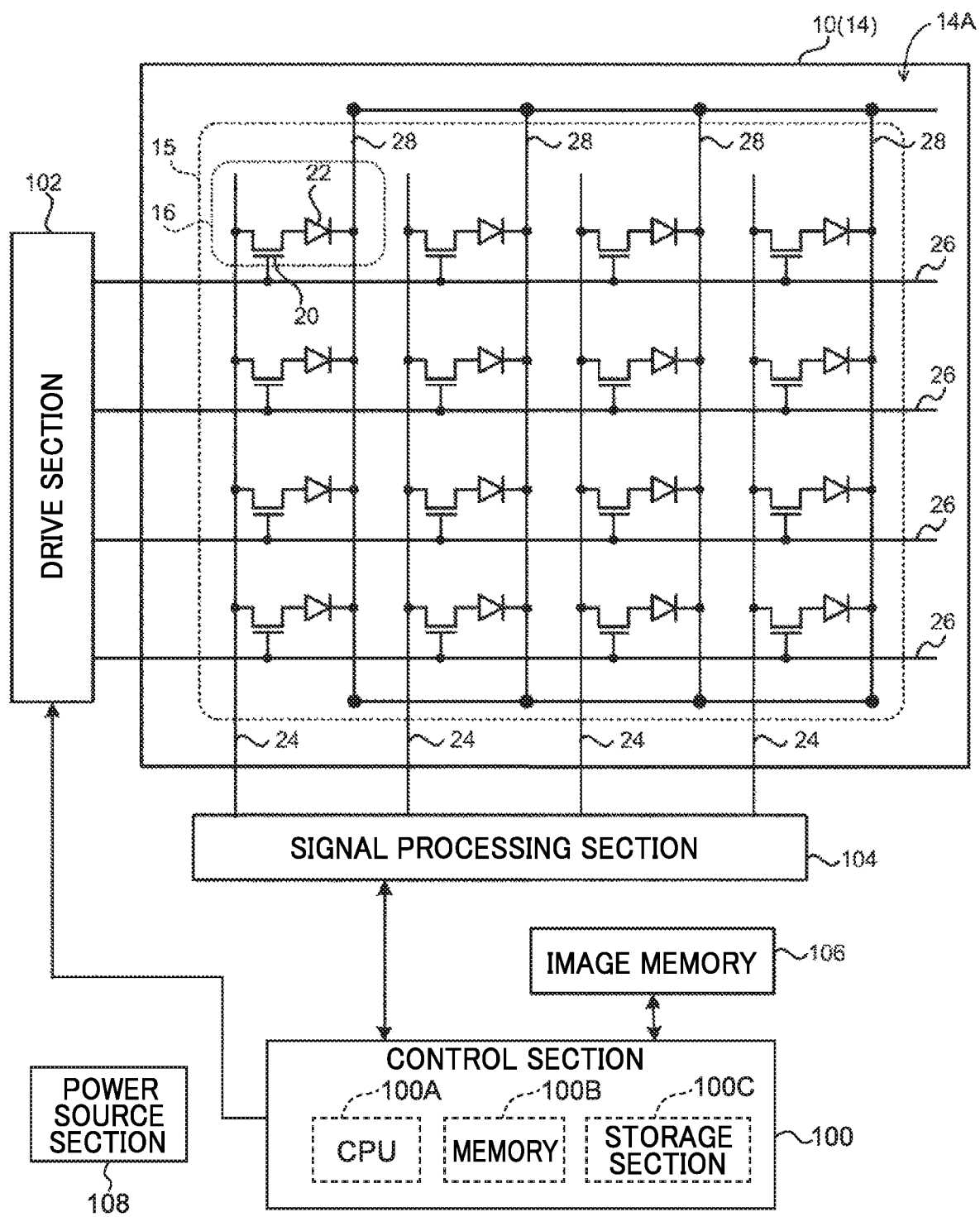
FIG. 1 is a block diagram illustrating an example of relevant configuration of an electrical system of a radiographic imaging device of a first exemplary embodiment.

First, basic explanation follows regarding an example of configuration of an electrical system of the radiographic imaging device of the present exemplary embodiment, with reference to FIG. 1. FIG. 1 is a block diagram illustrating an example of relevant configuration of the electrical system of the radiographic imaging device of the present exemplary embodiment.

As illustrated in FIG. 1, a radiographic imaging device 1 of the present exemplary embodiment includes a radiation detector 10, a control section 100, a drive section 102, a signal processing section 104, an image memory 106, and a power source section 108.

The radiation detector 10 includes a sensor substrate 12 (see FIG. 3) and a conversion layer 30 (see FIG. 3) to convert radiation into light. The sensor substrate 12 includes a flexible base member 14 and plural pixels 16 provided on a first surface 14A of the base member 14. In the following explanation, the plural pixels 16 are also referred to simply as the "pixels 16".

As illustrated in FIG. 1, each of the pixels 16 of the present exemplary embodiment includes a sensor section 22 that accumulates an electrical charge generated in response to light converted by the conversion layer, and a switching element 20 that reads the accumulated electrical charge from the sensor section 22. As an example, in the present exemplary embodiment, a thin film transistor (TFT) is employed as the switching element 20. The switching element 20 is thus referred to as the "TFT 20" hereafter. In the present exemplary embodiment, a layer in which the pixels 16 are formed is provided on the first surface 14A of the base member 14 as a flattened layer formed with the sensor sections 22 and the TFTs 20. Hereafter, the layer in which the pixels 16 are formed is sometimes referred to as the pixels 16 in the interests of simplicity.

The pixels 16 are arranged along one direction (a scan line direction corresponding to the lateral direction in FIG. 1, hereafter also referred to as the "row direction") and along a direction intersecting the row direction (a signal line direction corresponding to the longitudinal direction in FIG. 1, hereafter also referred to as the "column direction") to form a two-dimensional pattern in a pixel region 15 of the sensor substrate 12. Although the array of the pixels 16 is simplified in the illustration of FIG. 1, for example 1024× 1024 of the pixels 16 are arranged along the row direction and the column direction.

The radiation detector 10 is further provided with plural scan lines 26 corresponding to each row of the pixels 16 to control switching states (ON and OFF states) of the TFTs 20, and plural signal lines 24 that intersect the plural scan lines 26 and correspond to each column of the pixels 16 to read the accumulated electrical charges from the sensor sections 22. Each of the plural scan lines 26 is connected to the drive section 102 through a pad (see pad 130 in FIG. 6A, etc.). The control section 100, described later, is connected to the drive section 102 that outputs drive signals in response to control signals output from the control section 100. In the plural scan lines 26, drive signals output from the drive section 102 to drive the TFTs 20 so as to control the switching states thereof flow through each of the plural scan lines. Each of the plural signal lines 24 is connected to the signal processing section 104 through a pad (see pad 130 in FIG. 6A, etc.) so as to output electrical charges read from the respective pixels 16 to the signal processing section 104 as electrical signals. The signal processing section 104 generates and outputs image data in response to the input electrical signals.

The control section 100, described later, is connected to the signal processing section 104, and the image data output from the signal processing section 104 is sequentially output to the control section 100. The image memory 106 is connected to the control section 100, and the image data sequentially output from the signal processing section 104 is sequentially stored in the image memory 106 under the control of the control section 100. The image memory 106 has a storage capacity capable of storing image data for a predetermined number of images, and each time radiographic imaging is performed, the image data obtained by this imaging is sequentially stored in the image memory 106.

The control section 100 includes a central processing unit (CPU) 100A, memory 100B including read only memory (ROM) and random access memory (RAM), and a non-volatile storage section 100C configured by flash memory or the like. For example, a microcomputer may be applied as the control section 100. The control section 100 controls overall operation of the radiographic imaging device 1.

Common lines 28 are provided along the wiring direction of the signal lines 24 to the sensor sections 22 of the corresponding pixels 16 in order to apply a bias voltage to the corresponding pixels 16. Each of the common lines 28 is connected to a bias power source (not illustrated in the drawings) external to the sensor substrate 12 through a pad (see pad 130 in FIG. 6A, etc.), such that the bias voltage from the bias power source is applied to the corresponding pixels 16.

The power source section 108 supplies electric power to the respective elements and respective circuitry of the control section 100, the drive section 102, the signal processing section 104, the image memory 106, and so on. Note that in FIG. 3, lines connecting the power source section 108 to the respective elements and respective circuitry are omitted from illustration in the interests of avoiding complexity.

Figure 2A:
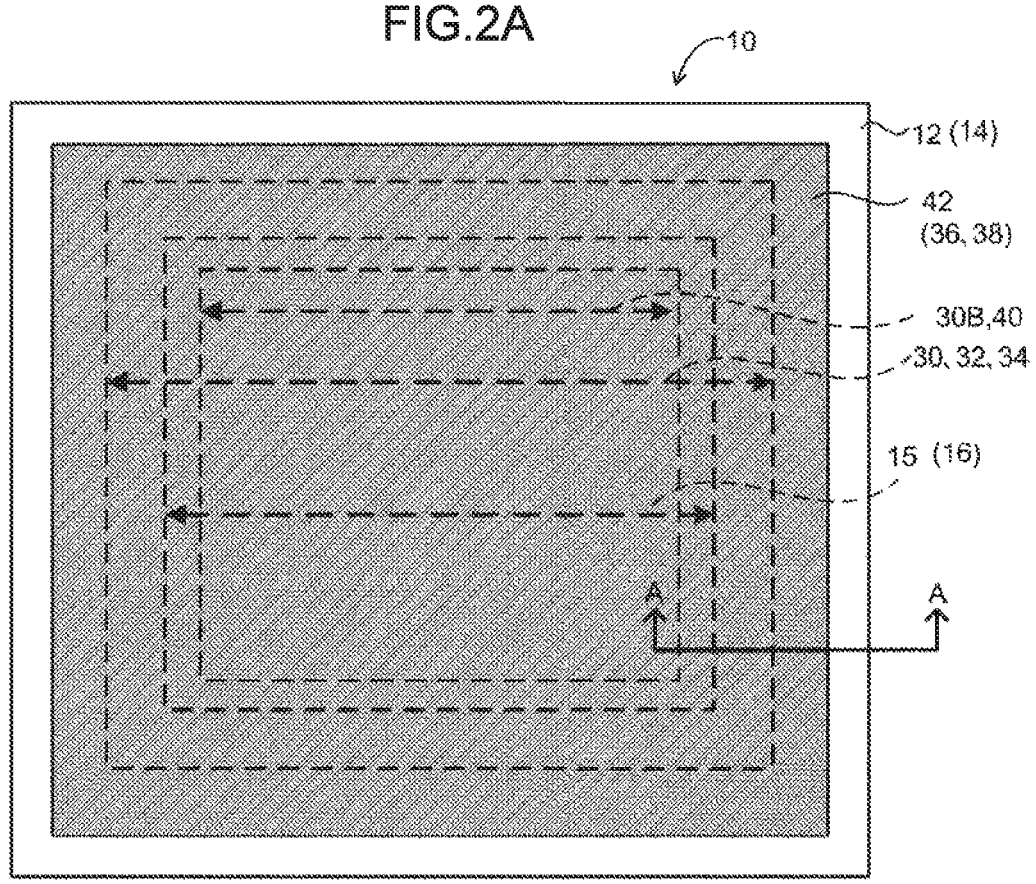
FIG. 2A is a plan view illustrating an example of a radiation detector of the first exemplary embodiment as viewed from a first surface side.
Figure 3:
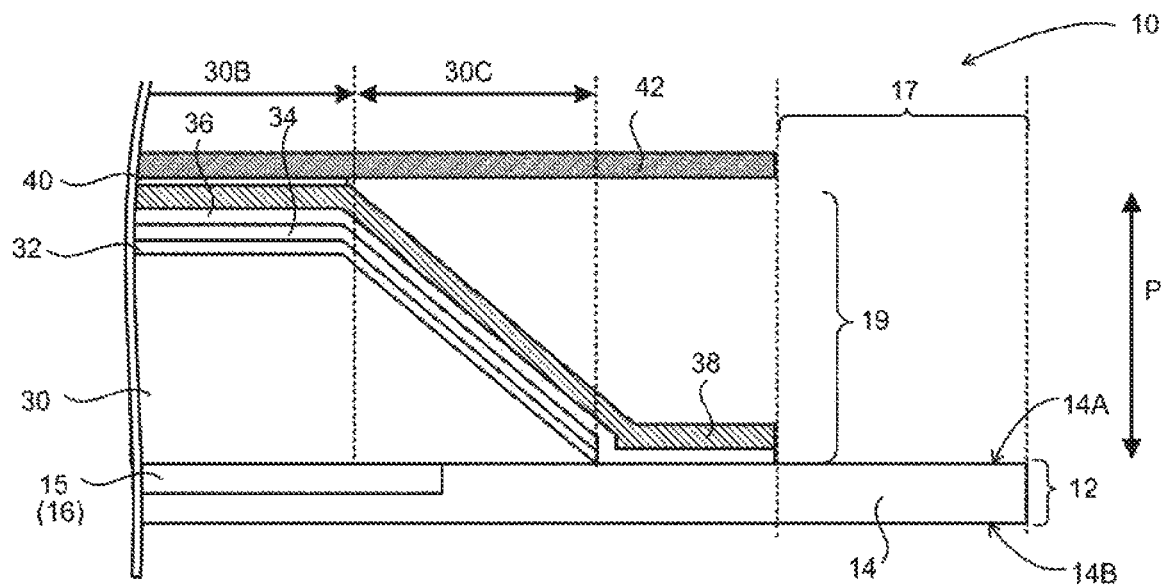
FIG. 3 is a cross-sectional view of the radiation detector illustrated in FIG. 2A as sectioned along line A-A.

Detailed explanation follows regarding the radiation detector 10 of the present exemplary embodiment. FIG. 2A is a plan view illustrating the radiation detector 10 of the present exemplary embodiment from the first surface 14A side. FIG. 3 is a cross-sectional view illustrating the radiation detector 10 as sectioned along line A-A in FIG. 2A.

As illustrated in FIG. 2A and FIG. 3, the radiation detector 10 of the present exemplary embodiment includes the sensor substrate 12 incorporating the base member 14 and the pixels 16, the conversion layer 30, an adhesion layer 32, a reflective layer 34, a bonding layer 36, a protective layer 38, a bonding layer 40, and an elastic layer 42. The base member 14, the pixels 16, and the conversion layer 30 are provided in this sequence. Note that in the following explanation, the direction in which the base member 14, the pixels 16, and the conversion layer 30 are arranged (the up-down direction in FIG. 3) is referred to as the stacking direction (the stacking direction is labeled P; see FIG. 3). For ease of explanation, the side corresponding to the conversion layer 30 in the stacking direction P of the radiation detector 10 is also referred to as the upper side, and the side corresponding to the sensor substrate 12 is also referred to as the lower side.

The base member 14 is flexible, and is for example configured by a resin sheet containing plastic such as polyimide (PI). The thickness of the base member 14 may be any thickness that enables the desired flexibility to be obtained, set according to the hardness of the material and the size of the sensor substrate 12 (the area of the first surface 14A or a second surface 14B) etc. For example, in a state in which the rectangular base member 14 is taken on its own and one edge of the base member 14 is fixed, having flexibility means that the base member 14 will droop (drop to a lower height than the fixed edge) due to gravity by at least 2 mm under the weight of the base member 14 itself at a position 10 cm from the fixed edge. As a specific example, a resin sheet configuring the base member 14 preferably has a thickness of from 5 μm to 125 μm, and more preferably has a thickness of from 20 μm to 50 μm.

Note that the base member 14 has characteristics capable of withstanding manufacture of the pixels 16, as will be described in detail later, and in the present exemplary embodiment, has characteristics capable of withstanding the manufacture of amorphous silicon TFTs (a-Si TFTs). Preferable characteristics of the base member 14 are a coefficient of thermal expansion (CTE) in a range of from 300° C. to 400° C. that is similar to that of an amorphous silicon (Si)

wafer (for example±5 ppm/K), and more specifically preferably no greater than 20 ppm/K. The heat shrinkage ratio of the base member 14 in a machine direction at 400° C. and at a thickness of 25 µm is preferably a heat shrinkage ratio of no greater than 0.5%. Moreover, the modulus of elasticity of the base member 14 preferably does not have a transition point in a temperature region of from 300° C. to 400° C., as is typical of an ordinary polyimide, and preferably has a modulus of elasticity at 500° C. of no less than 1 GPa.

Figure 2B:
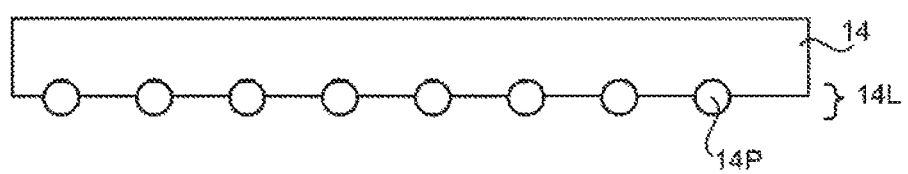
FIG. 2B is a cross-sectional view to explain an example of a base member.
Figure 2C:
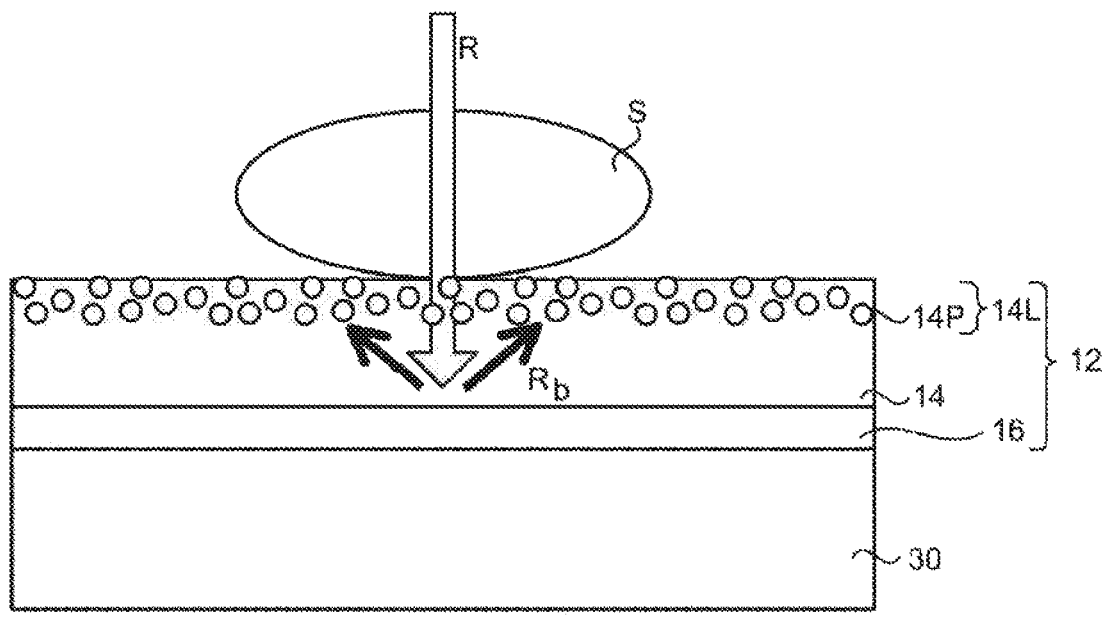
FIG. 2C is an explanatory diagram to explain back-scattered radiation generated within a base member including a fine particle layer by radiation that has passed through an imaging subject.

Moreover, as illustrated in FIG. 2B and FIG. 2C, the base member 14 of the present exemplary embodiment preferably includes a fine particle layer 14L containing inorganic fine particles 14P having a mean particle size of from 0.05 µm to 2.5 µm. Note that FIG. 2C illustrates an example of a case in which the radiation detector 10 of the present exemplary embodiment is applied as a radiation detector employing an irradiation side sampling (ISS) approach in which radiation R is irradiated from the sensor substrate 12 side.

Figure 2D:
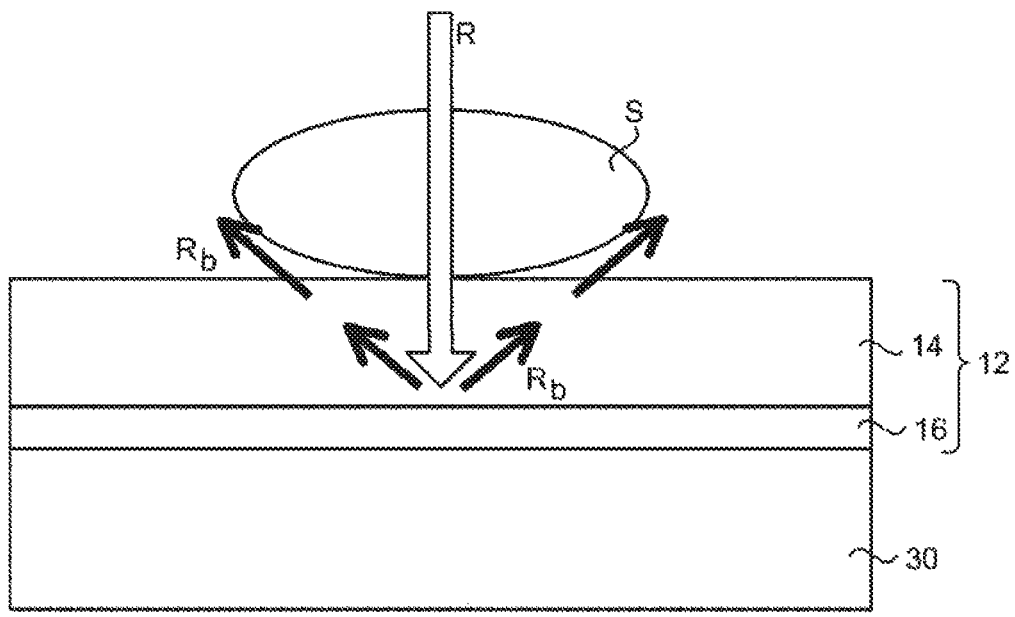
FIG. 2D is an explanatory diagram to explain back-scattered radiation generated within a base member not including a fine particle layer by radiation that has passed through an imaging subject.

As illustrated in FIG. 2C and FIG. 2D, the radiation R that has passed through an imaging subject S causes back-scattered radiation Rb in the base member 14. In cases in which the base member 14 is configured from a resin such as a PI, this being an organic material, the back-scattered radiation Rb of atoms of C, H, O, N and the like configuring the organic material and that have comparatively small atomic numbers increases due to the Compton effect.

As illustrated in FIG. 2C, in cases in which the base member 14 includes the fine particle layer 14L containing the fine particles 14P to absorb the back-scattered radiation Rb generated within the base member 14, then the back-scattered radiation Rb that has passed through the base member 14 and been scattered at the back of the base member 14 is suppressed in comparison to cases in which the base member 14 does not include the fine particle layer 14L as illustrated in FIG. 2D. The inclusion of the fine particle layer 14L is thus preferable.

The fine particles 14P are preferably configured by an inorganic material containing atoms that cause little back-scattered radiation Rb in their own right, that absorb the back-scattered radiation Rb, and that absorb little of the radiation R that has passed through the imaging subject S. Note that there is a trade-off relationship between suppressing back-scattered radiation Rb and allowing the radiation R to pass through. From the perspective of suppressing the back-scattered radiation Rb, the fine particles 14P preferably include elements having atomic numbers greater than those of the C, H, O, N, and the like configuring the resin of the base member 14. Although the ability to absorb the back-scattered radiation Rb increases the greater the atomic number, if the atomic number exceeds 30, the amount of radiation R absorbed increases, and there is a marked decrease in the amount of radiation R that reaches the conversion layer 30, and so this is not preferable. Accordingly, in cases in which the base member 14 is made of resin, an inorganic material that has an atomic number greater than the atoms configuring the organic material that is the base member 14, but does not exceed 30, is preferably employed as the fine particles 14P. Specific examples of such fine particles 14P include $SiO_2$ that is an oxide of silicon having the atomic number 14, MgO that is an oxide of Mg having the atomic number 12, $Al_2O_3$ that is an oxide of Al having the atomic number 13, and $TiO_2$ that is an oxide of Ti having the atomic number 22.

XENOMAX (registered trademark) is a specific example of a resin sheet having the characteristics listed above.

Note that in the present exemplary embodiment, the thickness is measured using a micrometer. The coefficient of thermal expansion is measured according to JIS K7197: 1991. In this measurement, test pieces are cut from a main face of the base member 14 while changing the angle thereof by 15 degrees each time, the coefficient of thermal expansion is measured for each of the cut test pieces, and the highest value obtained is taken to be the coefficient of thermal expansion of the base member 14. The measurements of the coefficient of thermal expansion in the machine direction (MD) and a transverse direction (TD) are performed at 10° C. intervals over a range of from −50° C. to 450° C. with ppm/° C. converted into ppm/K. A TMA4000S instrument made by MAC Science Co., Ltd. is employed to measure the coefficient of thermal expansion using a sample length of 10 mm, a sample width of 2 mm, an initial load of 34.5 $g/mm^2$, a rate of temperature increase of 5° C./min, and an argon atmosphere. The modulus of elasticity is measured according to JIS K7171:2016. Note that in this measurement, test pieces are cut from a main face of the base member 14 while changing the angle thereof by 15 degrees each time, a stretch test is performed on each of the cut test pieces, and the highest value obtained is taken to be the modulus of elasticity of the base member 14.

Note that unevenness may arise on the front surface of the base member 14 due to the fine particles 14P contained in the fine particle layer 14L. Formation of the pixels 16 sometimes becomes difficult in a state in which such unevenness has arisen on the front surface of the base member 14. Accordingly, as illustrated in FIG. 2C, the fine particle layer 14L is preferably included on the second surface 14B on the opposite side of the base member 14 to the first surface on which the pixels 16 are formed, namely on the second surface 14B on the opposite side to the first surface provided with the conversion layer 30.

In order to sufficiently absorb the back-scattered radiation Rb generated within the base member 14, the fine particle layer 14L is preferably included on the side of the surface of the base member 14 that is closer to the imaging subject S. As illustrated in FIG. 2C, in the ISS-approach radiation detector 10, the fine particle layer 14L is preferably included on the second surface 14B.

Thus, in the ISS-approach radiation detector 10, the base member 14 includes the fine particle layer 14L on the second surface 14B, enabling the pixels 16 to be formed with good precision, and also enabling back-scattered radiation Rb to be effectively suppressed.

Note that there is no limitation to manufacturing the base member 14 from a resin object such as a resin sheet in order to achieve the desired flexibility. For example, the base member 14 may be a glass substrate with a comparatively thin thickness. As a specific example of a case in which the base member 14 is a glass substrate, for a size having an edge length in the region of 43 cm, a glass substrate will generally be flexible at a thickness of no greater than 0.3 mm. Accordingly, a glass substrate may be employed as desired as long as the thickness is no greater than 0.3 mm.

As illustrated in FIG. 2A and FIG. 3, the plural pixels 16 are provided in a region corresponding to a portion at an inner side of the first surface 14A of the base member 14. In other words, in the sensor substrate 12 of the present exemplary embodiment, the pixels 16 are not provided at an outer peripheral portion of the first surface 14A of the base member 14. In the present exemplary embodiment, the region of the first surface 14A of the base member 14 provided with the pixels 16 is referred to as the pixel region 15. Note that in the present exemplary embodiment, an "outer peripheral portion" of the sensor substrate 12 refers to a region in a predetermined range spanning from an outer edge (an edge of the sensor substrate 12) toward the center of the first surface 14A (or the second surface 14B) of the sensor substrate 12. In the present exemplary embodiment, this region is at least outside a region provided with the conversion layer 30. An inner peripheral portion that is surrounded by the outer peripheral portion of the sensor substrate 12 includes at least the entirety of the pixel region 15.

In the sensor substrate 12 of the present exemplary embodiment, a region in a predetermined range spanning from an outer edge portion toward the center configures a pad area 17. The pad area 17 is a region provided with the pads (see pad 130 in FIG. 6A, etc.) that are connected to the various flexible cables (see cable 112 in FIG. 6A, etc.) of the plural scan lines 26, the plural signal lines 24, the common lines 28 previously described, and a control board 110 described later (see FIG. 6A, etc.). The pad area 17 of the present exemplary embodiment is an example of a terminal portion of the present disclosure. Note that the drive section 102 to which the scan lines 26 are connected, a circuit board such as a signal processing section to which the signal lines 24 are connected, and the control board 110 are collectively referred to as printed circuit boards (PCB).

As illustrated in FIG. 2 and FIG. 3, the conversion layer 30 of the present exemplary embodiment is provided in a region configuring part of the sensor substrate 12 that includes the pixel region 15. Thus, the conversion layer 30 of the present exemplary embodiment is not provided in a region corresponding to the outer peripheral portion of the sensor substrate 12.

In the present exemplary embodiment, a scintillator containing cesium iodide (CsI) is employed as an example of the conversion layer 30. For example, the scintillator preferably contains thallium-doped cesium iodide (CsI:Tl) or sodium-doped cesium iodide (CsI:Na) that has light emission spectra of from 400 nm to 700 nm when irradiated with X-rays. Note that the peak light emission wavelength of CsI:Tl in the visible light region is 565 nm.

In the radiation detector 10 of the present exemplary embodiment, as an example, the conversion layer 30 is formed from strip shaped columnar crystals formed directly to the sensor substrate 12 using a vapor phase deposition method such as a vacuum deposition method, a sputtering method, or a chemical vapor deposition (CVD) method. As an example of the formation method of the conversion layer 30, in cases in which CsI:Tl is used as the conversion layer 30, a vacuum deposition method may be applied in which the CsI:Tl is heated and vaporized, for example using a resistance heating crucible under environmental conditions of a vacuum of from 0.01 Pa to 10 Pa, and the CsI:Tl is deposited on the sensor substrate 12 with the sensor substrate 12 at a temperature between room temperature (20° C.) and 300° C. The thickness of the conversion layer 30 is preferably from 100 μm to 800 μm.

In the columnar crystals of the present exemplary embodiment, end portions on a growth direction base side of the columnar crystals of the conversion layer 30 (on the sensor substrate 12 side in the present exemplary embodiment) are referred to as the base, and peaked end portions on the opposite side to the base in the growth direction are referred to as the tips.

Figure 4:
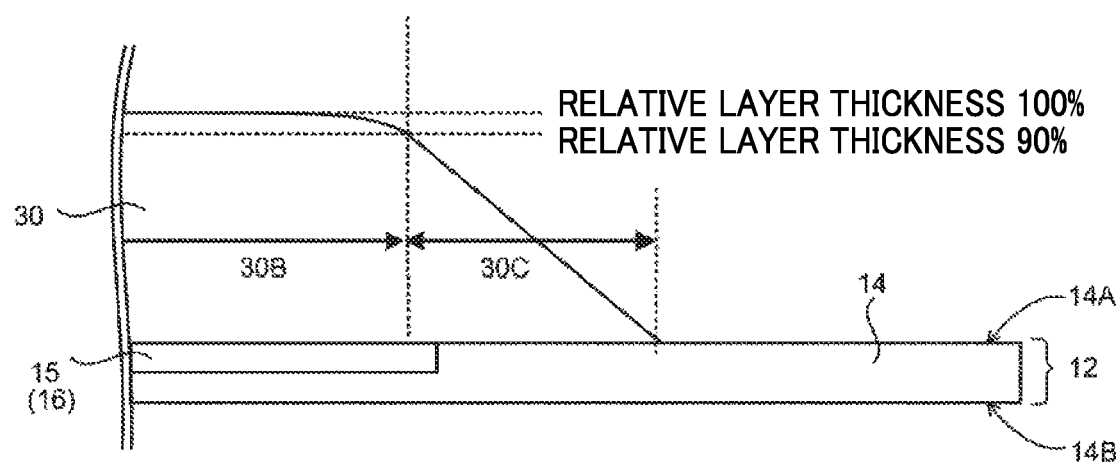
FIG. 4 is a cross-sectional view to explain a peripheral edge portion and a central portion of a conversion layer of the first exemplary embodiment.

Due to forming the conversion layer 30 of the present exemplary embodiment by a vapor phase deposition method as described above, as illustrated in FIG. 3, the region at the outer periphery of the conversion layer 30 tends to decrease in thickness on progression toward the outside when viewed as a whole, and thereby takes the form of a slope with decreasing thickness on progression toward the outside. In the present exemplary embodiment, an average value of the thickness of the conversion layer 30 within a predetermined range from the center of the conversion layer 30, where the thickness may be regarded as substantially constant if manufacturing error and measurement error are ignored, is taken as a reference. As illustrated in the example in FIG. 4, an outer peripheral region of the conversion layer 30 with a layer thickness of no greater than 90% relative to the reference thickness (hereafter referred to as relative layer thickness) is referred to as a peripheral edge portion (peripheral edge portion 30C). As illustrated in FIG. 4, a region of the conversion layer 30 surrounded by the peripheral edge portion 30C is referred to as a central portion (central portion 30B). In other words, the central portion refers to a region that includes at least a portion of the conversion layer 30 where the thickness is substantially constant, and also includes a portion where the relative layer thickness exceeds 90%. In the present exemplary embodiment as a specific example, an outer peripheral region in a region within 5 mm from the outer periphery of the conversion layer 30 and that has a relative layer thickness of no greater than 90% is referred to as the peripheral edge portion (peripheral edge portion 30C). Thus, as illustrated in FIG. 3, FIG. 4, and so on, the peripheral edge portion 30C of the conversion layer 30 tends to gradually decrease in thickness on progression toward the outer periphery (edge).

Note that although an example in which the outer periphery has a constant slope and gradually decreases in thickness has been given as an example of the thickness of the conversion layer 30 decreasing on progression toward its outer periphery in the present exemplary embodiment, there is no limitation to this configuration. For example, a configuration may be applied in which the thickness changes with a stepped profile.

Regarding the adhesion layer 32, as illustrated in the example in FIG. 2 and FIG. 3, in the radiation detector 10 of the present exemplary embodiment the adhesion layer 32 and the reflective layer 34 are provided over the entire region of the conversion layer 30, including both the central portion (30B) and the peripheral edge portion (30C) thereof. In other words, the adhesion layer 32 and the reflective layer 34 of the present exemplary embodiment cover the entire upper face of the conversion layer 30. Conversely, the adhesion layer 32 and the reflective layer 34 of the present exemplary embodiment are not provided directly above the sensor substrate 12.

The adhesion layer 32 of the present exemplary embodiment is a layer that has light-transmitting characteristics. Examples of materials that may be employed for the adhesion layer 32 include acrylic-based adhesives, hot-melt-based adhesives, silicone-based bonding agents, and the like. Examples of acrylic-based adhesives include, for example, urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), copolymers of ethylene/methyl methacrylate (EMMA), and the like.

As the thickness of the adhesion layer 32 increases, namely the greater the distance between the conversion layer 30 and the reflective layer 34, more of the light converted by the conversion layer 30 is diffused inside the adhesion layer 32, and so as a result radiographic images obtained using the radiation detector 10 are blurred images. Thus, the greater the thickness of the adhesion layer 32, the greater the reduction in modulation transfer function (MTF) and detective quantum efficiency (DQE), and the greater the severity of this reduction.

However, in cases in which the adhesion layer 32 is too thin, also encompassing cases in which the adhesion layer 32 is not provided, a very thin layer of air (not illustrated in the drawings) might be formed between the conversion layer 30 and the reflective layer 34. If this were to occur, light traveling from the conversion layer 30 toward the reflective layer 34 would be reflected repeatedly between the air layer and the conversion layer 30, and between the air layer and the reflective layer 34. Attenuation of the light due to this repeated reflection would reduce the sensitivity of the radiation detector 10. If the thickness of the adhesion layer 32 exceeds 7 µm, the severity of the reduction in DQE becomes greater than that in cases in which the adhesion layer 32 is not provided (cases in which the thickness is 0 µm), causing a reduction in the DQE. If the thickness of the adhesion layer 32 is less than 2 µm, the sensitivity of the radiation detector 10 is reduced. Thus, in the present exemplary embodiment, the thickness of the adhesion layer 32 is from 2 µm to 7 µm. Although this will differ depending on the material used, the refractive index of the adhesion layer 32 is in the region of 1.5.

Note that the adhesion layer 32 has a function of fixing the reflective layer 34 to the conversion layer 30. As long as the thickness of the adhesion layer 32 is 2 µm or greater, a sufficient advantageous effect of suppressing the reflective layer 34 from slipping with respect to the conversion layer 30 in an in-plane direction (a direction intersecting the thickness direction) is obtained.

As illustrated in the example in FIG. 2 and FIG. 3, the reflective layer 34 is provided above the adhesion layer 32, and covers the entire upper face of the adhesion layer 32. The reflective layer 34 has a function of reflecting light converted by the conversion layer 30.

An organic material is preferably employed as the material of the reflective layer 34, and for example a material employing at least one material out of white PET (polyethylene terephthalate), $TiO_2$, $Al_2O_3$, foamed white PET, a highly reflective polyester sheet, or a specular reflective aluminum is preferably employed. In particular, from the perspective of reflectivity, a white PET material is preferably employed.

Note that white PET is PET to which a white pigment, such as $TiO_2$, barium sulfate, or the like, has been added. A highly reflective polyester sheet is a sheet (film) having a multi-layered structure of plural overlapping thin polyester sheets. A foamed white PET is a white PET with a porous surface.

In the present exemplary embodiment, the thickness of the reflective layer 34 is from 10 µm to 40 µm. If the reflective layer 34 is too thick, a step formed between an upper face of an outer peripheral portion of the reflective layer 34 and an upper face of the conversion layer 30 increases in size. In the present exemplary embodiment, the radiation detector 10 is manufactured by affixing sheets (films) configuring the bonding layer 36 and the protective layer 38 to the sensor substrate 12 in a state in which the layers up to the reflective layer 34 have been formed on the sensor substrate 12. When the above-described step is large, at least one out of the bonding layer 36 or the protective layer 38 might lift up at the step portion when the bonding layer 36 and the protective layer 38 are affixed to the reflective layer 34.

If the reflective layer 34 is too thick, the reflective layer 34 becomes stiff, and it might be difficult to manipulate and bend the reflective layer 34 so as to follow the slope of the peripheral edge portion 30C of the conversion layer 30.

Considering the above points, in cases in which white PET is employed as the material of the reflective layer 34 in the radiation detector 10 of the present exemplary embodiment, the thickness of the reflective layer 34 is set to no greater than 40 µm as described above.

However, reflectivity decreases the thinner the reflective layer 34. The image quality of radiographic images obtained using the radiation detector 10 tends to drop when the reflectivity is reduced. Thus, from the perspective of the image quality of radiographic images obtained using the radiation detector 10, a lower limit for the thickness of the reflective layer 34 is preferably set in consideration of a desired reflectivity (such as 80%). Thus, in the radiation detector 10 of the present exemplary embodiment, in cases in which white PET is employed as the material of the reflective layer 34, the thickness of the reflective layer 34 is set to no less than 10 µm as described above.

As illustrated in the example in FIG. 2 and FIG. 3, the bonding layer 36 is provided from a region of the sensor substrate 12 near to the outer peripheral portion of the conversion layer 30 to a region covering an end portion of the reflective layer 34. In other words, in the radiation detector 10 of the present exemplary embodiment, the bonding layer 36 that covers the entirety of the conversion layer 30 provided with the adhesion layer 32 and the reflective layer 34 is directly fixed (bonded) to a region of the surface of the sensor substrate 12 not including the pad area 17. The bonding layer 36 has a function of fixing the reflective layer 34 to the sensor substrate 12 and the conversion layer 30. The bonding layer 36 also has a function of fixing the protective layer 38. The same materials as may be employed for the adhesion layer 32 may be employed as the material of the bonding layer 36. Note that in the present exemplary embodiment, the bonding force of the bonding layer 36 is stronger than the bonding force of the adhesion layer 32.

As illustrated in the example in FIG. 2 and FIG. 3, the protective layer 38 is provided above the bonding layer 36. The protective layer 38 of the present exemplary embodiment covers the entire upper face of the bonding layer 36 that covers the conversion layer 30, the upper face of the conversion layer 30 being covered by the adhesion layer 32 and the reflective layer 34. The protective layer 38 of the present exemplary embodiment has a function of protecting the conversion layer 30 from moisture such as humidity. Together with the bonding layer 36, the protective layer 38 of the present exemplary embodiment also has a function of fixing the reflective layer 34 to the sensor substrate 12 and the conversion layer 30. Examples of materials that may be employed as the material of the protective layer 38 include organic films such as PET, polyphenylene sulfide (PPS), oriented polypropylene (OPP), PEN (polyethylene naphthalate), PI, and the like. Moreover, an ALPET (registered trademark) sheet in which aluminum, for example a bonded aluminum foil, is stacked on an insulating sheet (film) such as polyethylene terephthalate may be employed as the protective layer 38.

In the following explanation, a state in which the conversion layer 30, the adhesion layer 32, the reflective layer 34, the bonding layer 36, and the protective layer 38 have been stacked on one another is referred to as a stacked body 19.

As illustrated in the example in FIG. 2 and FIG. 3, the elastic layer 42 is provided on the opposite side of the conversion layer 30 (on the upper side in FIG. 3) to the side provided with the sensor substrate 12. Specifically, as illustrated in FIG. 2 and FIG. 3, the elastic layer 42 of the present exemplary embodiment is stacked on the central portion 30B of the conversion layer 30 with the bonding layer 40 interposed therebetween, and projects substantially parallel to the sensor substrate 12 such that the conversion layer 30 is sandwiched between the conversion layer 30 and the elastic layer 42. As illustrated in FIG. 3, the elastic layer 42 is stacked on the stacked body 19 with the bonding layer 40 interposed therebetween only in a region corresponding to the central portion 30B of the conversion layer 30.

As illustrated in FIG. 2 and FIG. 3, the position of an end portion of the elastic layer 42 is similar to the position of end portions of the bonding layer 36 and the protective layer 38. The elastic layer 42 does not project into a region corresponding to the pad area 17, and does not directly contact the sensor substrate 12. In the radiation detector 10 of the present exemplary embodiment, since the elastic layer 42 is not provided in the region corresponding to the pad area 17, the elastic layer 42 is suppressed from getting in the way when performing what is referred to as re-work, such as connecting the cable 112 (see FIG. 6A, etc.) in the pad area 17.

As illustrated in the example in FIG. 2 and FIG. 3, the bonding layer 40 is provided in a region corresponding to the central portion 30B of the conversion layer 30. The bonding layer 40 has a function of fixing the elastic layer 42 to the stacked body 19. For example, the same materials as may be employed for the adhesion layer 32 and the bonding layer 36 may be employed as the material of the bonding layer 40.

As will be described in detail later, the elastic layer 42 has restoring force to return the sensor substrate 12 to a pre-bending state when bending of the sensor substrate 12 (base member 14) occurs. Specifically, the elastic layer 42 of the present exemplary embodiment has a greater restoring force with respect to bending than the sensor substrate 12. Moreover, the elastic layer 42 of the present exemplary embodiment has a higher rigidity than the sensor substrate 12, in order to make the sensor substrate 12 (base member 14) less liable to bend.

An organic material is preferably employed as the elastic layer 42 with the above characteristics, and for example a sheet employing at least one material out of PET, white PET, foamed white PET, or the like is preferably employed therefor. Other examples of the elastic layer 42 include an organic film of polycarbonate (PC), low density polyethylene (LDPE), PPS, OPP, PEN, PI or the like.

In the example of the present exemplary embodiment, the thickness of the elastic layer 42 is determined in advance according to the material of the elastic layer 42, the desired restoring force, and so on. The desired restoring force is set according to the thickness of the base member 14, the envisaged bending amount of the sensor substrate 12 (base member 14), and so on. The thickness may for example be 1 mm. Note that the thinner the elastic layer 42, the smaller the restoring force. The greater the thickness, the greater the restoring force and the less readily bending occurs. On the other hand, the greater the thickness, the more difficult it becomes to bend the sensor substrate 12 when such bending is desirable during the manufacturing processes of the sensor substrate 12, described later, and a dimension of the radiation detector 10 in the stacking direction P also increases. The thickness of the elastic layer 42 is thus preferably set to the lower limit thickness at which the desired restoring force can be obtained.

More specifically, the elastic layer 42 of the present exemplary embodiment preferably employs a material having a bending elastic modulus of from 150 MPa to 2500 MPa. The bending elastic modulus is, for example, measured according to the method set out in JIS K7171:2016. The elastic layer 42 preferably has higher bending rigidity than the base member 14 from the perspective of suppressing bending of the base member 14. Note that since the bending rigidity decreases as the bending elastic modulus decreases, the thickness of the elastic layer 42 has to be increased in order to obtain the desired bending rigidity, causing an increase in the overall thickness of the radiation detector 10. Considering the materials of the elastic layer 42 described above, the thickness of the elastic layer 42 tends to become comparatively large when attempting to obtain a bending rigidity in excess of 140,000 Pa·cm$^4$. Accordingly, in consideration of both obtaining an appropriate rigidity and the overall thickness of the radiation detector 10, the material employed for the elastic layer 42 preferably has a bending elastic modulus of from 150 MPa to 2500 MPa. The bending rigidity of the elastic layer 42 is preferably from 540 Pa·cm$^4$ to 140,000 Pa·cm$^4$.

The coefficient of thermal expansion of the elastic layer 42 of the present exemplary embodiment is preferably close to the coefficient of thermal expansion of the material of the conversion layer 30, and more preferably the ratio of the coefficient of thermal expansion of the elastic layer 42 with respect to the coefficient of thermal expansion of the conversion layer 30 (the coefficient of thermal expansion of the elastic layer 42 divided by the coefficient of thermal expansion of the conversion layer 30) is from 0.5 to 4. The coefficient of thermal expansion of the elastic layer 42 is preferably from 30 ppm/K to 200 ppm/K. For example, in cases in which CsI:Tl is employed as the material of the conversion layer 30, the coefficient of thermal expansion thereof is 50 ppm/K. In such cases, examples of materials that may be employed for the elastic layer 42 include LDPE with a coefficient of thermal expansion of from 100 ppm/K to 200 ppm/K, polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, PC with a coefficient of thermal expansion of 65 ppm/K, and TEFLON (registered trademark) with a coefficient of thermal expansion of from 45 ppm/K to 70 ppm/K.

In consideration of the bending elastic modulus mentioned above, the material of the elastic layer 42 preferably contains at least one material out of PET, PC, or LDPE.

From the perspective of elasticity, the elastic layer 42 preferably contains a material having a yield point. In the present exemplary embodiment, the "yield point" refers to the point at which stress does not increase but strain does increase on a curve expressing the relationship between stress and strain in the phenomenon in which stress suddenly decreases when the material is applied with tension, and is the apex of the stress-strain curve when the material is tested for tensile strength. Examples of resins having a yield point are generally hard resins with high viscosity, and soft resins with high viscosity and moderate strength. PC is an example of a hard resin with high viscosity. Polypropylene is an example of a soft resin with high viscosity and moderate strength.

Figure 5:
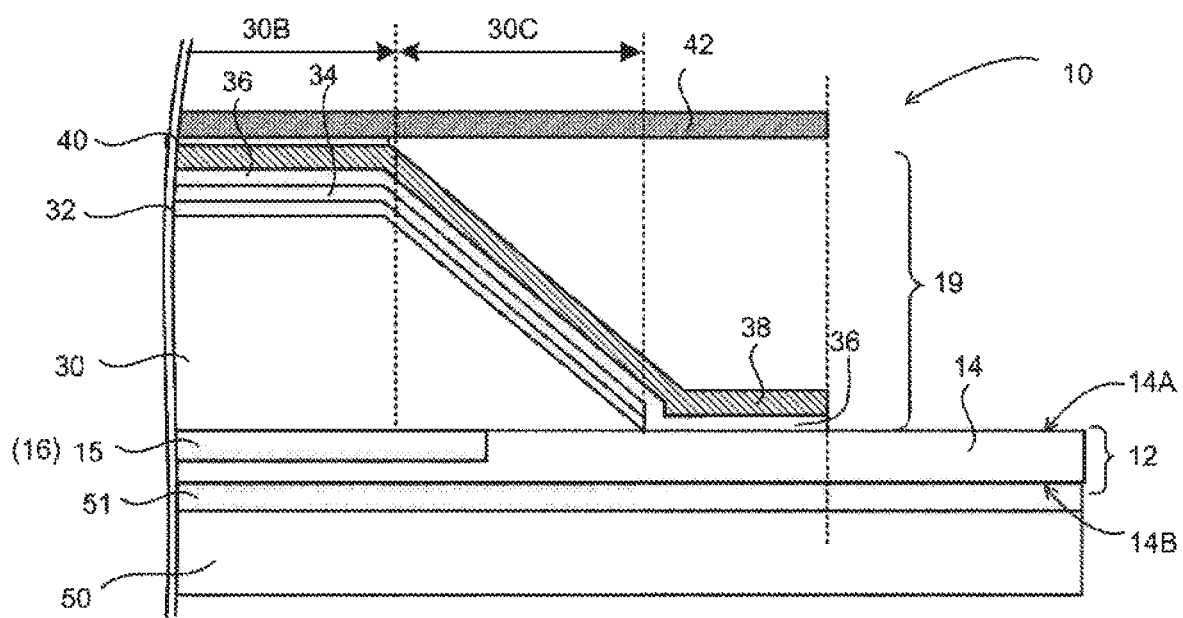
FIG. 5 is an explanatory diagram to explain an example of a manufacturing method of a radiation detector of the first exemplary embodiment.

As illustrated in the example in FIG. 5, in the radiation detector 10 of the present exemplary embodiment a lamination method or the like is used to form the sensor substrate 12 on a support body 50, such as a glass substrate with a greater thickness than the base member 14, with a separation layer 51 interposed therebetween. In cases in which the sensor substrate 12 is formed by a lamination method, a sheet configuring the base member 14 is affixed to the separation layer 51.

As previously described, the conversion layer 30, the adhesion layer 32, the reflective layer 34, the bonding layer 36, and the protective layer 38 are sequentially provided on the base member 14 to form the stacked body 19. The bonding layer 40 and the elastic layer 42 are sequentially formed on the stacked body 19. The sensor substrate 12 is then separated from the support body 50 using the separation layer 51. There is no particular limitation to the separation method. For example, during mechanical separation, separation of the sensor substrate 12 may be performed by starting separation at any of the four edges of the sensor substrate 12 (base member 14) and gradually peeling the sensor substrate 12 away from the support body 50 toward the edge opposing the start edge. As another example, during laser separation (laser lift-off), the sensor substrate 12 may be separated from the support body 50 by irradiating a laser onto a back face (a face on the opposite side to the face provided with the sensor substrate 12) of the support body 50 and breaking down the separation layer 51 with the laser that has passed through the support body 50.

Note that the sensor substrate 12 bends during separation of the sensor substrate 12 from the support body 50. In particular, the sensor substrate 12 is often bent while being separated from the support body 50 during mechanical separation. The flexible base member 14 employed in the sensor substrate 12 has a lower rigidity than a base member made of glass, and so bends more easily. When the sensor substrate 12 is bent, rather than bending as a whole, the base member 14 undergoes partial or local bending and distortion, and so the mode of bending may differ between respective positions in the plane of the base member 14 (the first surface 14A and the second surface 14B). In the present exemplary embodiment, this manner of bending and distortion occurring in such cases is referred to as "discontinuous bending", in contrast to cases in which the entire component bends as a whole. In particular, this discontinuous bending occurs comparatively readily near to the outer peripheral portion of the conversion layer 30.

In the radiation detector 10 of the present exemplary embodiment, the elastic layer 42 has a greater restoring force than the base member 14, and so when the sensor substrate 12 (base member 14) is bent in this manner, the portion where the bending occurs returns readily to its original state (the pre-bending state), enabling the base member 14 to be suppressed from bending excessively.

Conversely, were bending of the sensor substrate 12 (base member 14) not addressed, and in particular were discontinuous bending not addressed, the conversion layer 30 could readily detach from the sensor substrate 12, and the conversion layer 30 and the pixels 16 would be more liable to sustain damage.

In the radiation detector 10 of the present exemplary embodiment, the elastic layer 42 has a greater restoring force than the base member 14 as previously described, and so the bent portion readily returns to its original state (the pre-bending state) and the base member 14 is suppressed from bending excessively.

Thus, the radiation detector 10 of the present exemplary embodiment is capable of suppressing the effects of bending occurring when separating the sensor substrate 12 from the support body 50 during the manufacturing processes of the radiation detector 10 provided with the sensor substrate 12 including the flexible base member 14 manufactured using the support body 50.

Moreover, as illustrated in FIG. 2 and FIG. 3, in the radiation detector 10 of the present exemplary embodiment the elastic layer 42 is provided on the stacked body 19 even after the sensor substrate 12 has been separated from the support body 50. Thus, particularly when the sensor substrate 12 is handled on its own rather than as part of the radiographic imaging device 1 after manufacture of the radiation detector 10, since the elastic layer 42 has a large restoring force with respect to bending, issues arising due to the effects of the above-described bending can be suppressed even when the sensor substrate 12 (base member 14) undergoes bending.

Next, explanation follows regarding the radiographic imaging device 1 applied with the radiation detector 10 of the present exemplary embodiment. In the radiographic imaging device 1, the radiation detector 10 is provided inside a case that allows radiation to pass through, and that is waterproof, antibacterial, and tightly sealed.

Figure 6A:
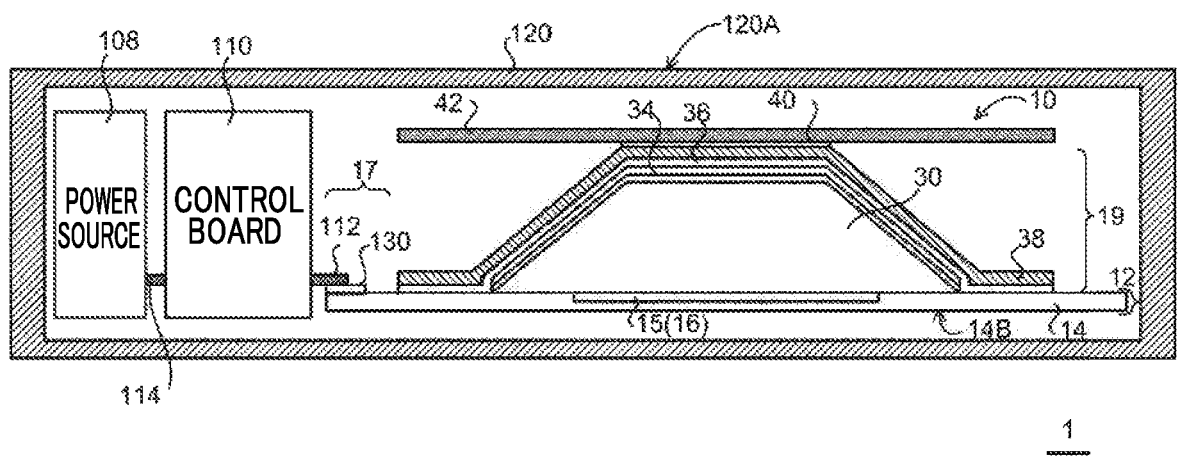
FIG. 6A is a cross-sectional view illustrating an example of a state in which a radiation detector is provided inside a case in a case in which a penetration side sampling (PSS) approach is adopted for a radiographic imaging device of an exemplary embodiment.

FIG. 6A illustrates an example of a state in which the radiation detector 10 is provided inside a case 120 in a case in which a PSS (penetration side sampling) approach is applied in the radiographic imaging device 1 of the present exemplary embodiment.

As illustrated in FIG. 6A, the radiation detector 10, the power source section 108, and the control board 110 are provided arranged inside the case 120 in a direction intersecting the stacking direction P. In the radiation detector 10, the second surface 14B of the base member 14 is provided in a state opposing the opposite side to an imaging face 120A side of the case 120 that is irradiated with radiation that has passed through the imaging subject, namely the side of the case 120 through which radiation is emitted.

Figure 6B:
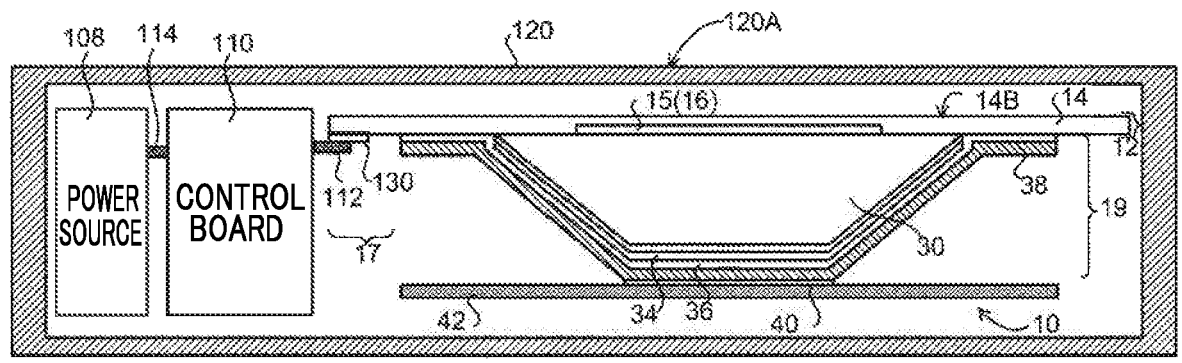
FIG. 6B is a cross-sectional view illustrating an example of a state in which a radiation detector is provided inside a case in a case in which an irradiation side sampling (ISS) approach is adopted for a radiographic imaging device of an exemplary embodiment.

FIG. 6B illustrates an example of a state in which the radiation detector 10 is provided inside the case 120, in a case in which an ISS approach is applied in the radiographic imaging device 1 of the present exemplary embodiment.

As illustrated in FIG. 6B, the radiation detector 10, the power source section 108, and the control board 110 are provided arranged inside the case 120 in a direction intersecting the stacking direction P. In the radiation detector 10, the second surface 14B of the base member 14 is provided so as to oppose an imaging face 120A, configuring an irradiated face that is irradiated with radiation, of the case 120 that is irradiated with radiation that has passed through the imaging subject.

The control board 110 is a substrate on which the image memory 106, the control section 100, and so on are formed, and is electrically connected to the pixels 16 of the sensor substrate 12 by the cable 112 including the plural signal lines that are connected to the pads 130 provided in the pad area 17 of the radiation detector 10. Note that in the present exemplary embodiment, the drive section 102 and the signal processing section 104 are provided on the cable 112 as what is known as a chip-on-film (COF). However, at least one out of the drive section 102 or the signal processing section 104 may be formed on the control board 110. The control board 110 and the power source section 108 are connected together by a power source line 114.

The case 120 is preferably lightweight, has a low absorption ratio of the radiation R, in particular X-rays, and high rigidity, and is preferably configured from a material that has a sufficiently high elastic modulus. A material having a bending elastic modulus of at least 10,000 MPa is preferably employed as the material of the case 120. Examples of materials suitably employed as the material of the case 120 include carbon or carbon fiber reinforced plastic (CFRP) having a bending elastic modulus of around 20,000 MPa to 60,000 MPa.

During capture of radiographic images by the radiographic imaging device 1, a load is applied to the imaging face 120A of the case 120 from the imaging subject. If the rigidity of the case 120 were insufficient, the load from the imaging subject would cause the sensor substrate 12 to bend, and there would be a concern of faults occurring, such as damage to the pixels 16. Housing the radiation detector 10 inside the case 120 configured from a material having a bending elastic modulus of at least 10,000 MPa enables bending of the sensor substrate 12 due to the load from the imaging subject to be suppressed.

The radiographic imaging devices 1 illustrated in FIG. 6A and FIG. 6B are capable of capturing radiographic images in a state in which the radiation detector 10 has been bent in a direction out of the plane of the second surface 14B of the base member 14. For example, radiographic images can be captured while a bent state of the radiation detector 10 persists as a result of the imaging site of the imaging subject.

In the radiographic imaging devices 1 illustrated in FIG. 6A and FIG. 6B, the power source section 108 and the control board 110 are provided in a peripheral portion of the case 120 that has relatively high rigidity. This enables the application of external force to be suppressed from affecting the power source section 108 and the control board 110.

Note that FIG. 6A and FIG. 6B each illustrate an embodiment in which both the power source section 108 and the control board 110 are provided on one side of the radiation detector 10, specifically, on the side of one edge of the rectangular radiation detector 10. However, there is no limitation to embodiments in which the power source section 108 and the control board 110 are provided at the positions illustrated in FIG. 6A and FIG. 6B. For example, the power source section 108 and the control board 110 may be provided distributed between two opposing edges of the radiation detector 10, or may be provided distributed between two adjacent edges of the radiation detector 10. Moreover, FIG. 6A and FIG. 6B each illustrate an embodiment in which the power source section 108 and the control board 110 are both configured as a single configuration section (substrate). However, there is no limitation to the embodiments illustrated in FIG. 6A and FIG. 6B, and at least one out of the power source section 108 or the control board 110 may be configured by plural configuration sections (substrates). For example, the power source section 108 may include a first power source section and a second power source section (neither of which are illustrated), and the first power source section and the second power source section may be provided distributed between two opposing edges of the radiation detector 10.

Note that in cases in which a radiographic image is captured while the overall radiographic imaging device 1 (radiation detector 10) is bent, the effects of this bending on the image can be suppressed by performing image correction.

Figure 6C:
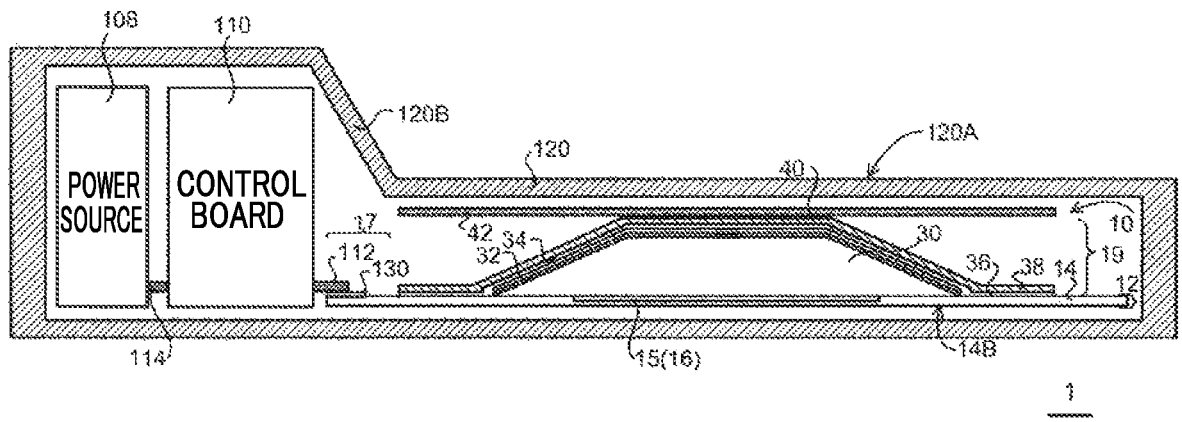
FIG. 6C is a cross-sectional view illustrating another example of a state in which a radiation detector is provided inside a case in a case in which a PSS approach is applied for a radiographic imaging device of an exemplary embodiment.

Often, the power source section 108 and the control board 110 will each have a greater thickness than the radiation detector 10, as in the examples illustrated in FIG. 6A and FIG. 6B. In such cases, as in the example illustrated in FIG. 6C, the thickness of the location of the case 120 where the radiation detector 10 is provided may be less than the thickness of the locations of the case 120 where the power source section 108 and the control board 110 are provided. In cases in which the thickness is varied between the locations of the case 120 where the power source section 108 and the control board 110 are respectively provided and the location of the case 120 where the radiation detector 10 is provided in this manner, since there might be a concern of causing discomfort or the like to the imaging subject who touches a boundary 120B where a step is created at a boundary between these locations, the boundary 120B is preferably provided with a slope.

So doing enables an ultra-thin portable electronic cassette to be configured according to the thickness of the radiation detector 10.

As another example, in such cases, the case 120 may be configured of different materials at the locations of the case 120 where the power source section 108 and the control board 110 are provided and the location of the case 120 where the radiation detector 10 is provided. Moreover, for example, the locations of the case 120 where the power source section 108 and the control board 110 are provided and the location of the case 120 where the radiation detector 10 is provided may be configured separately to each other.

Figure 6D:
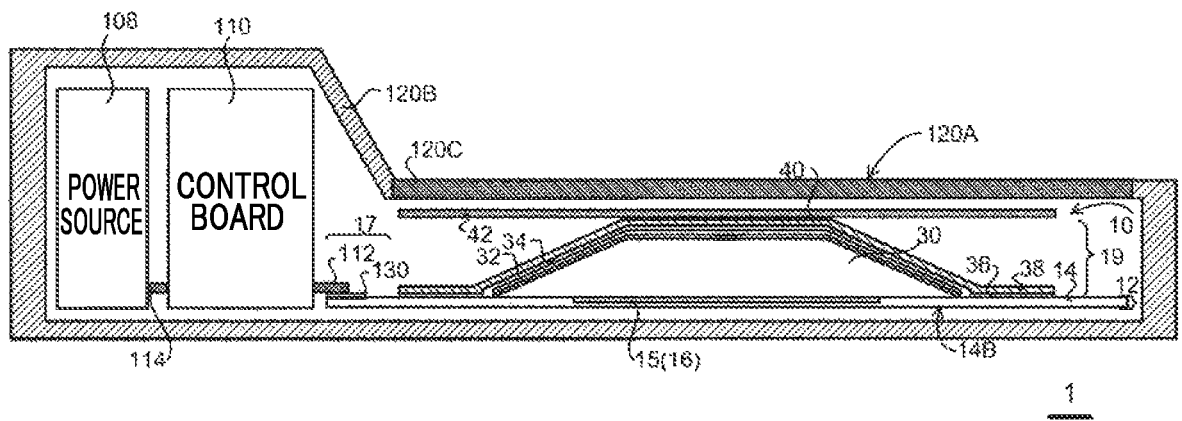
FIG. 6D is a cross-sectional view illustrating another example of a state in which a radiation detector is provided inside a case in a case in which a PSS approach is applied for a radiographic imaging device of an exemplary embodiment.

Moreover, as described above, the case 120 preferably has a low absorption ratio of the radiation R, in particular X-rays, and high rigidity, and is preferably configured from a material that has a sufficiently high elastic modulus. However, as in the example illustrated in FIG. 6D, a location 120C of the case 120 corresponding to the imaging face 120A may be configured with a low absorption ratio to the radiation R and high rigidity, and be configured from a material that has a sufficiently high elastic modulus, while other locations of the case 120 are configured from a different material than the location 120C, for example a material having a lower elastic modulus than the location 120C.

Figure 6E:
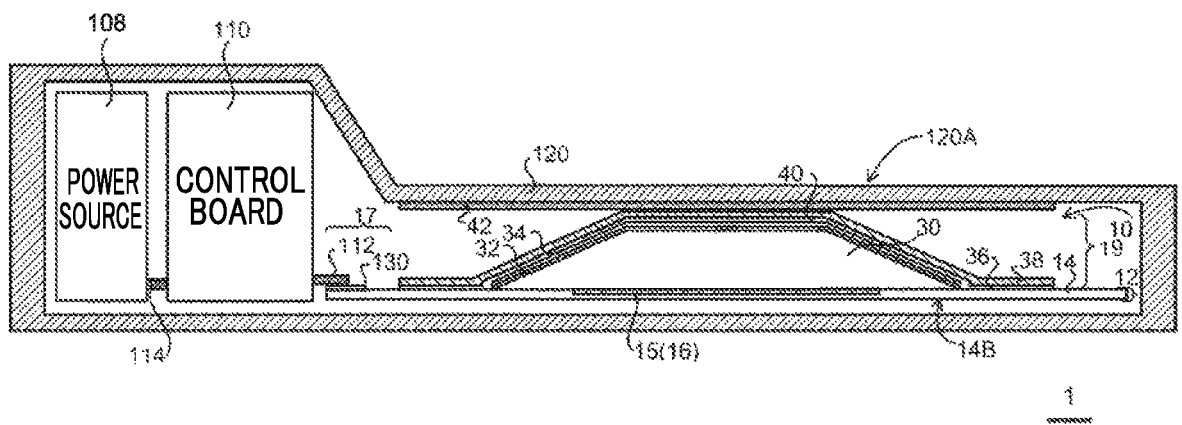
FIG. 6E is a cross-sectional view illustrating another example of a state in which a radiation detector is provided inside a case in a case in which a PSS approach is applied for a radiographic imaging device of an exemplary embodiment.

Alternatively, the radiation detector 10 and an inner wall face of the case 120 may contact each other as in the example illustrated in FIG. 6E. In such cases, the radiation detector 10 and the inner wall face of the case 120 may be bonded together through a bonding layer, or may simply be in contact with each other without providing a bonding layer. Such contact between the radiation detector 10 and the inner wall face of the case 120 further secures the rigidity of the radiation detector 10.

Figure 7A:
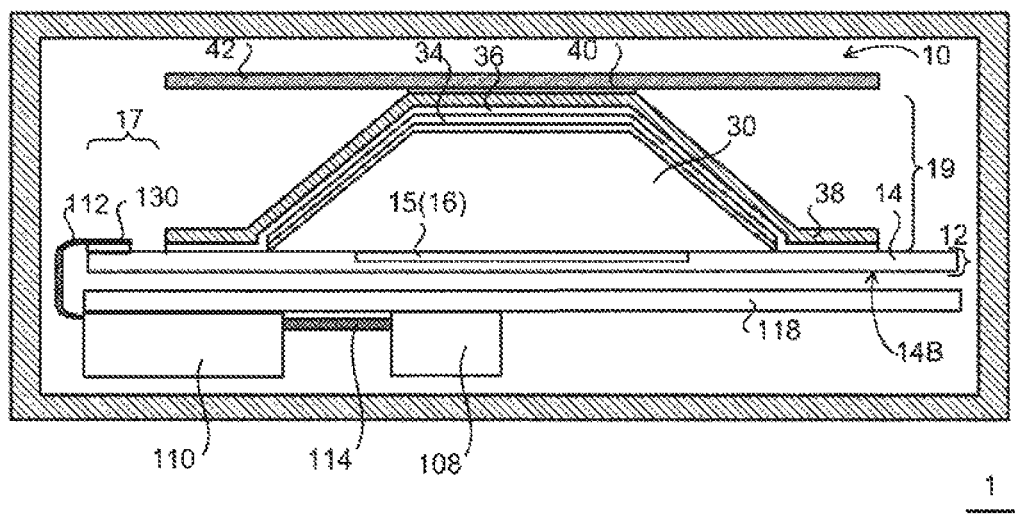
FIG. 7A is a cross-sectional view illustrating another example of a state in which a radiation detector is provided inside a case in a case in which a PSS approach is applied for a radiographic imaging device of an exemplary embodiment.

FIG. 7A illustrates another example of a state in which the radiation detector 10 is provided inside the case 120, in a case in which a PSS approach is applied in the radiographic imaging device 1 of the present exemplary embodiment.

As illustrated in FIG. 7A, the power source section 108 and the control board 110 are provided arranged inside the case 120 in a direction intersecting the stacking direction P, and the radiation detector 10 and the power source section 108 and control board 110 are provided arranged inside the case 120 along the stacking direction P.

Figure 7B:
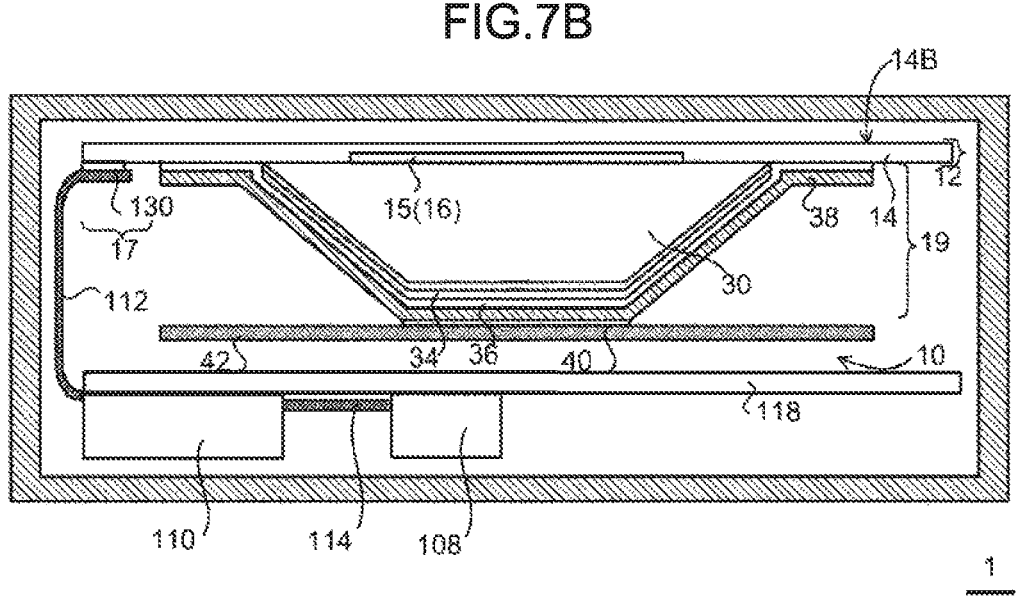
FIG. 7B is a cross-sectional view illustrating another example of a state in which a radiation detector is provided inside a case in a case in which an ISS approach is applied for a radiographic imaging device of an exemplary embodiment.

FIG. 7B illustrates another example of a state in which the radiation detector 10 is provided inside the case 120, in a case in which an ISS approach is applied in the radiographic imaging device 1 of the present exemplary embodiment.

As illustrated in FIG. 7B, the power source section 108 and the control board 110 are provided arranged inside the case 120 in a direction intersecting the stacking direction P, and the radiation detector 10 and the power source section 108 and control board 110 are provided arranged inside the case 120 along the stacking direction P.

In the radiographic imaging devices 1 illustrated in FIG. 7A and FIG. 7B, a base 118 is provided between the control board 110 and the power source section 108 and the base member 14 to support the radiation detector 10 and the control board 110. For example, carbon or the like is employed for the base 118.

The radiographic imaging devices 1 illustrated in FIG. 7A and FIG. 7B are capable of capturing radiographic images in a state in which the radiation detector 10 has been bent slightly in a direction out of the plane of the second surface 14B of the base member 14, for example in a state in which a central portion of the radiation detector 10 has been bent by around 1 mm to 5 mm. Since the control board 110 and power source section 108 and the radiation detector 10 are provided along the stacking direction P and the base 118 is provided, bending is less pronounced than in the radiographic imaging devices 1 illustrated in FIG. 7A and FIG. 7B.

Second Exemplary Embodiment

Next, explanation follows regarding a second exemplary embodiment. Note that a radiation detector 10 of the present exemplary embodiment has a similar configuration to the radiation detector 10 of the first exemplary embodiment (see FIG. 1 to FIG. 3), and so detailed explanation of this similar configuration is omitted.

Figure 8:
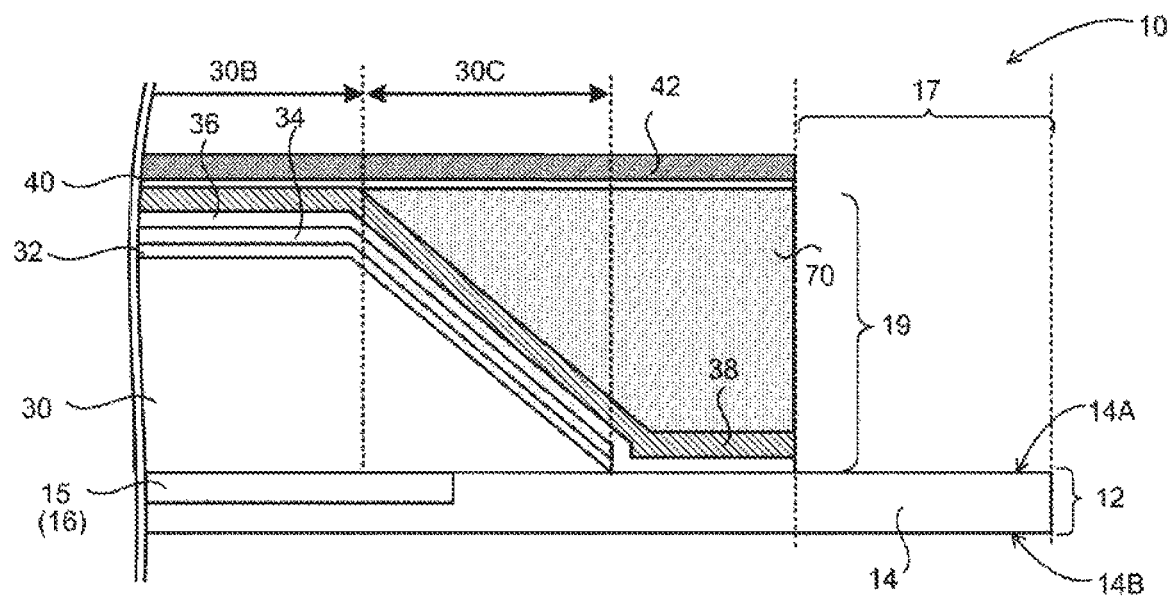
FIG. 8 is a cross-sectional view illustrating an example of a radiation detector of a second exemplary embodiment.

FIG. 8 is a cross-sectional view illustrating an example of the radiation detector 10 of the present exemplary embodiment. As illustrated in FIG. 8, in the radiation detector 10 of the present exemplary embodiment, a filler 70 is filled between the stacked body 19 and the elastic layer 42. Namely, as illustrated in FIG. 8, the radiation detector 10 of the present exemplary embodiment differs from the radiation detector 10 of the first exemplary embodiment in the respect that an open space between the stacked body 19 and the elastic layer 42 is filled with the filler 70.

The material of the filler 70 is not particularly limited, and sealing material used as a general semiconductor material or the like may be employed therefor. The filler 70 may have elasticity and restoring force similar to those of the elastic layer 42. Note that in the present exemplary embodiment, the bonding layer 40 is provided across the entire interface between the elastic layer 42 and the filler 70 in order to fix the elastic layer 42 to the filler 70. In the example illustrated in FIG. 8, the bonding layer 40 is provided over the entire surface of the elastic layer 42 that opposes the sensor substrate 12.

The method of providing the filler 70 is not particularly limited. For example, after forming the bonding layer 40 and the elastic layer 42 in sequence on the stacked body 19, the filler 70 may be provided by pouring flowable filler 70 into the space (gap) between the bonding layer 40 and the stacked body 19, and then curing the filler 70. Alternatively, for example, after forming the stacked body 19 on the sensor substrate 12, the filler 70 may be provided by placing flowable filler 70 at a location to be filled using the filler 70, and then forming the bonding layer 40 and the elastic layer 42 in sequence over the stacked body 19 and the filler 70.

Thus, in the radiation detector 10 of the present exemplary embodiment, the filler 70 is filled between the stacked body 19 and the elastic layer 42, such that the elastic layer 42 that projects beyond the central portion 30B (toward the end portion side of the sensor substrate 12) is supported by the filler 70. Thus, in the radiation detector 10 of the present exemplary embodiment, the elastic layer 42 is stably provided and is less liable to detach from the stacked body 19. Moreover, in the radiation detector 10 of the present exemplary embodiment, the stacked body 19 is fixed to the sensor substrate 12 by both the elastic layer 42 and the filler 70, such that the conversion layer 30 is less liable to detach from the sensor substrate 12.

Note that although the filler 70 entirely fills the space between the stacked body 19 and the elastic layer 42 in the example illustrated in FIG. 8 without leaving any gaps, there is no limitation to the embodiment illustrated in FIG. 8. For example, a local gap (a region where the filler 70 is not formed) may be left between the stacked body 19 and the elastic layer 42.

Third Exemplary Embodiment

Next, explanation follows regarding a third exemplary embodiment. Note that a radiation detector 10 of the present exemplary embodiment has a similar configuration to the radiation detector 10 of the first exemplary embodiment (see FIG. 1 to FIG. 3), and so detailed explanation of this similar configuration is omitted.

Figure 9:
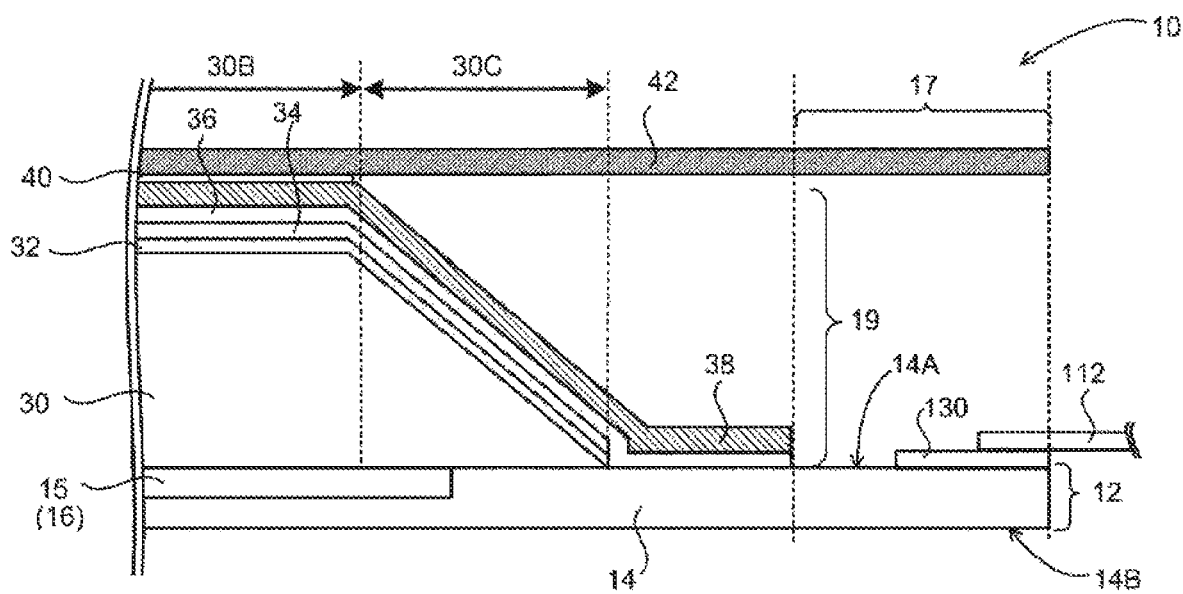
FIG. 9 is a cross-sectional view illustrating an example of a radiation detector of a third exemplary embodiment.

FIG. 9 is a cross-sectional view illustrating an example of the radiation detector 10 of the present exemplary embodiment. FIG. 9 illustrates a state in which the pad 130 previously described is provided in the pad area 17, and the cable 112 is electrically connected to the pad 130. As illustrated in FIG. 9, the radiation detector 10 of the present exemplary embodiment differs from the radiation detector 10 of the first exemplary embodiment in the respect that the elastic layer 42 is provided reaching right across a region opposing the pad area 17.

In the example illustrated in FIG. 9, the elastic layer 42 is provided over the entire region opposing the pad area 17, and an end portion of the elastic layer 42 and an end portion of the sensor substrate 12 (base member 14) are at the same position. In other words, a side face of the end portion of the elastic layer 42 and a side face of the end portion of the sensor substrate 12 are what is referred to as coplanar with each other. Note that there is no limitation to the example illustrated in FIG. 9, and the elastic layer 42 may be provided across part of the region opposing the pad area 17. In other words the end portion of the elastic layer 42 may be positioned at a position opposing a region within the pad area 17.

In the radiation detector 10 of the present exemplary embodiment, the elastic layer 42 is thus provided reaching right across the region opposing the pad area 17, thereby enabling a large restoring force (elasticity) with respect to bending to be imparted right up to the end portion of the sensor substrate 12.

Figure 10:
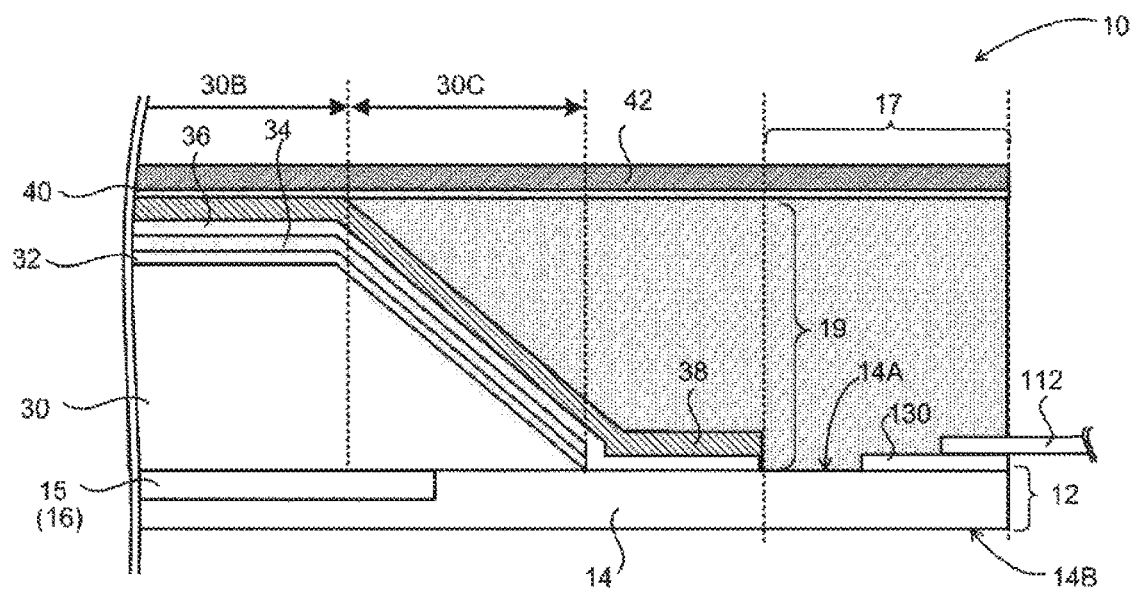
FIG. 10 is a cross-sectional view illustrating another example of a radiation detector of the third exemplary embodiment.

Note that in cases in which the elastic layer 42 is provided reaching right across the region opposing the pad area 17 in this manner, as illustrated in the example of a radiation detector 10 illustrated in FIG. 10, the filler 70 is preferably filled between the elastic layer 42 and the stacked body 19 similarly to in the second exemplary embodiment. In particular, as illustrated in the example in FIG. 10, the filler 70 is preferably also filled between the elastic layer 42 and the sensor substrate 12 in the pad area 17. Note that in such cases, filling with the filler 70 is preferably performed after the pad 130 and the cable 112 have been provided in the pad area 17.

By filling with the filler 70 as in the radiation detector 10 illustrated in FIG. 10, the elastic layer 42 is stably provided, such that the elastic layer 42 is less liable to detach from the stacked body 19 and the conversion layer 30 is less liable to detach from the sensor substrate 12. Note that as explained in the second exemplary embodiment, a configuration may be adopted in which local regions not filled with the filler 70 are present.

Figure 11:
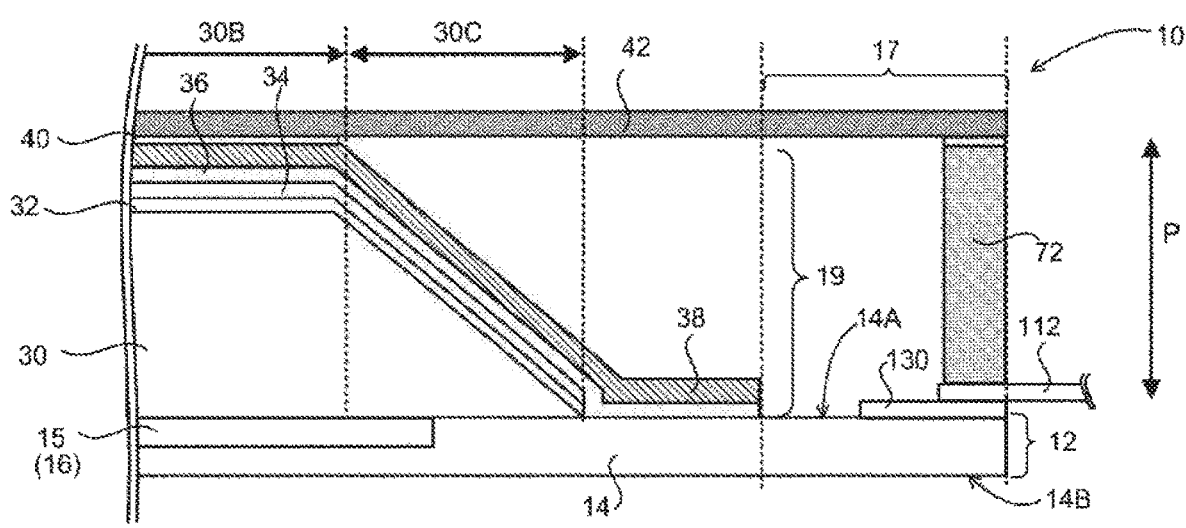
FIG. 11 is a cross-sectional view illustrating another example of a radiation detector of the third exemplary embodiment.

Alternatively, as in the example of a radiation detector 10 illustrated in FIG. 11, a spacer 72 functioning as a support portion that provides support between the end portion of the elastic layer 42 and the sensor substrate 12 may be provided in the pad area 17.

There is no particular limitation to the method of providing the spacer 72. For example, the spacer 72 may be affixed to the end portion of elastic layer 42 using a bonding agent or the like (not illustrated in the drawings), and the elastic layer 42 with the spacer 72 provided thereto may be affixed to the sensor substrate 12 in a state in which the stacked body 19, the bonding layer 40, the pad 130, and the cable 112 have been provided to the sensor substrate 12, such that the spacer 72 is provided between an end portion of the pad area 17 and the sensor substrate 12.

As in the radiation detector 10 illustrated in FIG. 11, in cases in which the spacer 72 is provided, a wider space is provided between the stacked body 19 and sensor substrate 12 and elastic layer 42 than in cases in which the filler 70 is filled therein. However, since the end portion of the elastic layer 42 is supported, the elastic layer 42 is less liable to peel away from the stacked body 19, and a large restoring force (elasticity) with respect to bending can be imparted closer toward the end portion of the sensor substrate 12.

Note that the width of the spacer 72 (in a direction intersecting the stacking direction P) is not limited to the width in the example illustrated in FIG. 11. For example, the width of the spacer 72 may be extended past a leading end of the cable 112 as far as a position close to the conversion layer 30. Alternatively, for example, the width of the spacer 72 may extend over the entire pad area 17.

Fourth Exemplary Embodiment

Next, explanation follows regarding a fourth exemplary embodiment. Note that a radiation detector 10 of the present exemplary embodiment has a similar configuration to the radiation detector 10 of the first exemplary embodiment (see FIG. 1 to FIG. 3), and so detailed explanation of this similar configuration is omitted.

Figure 12:
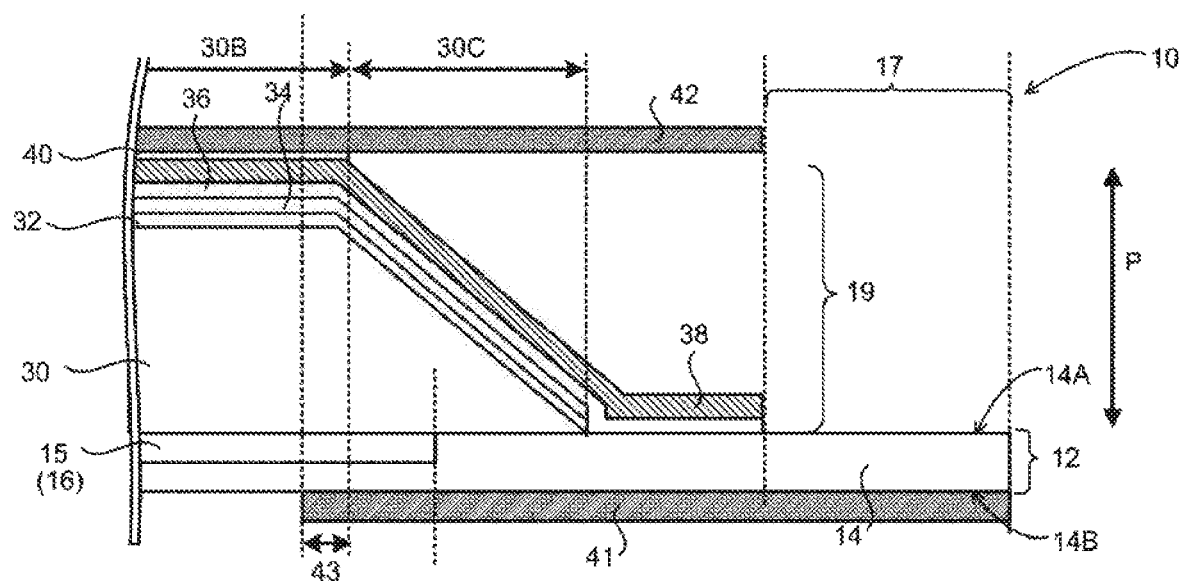
FIG. 12 is a cross-sectional view illustrating an example of a radiation detector of a fourth exemplary embodiment.

FIG. 12 is a cross-sectional view illustrating an example of the radiation detector 10 of the present exemplary embodiment. As illustrated in FIG. 12, the radiation detector 10 of the present exemplary embodiment differs from the radiation detector 10 of the first exemplary embodiment in the respect that an elastic member 41 is provided to the second surface 14B of the base member 14 of the sensor substrate 12.

As illustrated in FIG. 12, the elastic member 41 is provided to the second surface 14B of the base member 14 so as to reach from an outer edge of the base member 14 as far as part of the region provided with the conversion layer 30, such that a leading end of the elastic member 41 is positioned within the central portion 30B of the conversion layer 30. Note that the elastic member 41 is for example formed by being affixed to the second surface 14B through a bonding layer (not illustrated in the drawings) similar to that employed for the elastic layer 42.

Similarly to the elastic layer 42, the elastic member 41 provides restoring force to return the sensor substrate 12 to a pre-bending state when the sensor substrate 12 has been bent. Specifically, the elastic member 41 of the present exemplary embodiment has a greater restoring force with respect to bending than the sensor substrate 12. Moreover, the elastic member 41 of the present exemplary embodiment has a higher rigidity than the sensor substrate 12 so as to be bend less readily than the sensor substrate 12 (base member 14).

Similarly to the elastic layer 42 described previously, the coefficient of thermal expansion of the elastic member 41 of the present exemplary embodiment is preferably close to the coefficient of thermal expansion of the material of the conversion layer 30, and more preferably the ratio of the coefficient of thermal expansion of the elastic member 41 with respect to the coefficient of thermal expansion of the conversion layer 30 (the coefficient of thermal expansion of the elastic member 41 divided by the coefficient of thermal expansion of the conversion layer 30) is from 0.5 to 4. The coefficient of thermal expansion of the elastic member 41 is preferably from 30 ppm/K to 200 ppm/K. For example, in cases in which CsI:Tl is employed as the material of the conversion layer 30, the coefficient of thermal expansion thereof is 50 ppm/K. In such cases, examples of materials that may be employed for the elastic member 41 include LDPE with a coefficient of thermal expansion of from 100 ppm/K to 200 ppm/K, polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, PC with a coefficient of thermal expansion of 65 ppm/K, and TEFLON (registered trademark) with a coefficient of thermal expansion of from 45 ppm/K to 70 ppm/K.

Similarly to the elastic layer 42, an organic material is preferably employed as the elastic member 41 with the above characteristics, and for example a sheet employing at least one material out of PET, white PET, foamed white PET, PC, LDPE, PPS, OPP, PEN, PI, or the like is preferably employed.

Thus, in the radiation detector 10 of the present exemplary embodiment, the elastic member 41 is provided reaching from the outer edge of the base member 14 to as far as part of the region provided with the conversion layer 30, thereby enabling restoring force and rigidity to be imparted to the outer edge portion of the sensor substrate 12.

Moreover, in the radiation detector 10 of the present exemplary embodiment, parts of the elastic layer 42 and the elastic member 41 are provided opposing each other from across the sensor substrate 12 and the stacked body 19 (conversion layer 30), thereby enabling their mutual restoring forces and rigidity to augment each other, and thus enabling the effects of bending of the base member 14 to be suppressed.

Note that the region where the elastic member 41 and the elastic layer 42 are provided opposing one another preferably includes an overlap region 43 that has a predetermined overlap into the central portion 30B of the conversion layer 30 from the boundary with the peripheral edge portion 30C.

The peripheral edge portion 30C of the conversion layer 30 slopes so as to decrease in thickness on progression toward the outer side. Thus, discontinuous bending of the sensor substrate 12 readily occurs in the vicinity of the boundary between the central portion 30B and the peripheral edge portion 30C where the thickness of the conversion layer 30 changes. It is therefore preferable to include the overlap region 43 in the predetermined region within the central portion 30B of the conversion layer 30 from the boundary with the peripheral edge portion 30C where discontinuous bending readily occurs.

Note that the region configuring the overlap region 43 is not limited to the example illustrated in FIG. 12. For example, although only a region corresponding to the central portion 30B configures the overlap region 43 in FIG. 12, the overlap region 43 may be a region in a predetermined range including the boundary between the central portion 30B and the peripheral edge portion 30C, and spanning from the central portion 30B into the peripheral edge portion 30C.

Note that as long as the region provided with the elastic member 41 falls within the overlap region 43, there is no limitation to the example illustrated in FIG. 12. For example, the elastic member 41 may be provided across the entire second surface 14B of the base member 14.

As long as the above conditions are satisfied, there are no particular limitations to the specific region configuring the overlap region 43 and the region provided with the elastic member 41, which may be determined according to the characteristics of the elastic layer 42, the position of the pixel region 15, the sampling approach, and so on.

As described above, the radiation detectors 10 of the respective exemplary embodiments described above each include the sensor substrate 12 including the flexible base member 14 and the layer provided on the first surface 14A of the base member 14 and formed with plural of the pixels 16 configured to accumulate electrical charge generated in response to light converted from radiation, the conversion layer 30 provided on the first surface 14A side of the sensor substrate 12 and configured to convert radiation into light, and the elastic layer 42 provided on the opposite side of the conversion layer 30 to the side provided with the sensor substrate 12, and configured with a greater restoring force with respect to bending than the sensor substrate 12.

The radiation detectors 10 of the respective exemplary embodiments described above each include the elastic layer 42 provided on the opposite side of the conversion layer 30 to the side provided with the sensor substrate 12, and configured with a greater restoring force with respect to bending than the sensor substrate 12. This enables the effects of bending that occurs during separation of the sensor substrate 12 from the support body 50 during the manufacturing processes of the radiation detector 10 provided with the sensor substrate 12 including the flexible base member 14 manufactured using the support body 50 to be suppressed compared to configurations provided with a layer which does not have a greater restoring force with respect to bending than the sensor substrate 12. Moreover, since the radiation detectors 10 of the respective exemplary embodiments enable the effects of such bending to be suppressed, detachment of the conversion layer 30 from the sensor substrate 12, and damage to the pixels 16 and the conversion layer 30 can be suppressed.

Note that as long as the region provided with the elastic layer 42 is a region that covers at least the central portion 30B of the conversion layer 30, there is no limitation to the respective exemplary embodiments described above. For example, the end portion of the elastic layer 42 may be provided so as to reach from the region covering the central portion 30B to a region corresponding to the outer periphery of the peripheral edge portion 30C (an edge of the conversion layer 30 on the side contacting the first surface 14A). As an example of a region provided with the elastic layer 42, as in the example of a radiation detector 10 illustrated in FIG. 13, the elastic layer 42 may be formed across the bonding layer 40 so as to cover the front surface (upper face) of the stacked body 19, in other words, without providing a gap between the elastic layer 42 and the stacked body 19. In the example illustrated in FIG. 13, the elastic layer 42 covers the entire central portion 30B and part of the peripheral edge portion 30C of the conversion layer 30 included in the stacked body 19, and the end portion of the elastic layer 42 is positioned in a region corresponding to the peripheral edge portion 30C. Alternatively, for example, as in the example of a radiation detector 10 illustrated in FIG. 14, the end portion of the elastic layer 42 may project further toward the outer side than the end portion of the sensor substrate 12.

Figure 15:
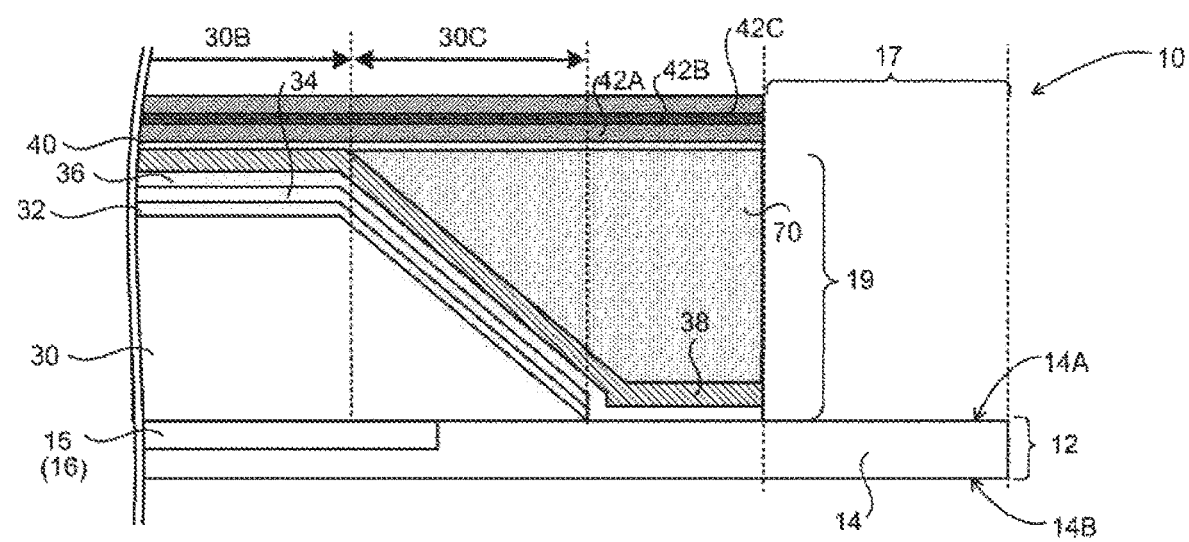
FIG. 15 is a cross-sectional view illustrating another example of a radiation detector of an exemplary embodiment.

Although the elastic layer 42 is configured by a single layer (one layer) in the respective exemplary embodiments described above, the elastic layer 42 may be configured by multiple layers. For example, as in the example of a radiation detector 10 illustrated in FIG. 15, the elastic layer 42 may be a multi-layered film configured of three layers in which a first elastic layer 42A, a second elastic layer 42B, and a third elastic layer 42C are stacked in sequence from the side closest to the stacked body 19. Note that the radiation detector 10 illustrated in FIG. 15 is an example of a radiation detector 10 in which the elastic layer 42 of the radiation detector 10 illustrated in FIG. 8 previously described is configured with multiple layers. In cases in which the elastic layer 42 has multiple layers in this manner, it suffices for the elastic layer 42 as a whole to have a greater restoring force with respect to bending than the sensor substrate 12.

In cases in which the elastic layer 42 has multiple layers, each of the layers included in the elastic layer 42 preferably has a different function. For example, in the example illustrated in FIG. 15, the first elastic layer 42A and the third elastic layer 42C may be configured as layers having a non-conductive anti-static function, while the second elastic layer 42B is configured as a conductive layer such that the elastic layer 42 has an electromagnetic shielding function. In such cases, the first elastic layer 42A and the third elastic layer 42C may employ an anti-static film such as a film employing the anti-static coating COLCOAT (trade name, manufactured by COLCOAT Co., Ltd.). The second elastic layer 42B may employ a conductive sheet or a conductive mesh sheet made of Cu or the like.

For example, in cases in which the sampling approach of the radiation detector 10 is an ISS approach, the control board 110, the power source section 108, and the like may be provided on the upper side of the sensor substrate 12 (stacked body 19). Providing the elastic layer 42 with an anti-static function in this manner enables electromagnetic noise from the control board 110 and the power source section 108 to be shielded.

Figure 16:
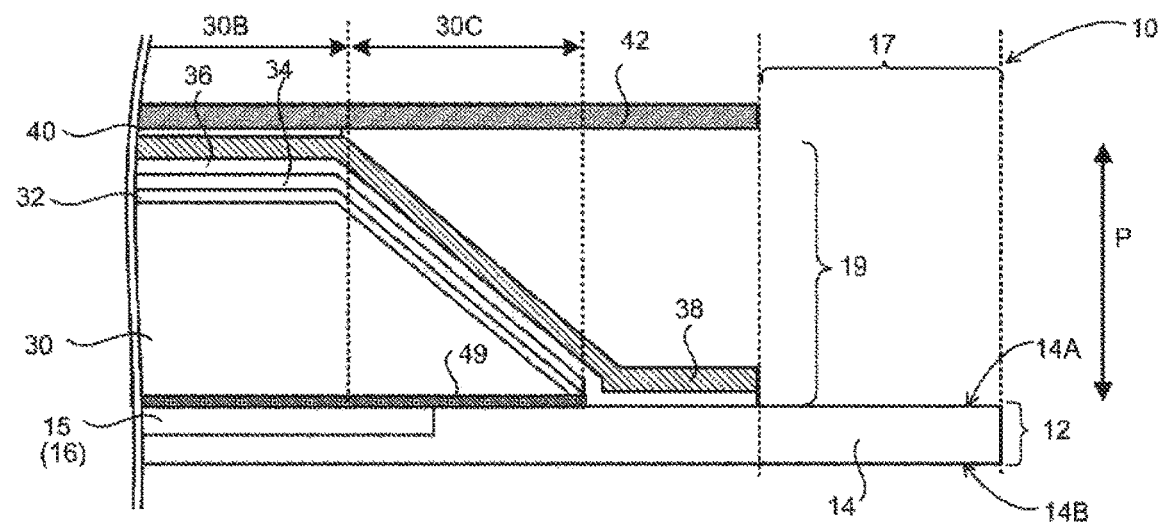
FIG. 16 is a cross-sectional view illustrating another example of a radiation detector of an exemplary embodiment.

Note that in the exemplary embodiments described above, explanation has been given regarding embodiments in which the conversion layer 30 is provided directly to the sensor substrate 12. However, there is no limitation to such embodiments, and another layer (film) may be provided between the sensor substrate 12 and the conversion layer 30. For example, the radiation detector 10 may include a cohesion layer 49 between the sensor substrate 12 and the conversion layer 30 as in the example illustrated in FIG. 16. In other words, the sensor substrate 12 may be stacked on the conversion layer 30 with the cohesion layer 49 therebetween. Since including the cohesion layer 49 enhances the level of cohesion between the sensor substrate 12 and the conversion layer 30, the conversion layer 30 detaches from the sensor substrate 12 less readily than in cases in which the cohesion layer 49 is not provided. Accordingly, in cases in which the cohesion layer 49 is provided, the rigidity of the elastic layer 42 may be reduced in comparison to cases in which the cohesion layer 49 is not provided. A Parylene film or the like may be employed as the cohesion layer 49.

Figure 17:
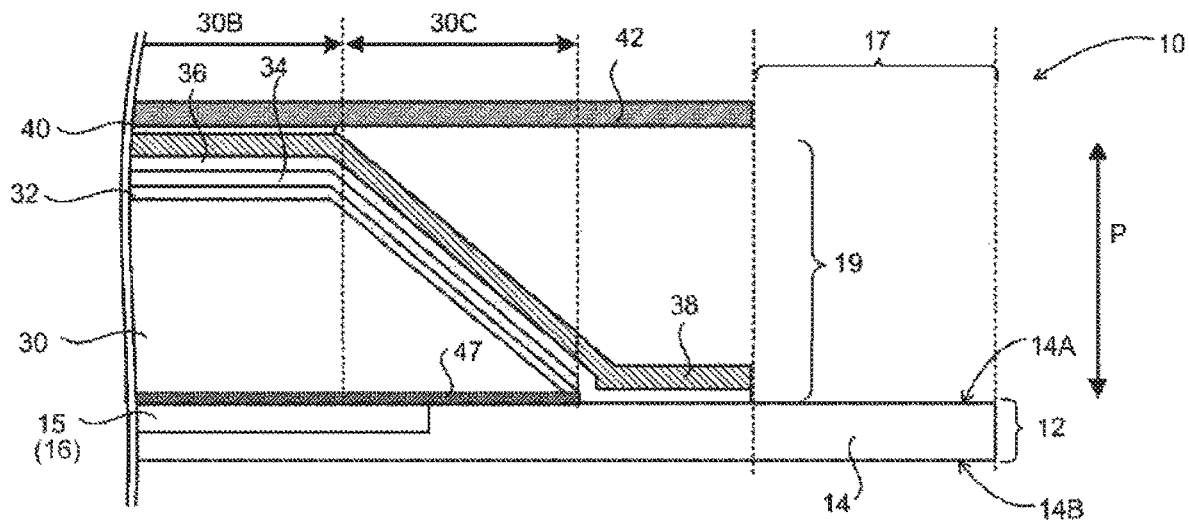
FIG. 17 is a cross-sectional view illustrating another example of a radiation detector of an exemplary embodiment.

As another example, the radiation detector 10 may include a buffer layer 47 between the sensor substrate 12 and the conversion layer 30 as in the example illustrated in FIG. 17. The buffer layer 47 has a function of buffering the difference between the coefficient of thermal expansion of the conversion layer 30 and the coefficient of thermal expansion of the base member 14. The coefficient of thermal expansion of the buffer layer 47 is a coefficient of thermal expansion lying between the coefficient of thermal expansion of the sensor substrate 12 and the coefficient of thermal expansion of the conversion layer 30. The greater the difference between the coefficient of thermal expansion of the conversion layer 30 and the coefficient of thermal expansion of the base member 14, the more preferable it is that the radiation detector 10 includes the buffer layer 47. For example, in cases in which XENOMAX (registered trademark) is employed for the base member 14, the difference to the coefficient of thermal expansion of the conversion layer 30 is greater than it would be with other materials, and so the buffer layer 47 is preferably provided as in the radiation detector 10 illustrated in FIG. 17. A PI film or a Parylene film may be employed as the buffer layer 47.

In the exemplary embodiments described above, explanation has been given regarding embodiments in which the radiation detector 10 is manufactured using a lamination method. However, there is no limitation to such embodiments, and the radiation detector 10 may be manufactured using a coating method. Moreover, explanation has been given regarding embodiments in which the sensor substrate 12 is separated from the support body 50 by mechanical separation. However, the sensor substrate 12 may be separated from the support body 50 by laser separation.

In cases in which a CsI scintillator is employed as the conversion layer 30, the conversion layer 30 may be formed on the sensor substrate 12 using a different method to that of the present exemplary embodiment. For example, CsI vapor deposited on an aluminum sheet or the like using a vapor phase deposition method may be prepared, and the conversion layer 30 may be formed on the sensor substrate 12 by affixing the side of the CsI that does not contact the aluminum sheet to the pixels 16 of the sensor substrate 12 using an adhesive sheet or the like. In such cases, a product obtained by covering the overall conversion layer 30 including the aluminum sheet with the protective layer 38 is preferably affixed to the pixels 16 of the sensor substrate 12. Note that in such cases, the side of the conversion layer 30 contacting the pixels 16 configures a growth direction tip end side of the columnar crystals.

Unlike the radiation detector 10 of the present exemplary embodiment, GOS ($Gd_2O_2S:Tb$) or the like may be employed in place of CsI as the conversion layer 30. In such cases, a sheet on which GOS has been distributed using a resin binder or the like may be prepared and affixed to a support body formed from white PET or the like using an adhesion layer or the like, and the side of the GOS that is not affixed to the support body may be affixed to the pixels 16 of the sensor substrate 12 using an adhesive sheet or the like to form the conversion layer 30 on the sensor substrate 12. Note that the efficiency of radiation to visible light conversion is greater when CsI is employed than when GOS is employed for the conversion layer 30.

In the exemplary embodiments described above, explanation has been given regarding embodiments in which the pixels 16 are arrayed in a two-dimensional matrix pattern as illustrated in FIG. 1. However, there is no limitation thereto, and the pixels 16 may be arrayed in one dimension, or may be arrayed in a honeycomb formation. The shape of the pixels is not limited, and the pixels may be rectangular or polygonal, for example hexagonal, in shape. Obviously the shape of the pixel region 15 is likewise not limited.

The configurations and manufacturing methods of the radiographic imaging device 1, the radiation detector 10, and so on of the exemplary embodiments described above are merely examples thereof, and obviously modifications are possible according to circumstances within a range not departing from the spirit of the present invention.

Other Exemplary Embodiments

First, explanation follows regarding other exemplary embodiments of the elastic layer 42, with reference to FIG. 18 to FIG. 30.

Figure 18:
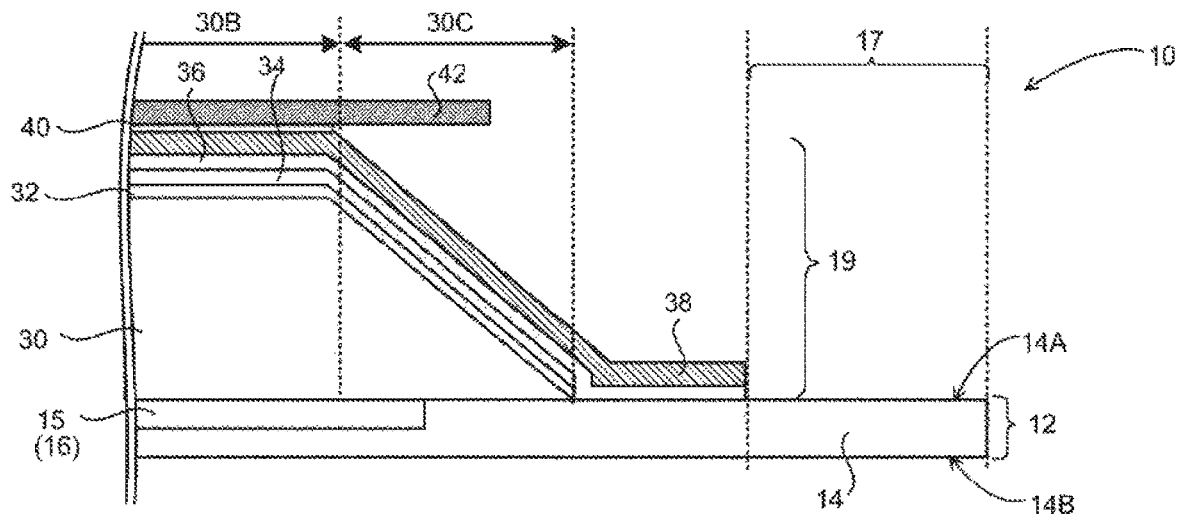
FIG. 18 is a cross-sectional view illustrating an example of configuration of a radiation detector of an exemplary embodiment of technology disclosed herein.
Figure 19:
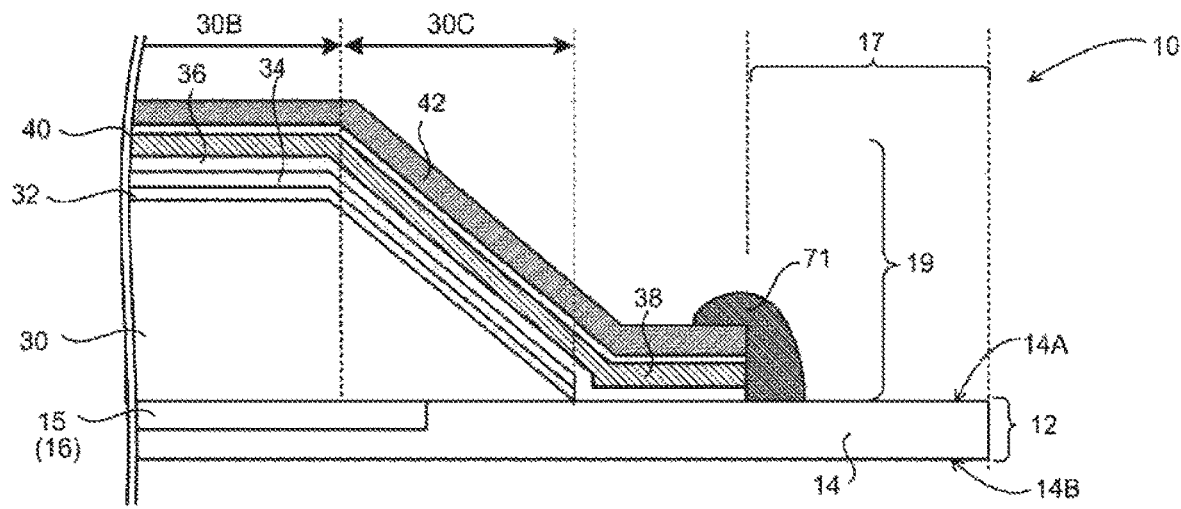
FIG. 19 is a cross-sectional view illustrating an example of configuration of a radiation detector of an exemplary embodiment of technology disclosed herein.

As illustrated in FIG. 18, in cases in which the elastic layer 42 extends over regions corresponding to both the central portion 30B and the peripheral edge portion 30C of the conversion layer 30, the elastic layer 42 may be configured without providing an angled portion to follow the slope of the outer peripheral portion of the conversion layer 30. In such cases, the elastic layer 42 is bonded to the protective layer 38 through the bonding layer 40 at the region corresponding to the central portion 30B of the conversion layer 30. A space corresponding to the slope of the peripheral edge portion 30C of the conversion layer 30 is formed between the conversion layer 30 (the protective layer 38) and the elastic layer 42 at the region corresponding to the peripheral edge portion 30C of the conversion layer 30.

Figure 13:
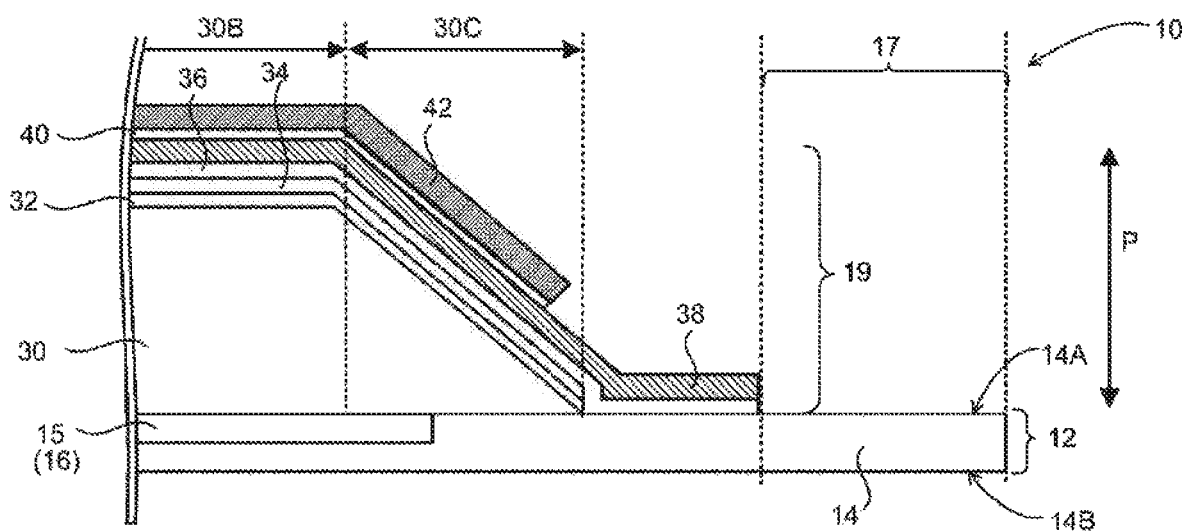
FIG. 13 is a cross-sectional view illustrating another example of a radiation detector of an exemplary embodiment.
Figure 14:
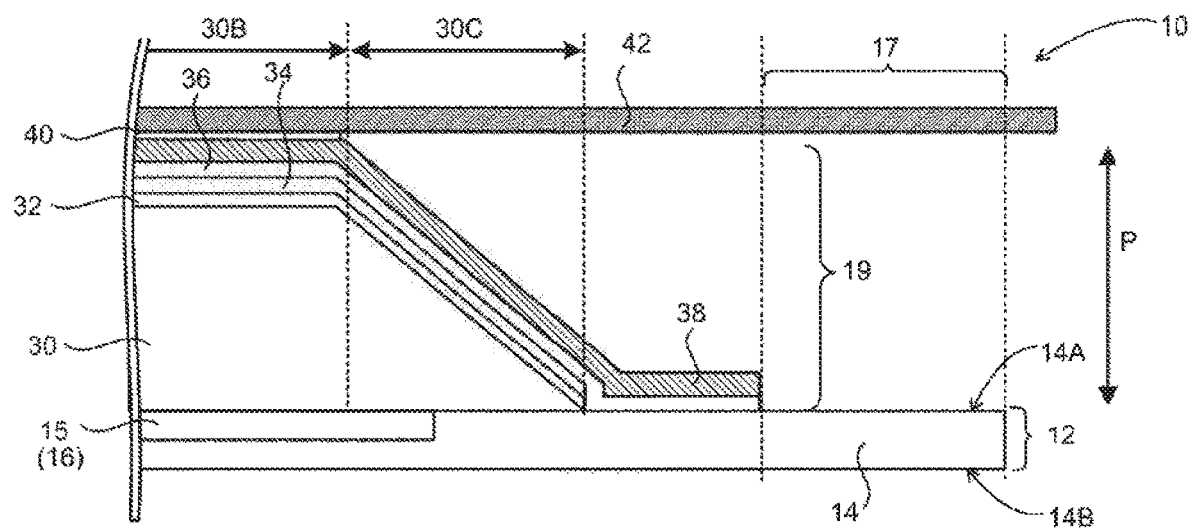
FIG. 14 is a cross-sectional view illustrating another example of a radiation detector of an exemplary embodiment.

As previously described, the cable 112 is connected to terminals 130 provided in a connection region at the outer peripheral portion of the sensor substrate 12. The sensor substrate 12 is connected to a control board (the control board 110, see FIG. 6A) through the cable 112. There is a concern that the cable 112 might detach from the sensor substrate 12 or that positional misalignment might arise were bending of the sensor substrate 12 to occur. In such cases it is necessary to perform a task to reconnect the cable 112 and the sensor substrate 12. This task to reconnect the cable 112 and the sensor substrate 12 is called re-work. As illustrated in FIG. 18 and FIG. 13 previously described, by arranging the end portion of the elastic layer 42 at the inner side of the end portion of the conversion layer 30, re-work can be performed more easily than in cases in which the elastic layer 42 extends as far as the vicinity of the connection region.

As illustrated in FIG. 19, FIG. 20, and FIG. 3 and FIG. 8 previously described, the end portion of the elastic layer 42 may be disposed at the outer side of the end portion of the conversion layer 30, and may be provided so as to be aligned with the end portions of the bonding layer 36 and the protective layer 38 that both extend onto the sensor substrate 12. Note that there is no need for the position of the end portion of the elastic layer 42 to align exactly with the position of the end portions of the bonding layer 36 and the protective layer 38.

In the example illustrated in FIG. 18, the outer peripheral portion of the elastic layer 42 is angled so as to follow the slope of the peripheral edge portion 30C of the conversion layer 30, and so as also to cover the portions of the bonding layer 36 and the protective layer 38 that cover the sensor substrate 12. Moreover, the end portion of the elastic layer 42 and the end portions of the bonding layer 36 and the protective layer 38 are aligned with each other. Note that there is no need for the position of the end portion of the elastic layer 42 to align exactly with the position of the end portions of the bonding layer 36 and the protective layer 38.

The end portions of the elastic layer 42, the bonding layer 40, the protective layer 38, and the bonding layer 36 are sealed with a sealing member 71. The sealing member 71 is preferably provided in a region spanning from the front surface of the sensor substrate 12 to the front surface of the elastic layer 42, and in a region not covering the pixel region 15. Resins may be employed as the material of the sealing member 71, and thermoplastic resins are particularly preferably employed therefor. Specifically, glues such as acrylic glues, urethane based glues, and the like may be employed as the sealing member 71. The elastic layer 42 has a higher rigidity than that of the protective layer 38, and there is a concern that restoring force due to the angle of the angled portion of the elastic layer 42 attempting to straighten out might act to cause the protective layer 38 to detach therefrom. Sealing the end portions of the elastic layer 42, the bonding layer 40, the protective layer 38, and the bonding layer 36 using the sealing member 71 enables such detachment of the protective layer 38 to be suppressed.

Figure 20:
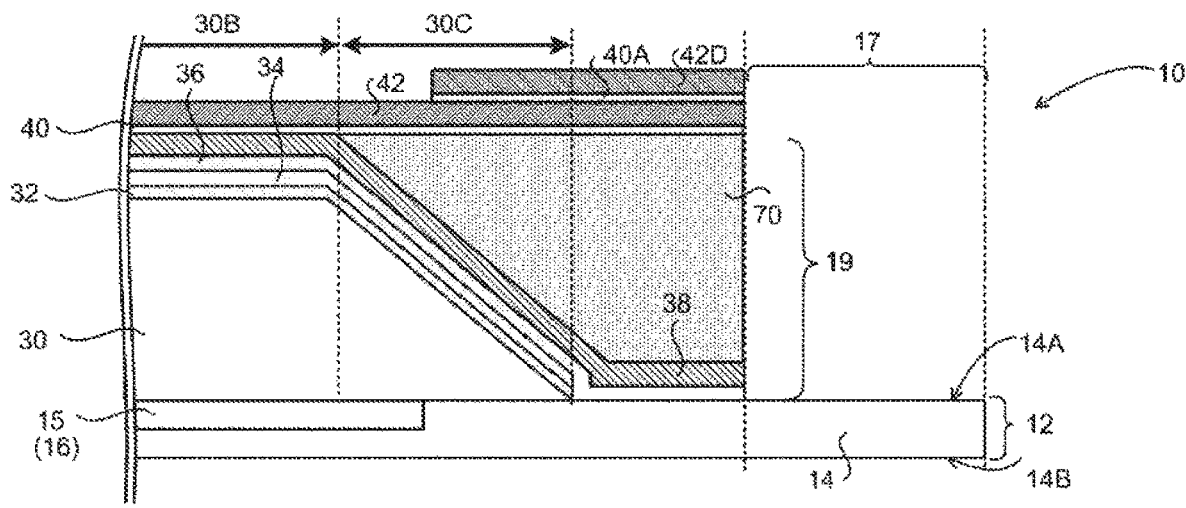
FIG. 20 is a cross-sectional view illustrating an example of configuration of a radiation detector of an exemplary embodiment of technology disclosed herein.
Figure 21:
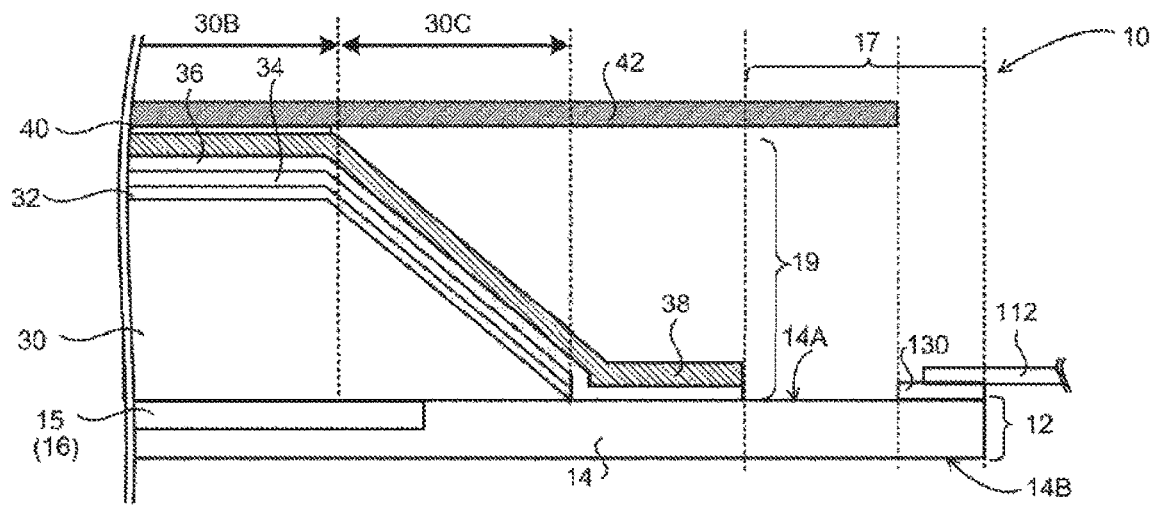
FIG. 21 is a cross-sectional view illustrating an example of configuration of a radiation detector of an exemplary embodiment of technology disclosed herein.

Similarly to in the embodiment illustrated in FIG. 8, in the example illustrated in FIG. 20, the filler 70 is provided in a space formed between the conversion layer 30 (the protective layer 38) and the elastic layer 42 at the region corresponding to the peripheral edge portion 30C of the conversion layer 30 and also at the region further to the outside thereof. Moreover, at the region corresponding to the end portion of the conversion layer 30, an additional and separate elastic layer 42A is stacked on the front surface of the elastic layer 42 with a bonding layer 40A interposed therebetween. More specifically, the elastic layer 42D is provided in a region straddling the end portion (outer edge, edge) of the conversion layer 30. The elastic layer 42D may be configured from the same materials as the elastic layer 42. In the radiation detector 10, the amount of bending of the sensor substrate 12 is comparatively large at the end portion of the conversion layer 30. Forming a multi-layer structure from the elastic layers 42 and 42D at the region corresponding to the end portion of the conversion layer 30 enables the effect of suppressing bending of the sensor substrate 12 at the end portion of the conversion layer 30 to be enhanced.

As illustrated in FIG. 19, FIG. 20, and FIG. 3 and FIG. 8 previously described, in cases in which the end portion of the elastic layer 42 is disposed further to the outer side than the end portion of the conversion layer 30 and is provided in a state aligned with the end portions of the bonding layer 36 and the protective layer 38, re-work can also be performed more easily than in cases in which the elastic layer 42 extends as far as the vicinity of the connection region.

As illustrated in FIG. 21 to FIG. 24, a configuration may be adopted in which the end portion of the elastic layer 42 is provided in a state positioned further to the outer side than the end portions of the bonding layer 36 and the protective layer 38 that extend onto the sensor substrate 12, and positioned at the inner side of the end portion of the sensor substrate 12.

In the example illustrated in FIG. 20, the elastic layer 42 is bonded to the protective layer 38 through the bonding layer 40 at the region corresponding to the central portion 30B of the conversion layer 30. At the region corresponding to the peripheral edge portion 30C of the conversion layer 30 and also at the region further to the outer side thereof, a space corresponding to the slope of the peripheral edge portion 30C of the conversion layer 30 is formed between the conversion layer 30 (the protective layer 38) and the elastic layer 42, and between the sensor substrate 12 and the elastic layer 42.

In the example illustrated in FIG. 22, the end portion of the elastic layer 42 is supported by the spacer 72. Namely, one end of the spacer 72 is connected to the first surface 14A of the base member 14 of the sensor substrate 12, and the other end of the spacer 72 is connected to the end portion of the elastic layer 42. By using the spacer 72 to support the end portion of the elastic layer 42 that extends so as to form a space between itself and the sensor substrate 12, detachment of the elastic layer 42 can be suppressed. Moreover, the bending suppression effect from the elastic layer 42 can be caused to act as far as the vicinity of the end portion of the sensor substrate 12. Note that instead of providing the spacer 72, or in addition to providing the spacer 72, the space formed between the conversion layer 30 (the protective layer 38) and the elastic layer 42, and between the sensor substrate 12 and the elastic layer 42, may be filled with a filler in a similar manner to the example illustrated in FIG. 20.

In the example illustrated in FIG. 23, the outer peripheral portion of the elastic layer 42 is angled so as to follow the slope at the peripheral edge portion 30C of the conversion layer 30, and the outer peripheral portion of the elastic layer 42 covers the portion where the bonding layer 36 and the protective layer 38 cover the sensor substrate 12 and also covers the sensor substrate 12 at the outer side thereof. Namely, the end portions of the bonding layer 36 and the protective layer 38 are sealed by the elastic layer 42. The portion of the elastic layer 42 that extends over the sensor substrate 12 is bonded to the sensor substrate 12 through the bonding layer 40. By using the elastic layer 42 to cover the end portions of the bonding layer 36 and the protective layer 38 in this manner, detachment of the protective layer 38 can be suppressed. Note that the sealing member 71 may be employed to seal the end portion of the elastic layer 42, in a similar manner to the example illustrated in FIG. 18.

Figure 24:
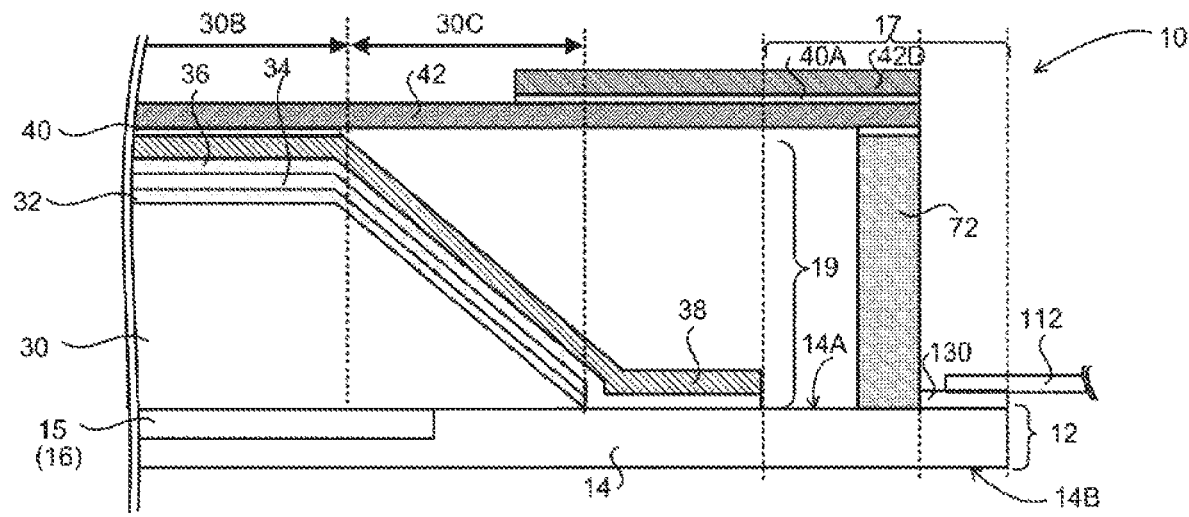
FIG. 24 is a cross-sectional view illustrating an example of configuration of a radiation detector of an exemplary embodiment of technology disclosed herein.

The example illustrated in FIG. 24 is an embodiment in which the end portion of the elastic layer 42 is supported by the spacer 72, and an additional and separate elastic layer 42D is stacked on the front surface of the elastic layer 42 at the region corresponding to the end portion of the conversion layer 30, with the bonding layer 40A interposed therebetween. More specifically, the elastic layer 42D is provided in a region straddling the end portion (outer edge, edge) of the conversion layer 30. The elastic layer 42D may be configured from the same materials as the elastic layer 42. In the radiation detector 10, the amount of bending of the sensor substrate 12 is comparatively large at the end portion of the conversion layer 30. Forming a multi-layer structure with the elastic layers 42 and 42D at the region corresponding to the end portion of the conversion layer 30 enables the effect of suppressing bending of the sensor substrate 12 at the end portion of the conversion layer 30 to be enhanced. Note that instead of providing the spacer 72, the space formed between the conversion layer 30 (the protective layer 38) and the elastic layer 42, and between the sensor substrate 12 and the elastic layer 42, may be filled with the filler 70 in a similar manner to the example illustrated in FIG. 20.

As illustrated in FIG. 25, FIG. 26, and FIG. 9 to FIG. 11 previously described, the end portion of the elastic layer 42 may be provided so as to be aligned with the end portion of the sensor substrate 12. Note that there is no need for the position of the end portion of the elastic layer 42 to align exactly with the position of the end portion of the sensor substrate 12.

Figure 25:
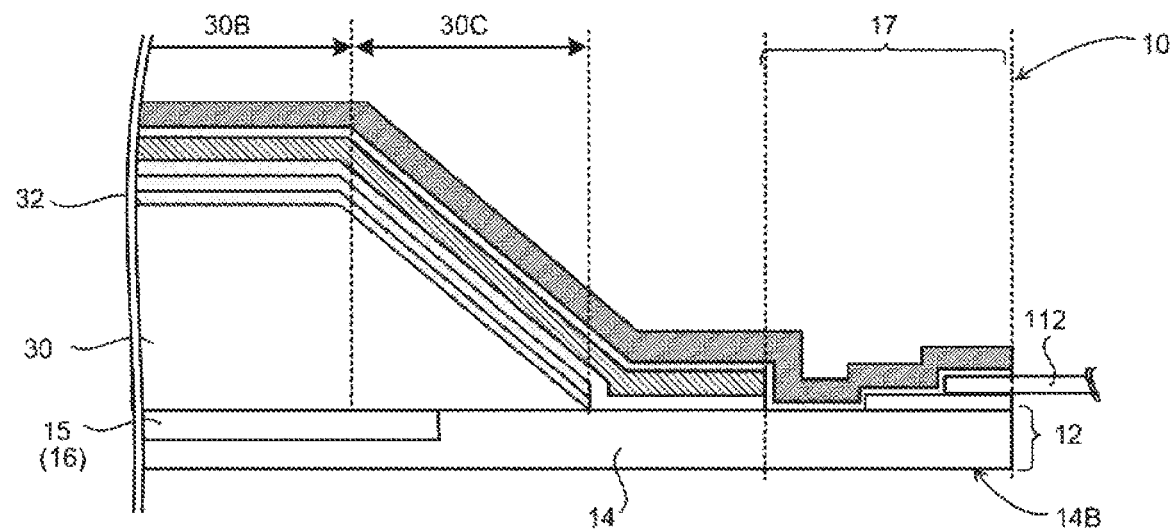
FIG. 25 is a cross-sectional view illustrating an example of configuration of a radiation detector of an exemplary embodiment of technology disclosed herein.

In the example illustrated in FIG. 25, the outer peripheral portion of the elastic layer 42 is angled so as to follow the slope of the peripheral edge portion 30C of the conversion layer 30. The outer peripheral portion of the elastic layer 42 covers a portion where the bonding layer 36 and the protective layer 38 cover the sensor substrate 12, a portion of the substrate at the outer side thereof, and the connection portions between the cable 112 and the terminals 130. The portions of the elastic layer 42 extending over the sensor substrate 12 and over the cable 112 are respectively bonded to the sensor substrate 12 and the cable 112 through the bonding layer 40. The connection portions between the cable 112 and the terminals 130 are covered by the bent elastic layer 42, enabling detachment of the cable 112 to be suppressed. Moreover, since the other end of the cable 112 is anticipated to be connected to a control board mounted with electronic components, there is a concern regarding comparatively large bending of the sensor substrate 12 occurring at the connection portions between the cable 112 and the terminals 130. Since the connection portions between the cable 112 and the terminals 130 are covered by the elastic layer 42, such bending of the sensor substrate 12 at these portions can be suppressed.

Figure 26:
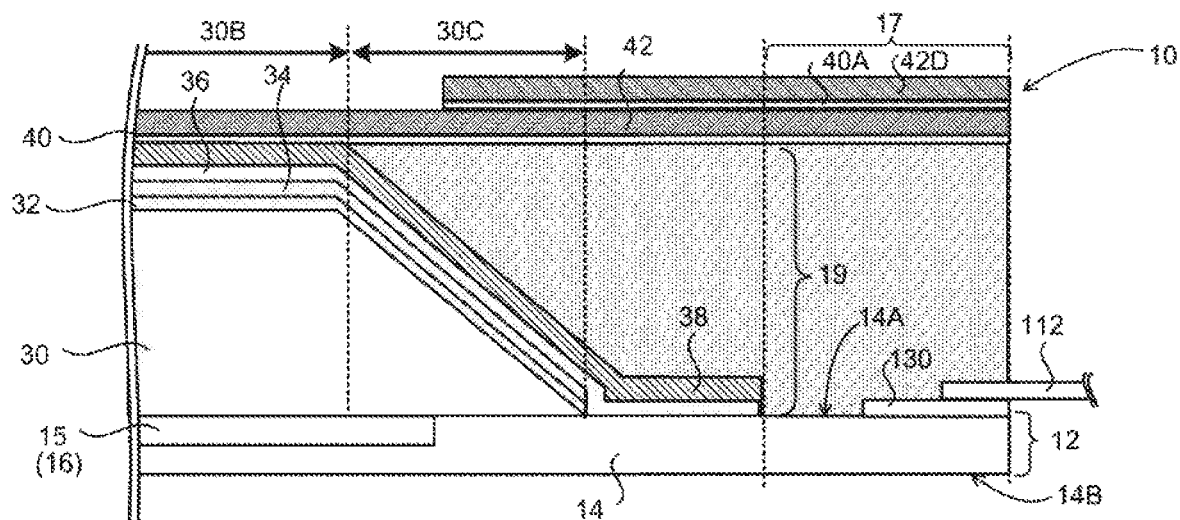
FIG. 26 is a cross-sectional view illustrating an example of configuration of a radiation detector of an exemplary embodiment of technology disclosed herein.

In the example illustrated in FIG. 26, a space formed between the conversion layer 30 (the protective layer 38) and the elastic layer 42, and between the sensor substrate 12 and the elastic layer 42, is filled with the filler 70. Moreover, an additional and separate bending elastic layer 42A is stacked on the front surface of the elastic layer 42 at the region corresponding to the end portion of the conversion layer 30, with the bonding layer 40A interposed therebetween. More specifically, the elastic layer 42D is provided in a region straddling the end portion (outer edge, edge) of the conversion layer 30. The elastic layer 42D may be configured from the same materials as the elastic layer 42. In the radiation detector 10, the amount of bending of the sensor substrate 12 is comparatively large at the end portion of the conversion layer 30. Forming a multi-layer structure with the elastic layers 42 and 42D at the region corresponding to the end portion of the conversion layer 30 enables the effect of suppressing bending of the sensor substrate 12 to be enhanced at the end portion of the conversion layer 30.

As illustrated in FIG. 27 to FIG. 30 and FIG. 14 previously described, the end portion of the elastic layer 42 may be provided so as to be positioned at the outer side of the end portion of the sensor substrate 12.

Figure 27:
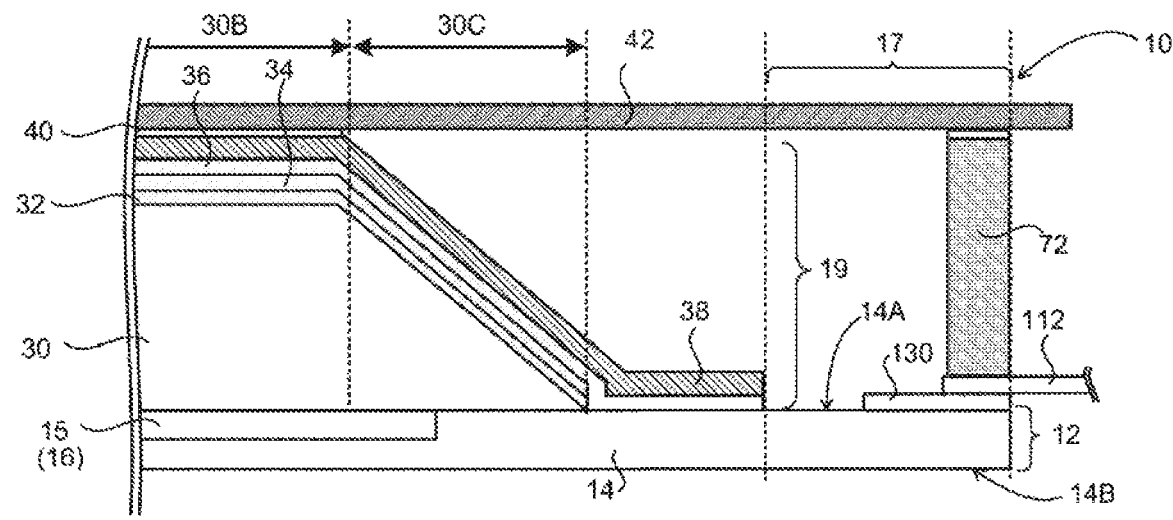
FIG. 27 is a cross-sectional view illustrating an example of configuration of a radiation detector of an exemplary embodiment of technology disclosed herein.

In the example illustrated in FIG. 27, the end portion of the elastic layer 42 is supported by the spacer 72. Namely, one end of the spacer 72 is connected to the cable 112 provided at the end portion of the sensor substrate 12, and the other end of the spacer 72 is connected to the end portion of the elastic layer 42. By using the spacer 72 to support the end portion of the elastic layer 42 that extends so as to form a space between itself and the sensor substrate 12, detachment of the elastic layer 42 can be suppressed. Moreover, the bending suppression effect from the elastic layer 42 can be caused to act as far as the vicinity of the end portion of the sensor substrate 12.

Figure 28:
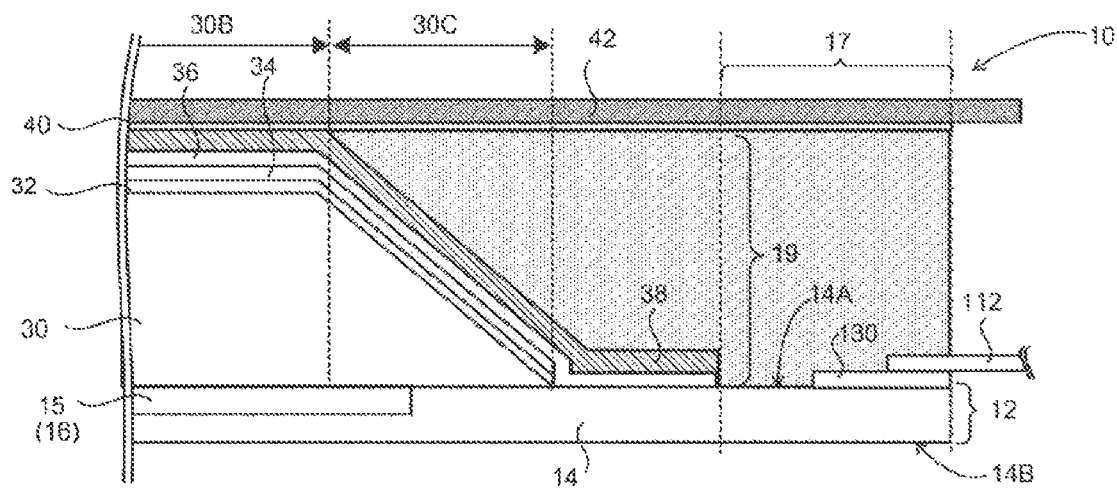
FIG. 28 is a cross-sectional view illustrating an example of configuration of a radiation detector of an exemplary embodiment of technology disclosed herein.

In the example illustrated in FIG. 28, the filler 70 is filled into the space formed between the conversion layer 30 (the protective layer 38) and the elastic layer 42, and between the sensor substrate 12 and the elastic layer 42. In the present exemplary embodiment, the connection portions between the cable 112 and the terminals 130 are covered by the filler 70. By filling the space formed between the conversion layer 30 (the protective layer 38) and the elastic layer 42 and between the sensor substrate 12 and the elastic layer 42 with the filler 70 in this manner, the elastic layer 42 can be better suppressed from detaching from the conversion layer 30 (the protective layer 38) than in the embodiment illustrated in FIG. 29. Furthermore, due to the conversion layer 30 having a structure fixed to the sensor substrate 12 by both the elastic layer 42 and the filler 70, the conversion layer 30 can be suppressed from detaching from the sensor substrate 12. Moreover, since the connection portions between the cable 112 and the terminals 130 are covered by the filler 70, detachment of the cable 112 can be suppressed.

Figure 29:
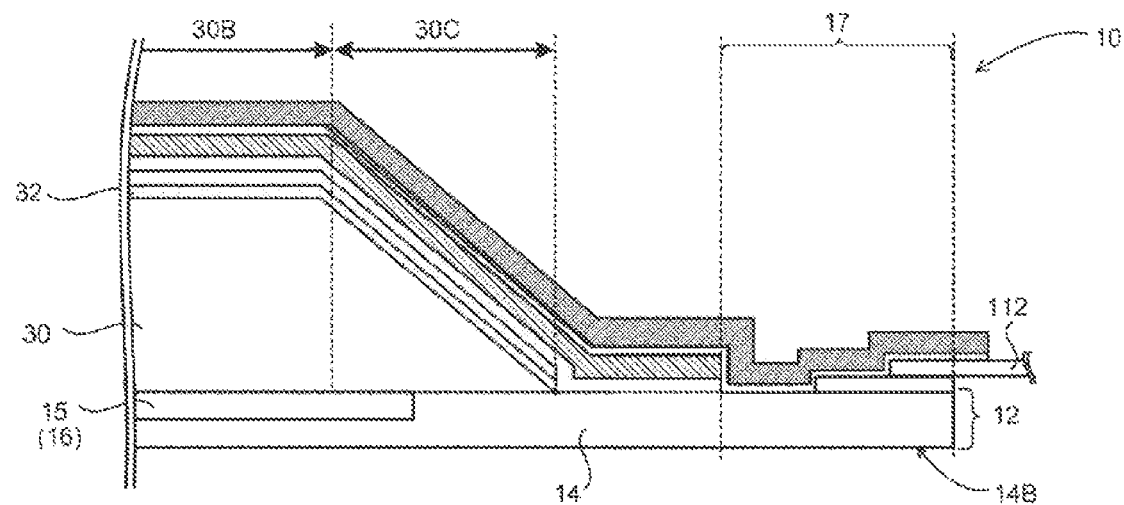
FIG. 29 is a cross-sectional view illustrating an example of configuration of a radiation detector of an exemplary embodiment of technology disclosed herein.

In the example illustrated in FIG. 29, the outer peripheral portion of the elastic layer 42 is angled so as to follow the slope of the peripheral edge portion 30C of the conversion layer 30. The outer peripheral portion of the elastic layer 42 also covers the portion where the bonding layer 36 and the protective layer 38 cover the sensor substrate 12, the portion on the substrate at the outer side thereof, and the connection portions between the cable 112 and the terminals 130. The portions of the elastic layer 42 extending over the sensor substrate 12 and over the cable 112 are respectively bonded to the sensor substrate 12 and the cable 112 through the bonding layer 40. By covering the connection portions between the cable 112 and the terminals 130 with the elastic layer 42, detachment of the cable 112 can be suppressed. Moreover, since the other end of the cable 112 is anticipated to be connected to a control board mounted with electronic components, there is a concern regarding comparatively large bending of the sensor substrate 12 at the connection portions between the cable 112 and the terminals 130. Since the connection portions between the cable 112 and the terminals 130 are covered by the elastic layer 42, such bending of the sensor substrate 12 at these portions can be suppressed.

Figure 30:
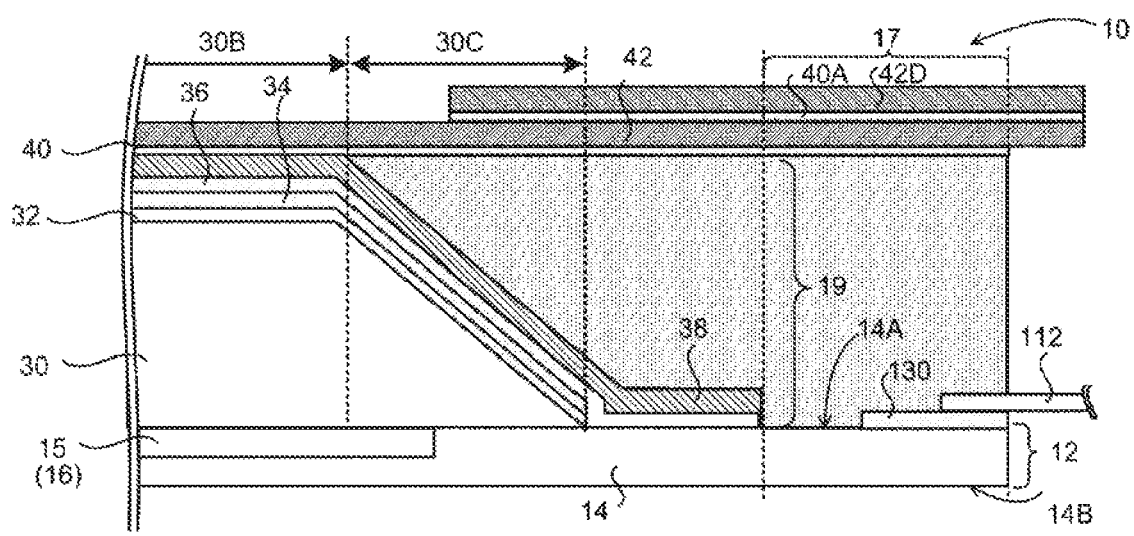
FIG. 30 is a cross-sectional view illustrating an example of configuration of a radiation detector of an exemplary embodiment of technology disclosed herein.

In the example illustrated in FIG. 30, the filler 70 is filled into the space formed between the conversion layer 30 (the protective layer 38) and the elastic layer 42 and between the sensor substrate 12 and the elastic layer 42. Moreover, the additional and separate elastic layer 42D is stacked on the front surface of the elastic layer 42 at the region corresponding to the end portion of the conversion layer 30, with the bonding layer 40A interposed therebetween. More specifically, the elastic layer 42D is provided in a region straddling the end portion (outer edge, edge) of the conversion layer 30. The elastic layer 42D may be configured from the same materials as the elastic layer 42. In the radiation detector 10, the amount of bending of the sensor substrate 12 is comparatively large at the end portion of the conversion layer 30. Forming a multi-layer structure with the elastic layers 42 and 42D at the region corresponding to the end portion of the conversion layer 30 enables the effect of suppressing bending of the sensor substrate 12 to be enhanced at the end portion of the conversion layer 30.

As described above, in processes to manufacture the radiation detector 10, the flexible sensor substrate 12 is affixed to the support body 50, for example a glass substrate. After stacking the conversion layer 30 on the sensor substrate 12, the support body 50 is separated from the sensor substrate 12. Bending occurs in the flexible sensor substrate 12 when this is performed, and so there is a concern that the pixels 16 formed on the sensor substrate 12 might be damaged thereby. By stacking the elastic layer 42 on the conversion layer 30 as in the embodiments illustrated in the examples of FIG. 18 to FIG. 30 prior to separating the support body 50 from the sensor substrate 12, the bending of the sensor substrate 12 that occurs during separation of the support body 50 from the sensor substrate 12 can be suppressed, enabling the risk of damage of the pixels 16 to be reduced.

Figure 31:
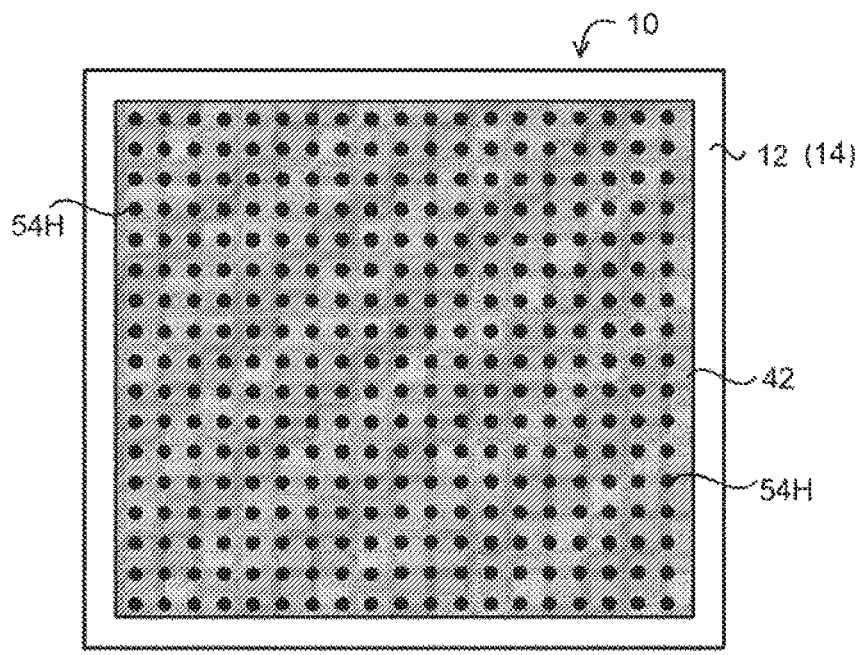
FIG. 31 is a cross-sectional view illustrating an example of configuration of a radiation detector of an exemplary embodiment of technology disclosed herein.

FIG. 31 is a plan view illustrating an example of a structure of the elastic layer 42. A main face of the elastic layer 42 may include plural through holes 42H. The size and pitch of the through holes 42H is prescribed so as to obtain the desired rigidity of the elastic layer 42.

Including the plural through holes 42H in the elastic layer 42 enables air introduced at the joining face of the elastic layer 42 to the conversion layer 30 to escape through the through holes 42H. This enables air bubbles to be suppressed from being generated at the joining face of the elastic layer 42 to the conversion layer 30.

There is a concern that air bubbles might be generated at the joining face of the elastic layer 42 to the conversion layer 30 if no mechanism is provided to allow air introduced at the joining face to escape. For example, were air bubbles generated at the joining face to expand due to heat during operation of the radiographic imaging device 1, there would be a drop in the cohesion between the elastic layer 42 and the conversion layer 30. This would lead to a concern that the bending suppression effect from the elastic layer 42 might not be sufficiently exhibited. By using the elastic layer 42 including the plural through holes 42H as illustrated in FIG. 31, the generation of air bubbles at the joining face of the elastic layer 42 to the conversion layer 30 can be suppressed as described above, enabling the cohesion between the elastic layer 42 and the conversion layer 30 to be maintained. This enables the bending suppression effect of the elastic layer 42 to be maintained.

Figure 32:
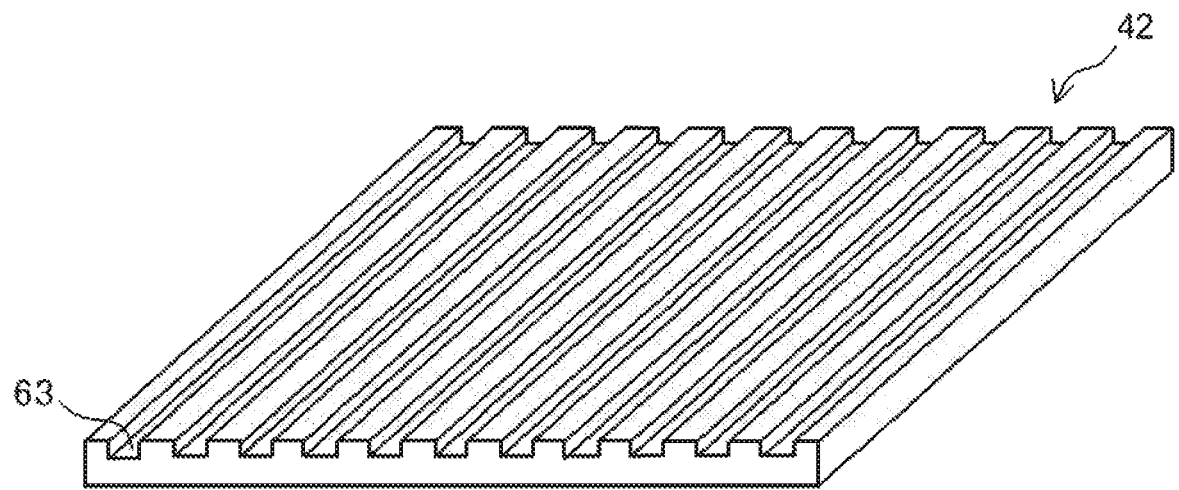
FIG. 32 is a cross-sectional view illustrating an example of configuration of a radiation detector of an exemplary embodiment of technology disclosed herein.
Figure 33:
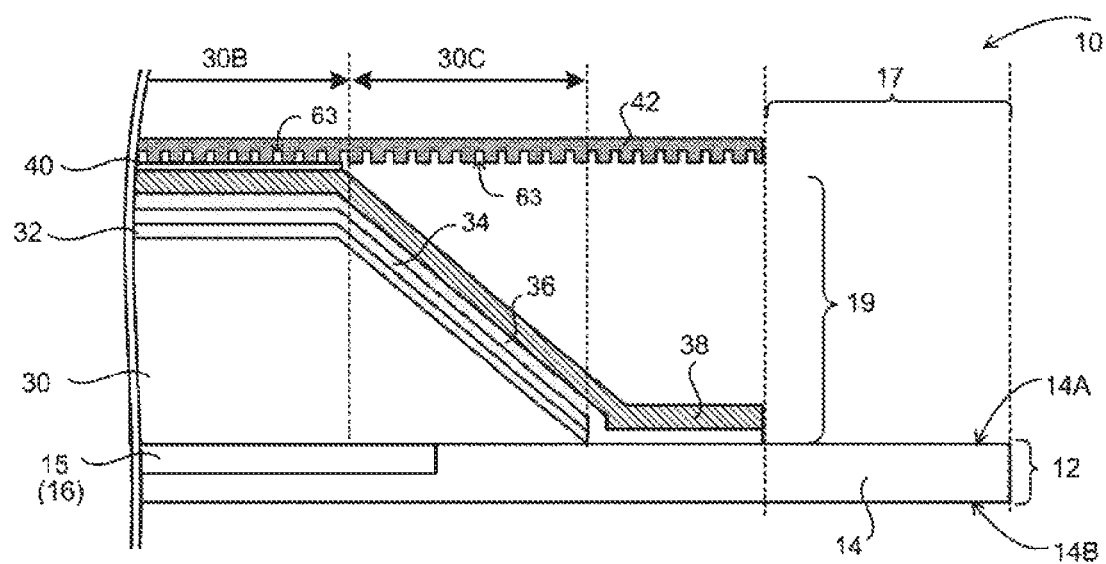
FIG. 33 is a cross-sectional view illustrating an example of configuration of a radiation detector of an exemplary embodiment of technology disclosed herein.

FIG. 32 is a perspective view illustrating another example of the structure of the elastic layer 42. In the example illustrated in FIG. 32, the elastic layer 42 includes an indented-and-protruding structure on the joining face to the conversion layer 30. The indented-and-protruding structure may be configured including plural grooves 63 arranged parallel to each other, as illustrated in FIG. 32. The face of the elastic layer 42 that includes the indented-and-protruding structure configured from the plural grooves 63 is, for example as illustrated in FIG. 33, joined to the conversion layer 30 that has been covered by the reflective layer 34. Due to the elastic layer 42 including the indented-and-protruding structure on the joining face to the conversion layer 30 in this manner, any air introduced to the joining portion of the elastic layer 42 and the conversion layer 30 is able to escape through the grooves 63. Similarly to in the embodiment illustrated in FIG. 35, this accordingly enables the generation of air bubbles at the joining face of the elastic layer 42 to the conversion layer 30 to be suppressed. This enables the cohesion between the elastic layer 42 and the conversion layer 30 to be maintained, and enables the bending suppression effect of the elastic layer 42 to be maintained.

Figure 34:
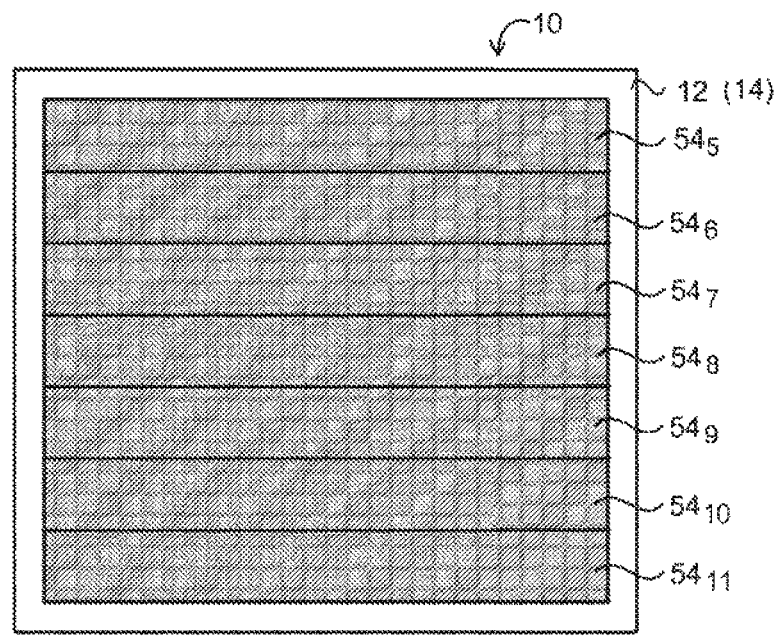
FIG. 34 is a cross-sectional view illustrating an example of configuration of a radiation detector of an exemplary embodiment of technology disclosed herein.
Figure 35:
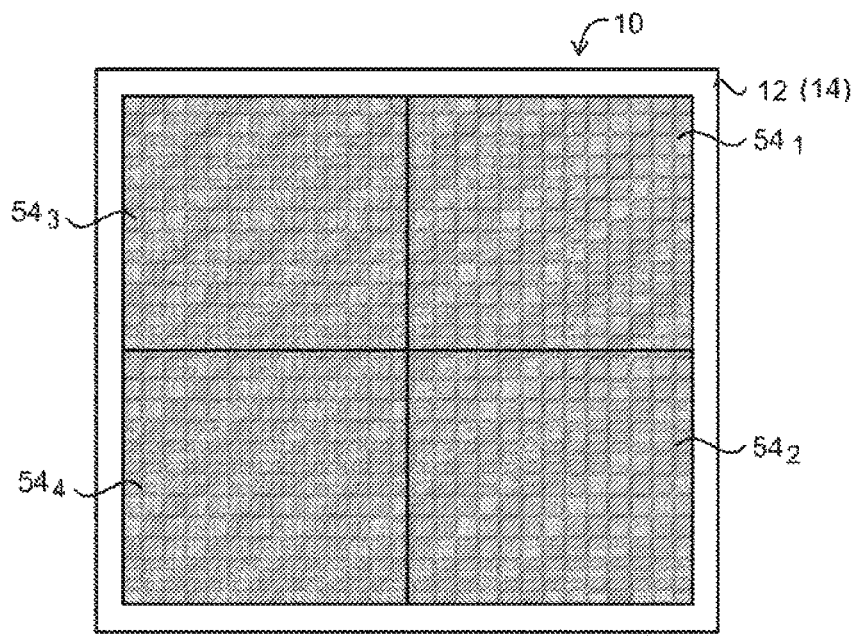
FIG. 35 is a plan view illustrating an example of a structure of a bending suppression member of an exemplary embodiment of technology disclosed herein.

FIG. 34 and FIG. 35 are plan views illustrating other examples of structures of the elastic layer 42. As illustrated in FIG. 34 and FIG. 35, the elastic layer 42 may be segmented into plural pieces 54. The elastic layer 42 may, as illustrated in FIG. 34, be segmented into plural pieces 54 ($54_5$ to $54_{11}$) arrayed in a single direction. Alternatively, the elastic layer 42 may, as illustrated in FIG. 35, be segmented into plural pieces 54 ($54_1$ to $49_4$) arrayed in both a longitudinal direction and a lateral direction.

Figure 38:
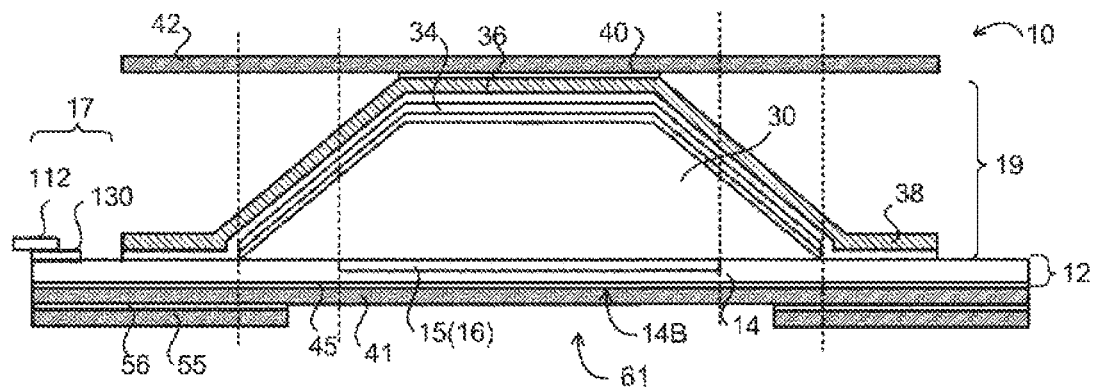
FIG. 38 is a plan view illustrating an example of a structure of a bending suppression member of an exemplary embodiment of technology disclosed herein.
Figure 39:
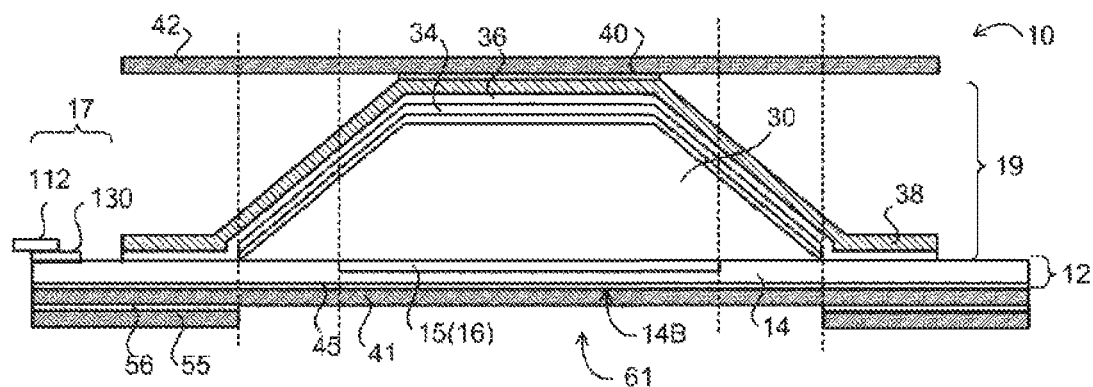
FIG. 39 is a plan view illustrating an example of a structure of a bending suppression member of an exemplary embodiment of technology disclosed herein.
Figure 40:
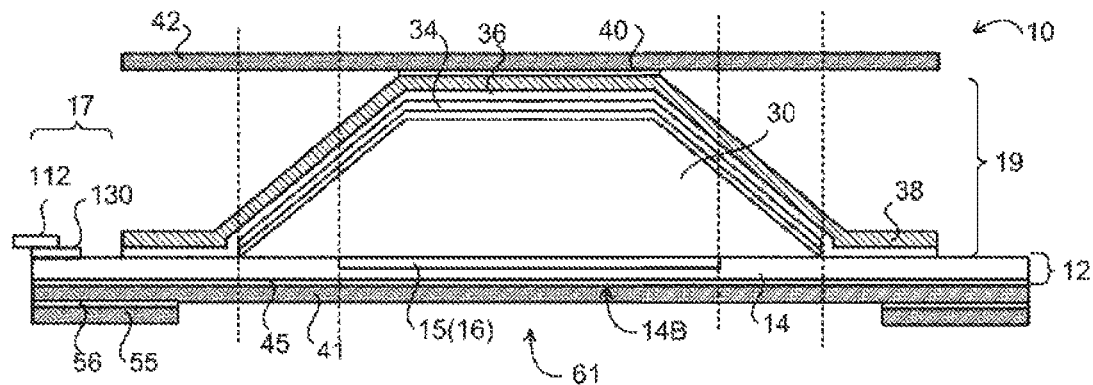
FIG. 40 is a cross-sectional view illustrating an example of configuration of a radiation detector of an exemplary embodiment of technology disclosed herein.

The greater the surface area of the elastic layer 42, the more readily air bubbles are generated at the joining face of the elastic layer 42 to the conversion layer 30. As illustrated in FIG. 38 and FIG. 39, segmenting the elastic layer 42 into the plural pieces 54 enables the generation of air bubbles at the joining face of the elastic layer 42 to the conversion layer 30 to be suppressed. This enables the cohesion between the elastic layer 42 and the conversion layer 30 to be maintained, and thereby enables the bending suppression effect of the elastic layer 42 to be maintained.

A reinforcement member 55 may be provided on the opposite side of the elastic member 41 to the side contacting the sensor substrate 12 (the second surface 14B). FIG. 36 to FIG. 40 are cross-sectional views respectively illustrating examples of embodiments of installation of the reinforcement member 55.

In the examples illustrated in FIG. 36 to FIG. 40, the reinforcement member 55 is stacked on the surface of the elastic member 41 on the opposite side to the surface on the sensor substrate 12 side, with a bonding layer 56 interposed therebetween. The reinforcement member 55 may be configured from the same materials as the elastic layer 42. In cases in which the radiation detector 10 employs an ISS approach, the reinforcement member 55 is preferably provided only at an outer peripheral portion of the sensor substrate 12 so as to keep the surface area of locations where the reinforcement member 55 and the pixel region 15 overlap each other as small as possible. Namely, the reinforcement member 55 may have a ring shape with an opening 61 at a location corresponding to the pixel region 15, as illustrated in FIG. 36 to FIG. 40. Forming a multi-layer structure with the elastic member 41 and the reinforcement member 55 at the outer peripheral portion of the sensor substrate 12 in this manner enables the rigidity of the outer peripheral portion of the sensor substrate 12 that is comparatively susceptible to bending to be reinforced.

In the examples illustrated in FIG. 36 to FIG. 40, the reinforcement member 55 is provided at a region straddling the end portion (outer edge, edge) of the conversion layer 30. In the radiation detector 10, the amount of bending of the sensor substrate 12 is comparatively large at the end portion of the conversion layer 30. Forming a multi-layer structure with the elastic member 41 and the reinforcement member 55 at the region corresponding to the end portion of the conversion layer 30 enables the effect of suppressing bending of the sensor substrate 12 to be enhanced at the end portion of the conversion layer 30.

Figure 36:
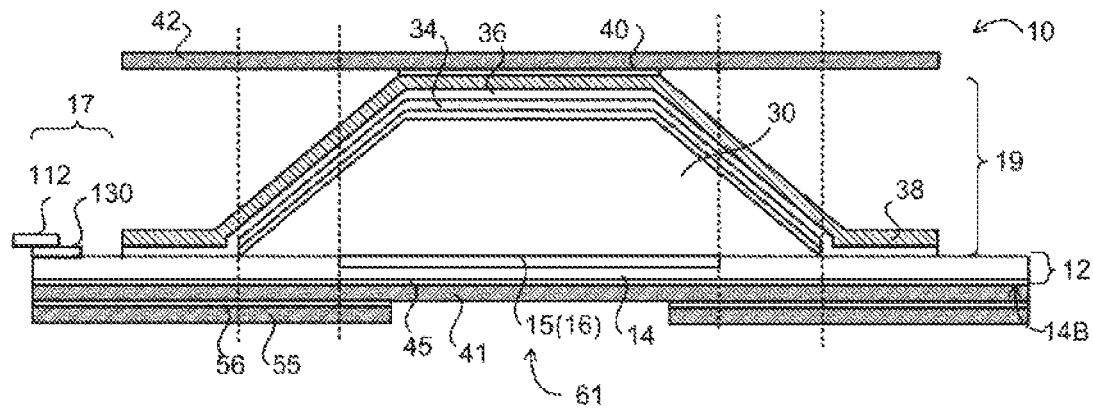
FIG. 36 is a perspective view illustrating an example of a structure of a bending suppression member of an exemplary embodiment of technology disclosed herein.

In cases in which an ISS approach is employed in the radiation detector 10, there is a concern that were a portion of the reinforcement member 55 to overlap with the pixel region 15 as illustrated in FIG. 36, this might have an impact on the images, depending on the substance employed in the reinforcement member 55. Thus, in cases in which a portion of the reinforcement member 55 overlaps with the pixel region 15, a plastic is preferably employed for the material of the reinforcement member 55.

Figure 37:
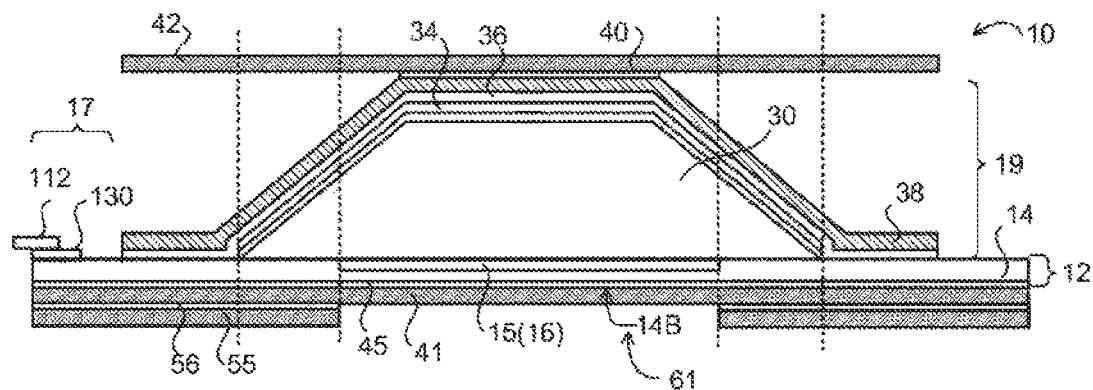
FIG. 37 is a cross-sectional view illustrating an example of configuration of a radiation detector of an exemplary embodiment of technology disclosed herein.

As illustrated in FIG. 37 and FIG. 38, an embodiment is most preferably adopted in which the reinforcement member 55 straddles the end portion (outer edge, edge) of the conversion layer 30 but does not overlap with the pixel region 15 (namely, an embodiment in which an edge of the opening 61 in the reinforcement member 55 is disposed at the outer side of the pixel region 15). In the example illustrated in FIG. 41, the position of the edge of the opening 61 in the reinforcement member 55 is substantially aligned with the position of the end portion of the pixel region 15. In the example illustrated in FIG. 42, the edge of the opening 61 in the reinforcement member 55 is disposed between the end portion of the pixel region 15 and the end portion of the conversion layer 30.

Moreover, the position of the edge of the opening 61 in the reinforcement member 55 may be disposed so as to be substantially aligned with the position of the end portion of the conversion layer 30 as illustrated in FIG. 39, or may be disposed so as to be further tower the outer side than the end portion of the conversion layer 30 as illustrated in FIG. 44. In such cases, there is no structure present where the reinforcement member 55 straddles the end portion (outer edge, edge) of the conversion layer 30, and so there might be a concern regarding a lessening of the effect of suppressing bending of the sensor substrate 12 at the end portion of the conversion layer 30. However, due to forming a stacked structure with the elastic member 41 and the reinforcement member 55 at the outer peripheral portion of the sensor substrate 12 where the connection portions between the cable 112 and the terminals 130 are present, the effect of suppressing bending of the sensor substrate 12 at the connection portions between the cable 112 and the terminals 130 is maintained.

In the radiation detectors 10 of the exemplary embodiments described above, explanation has been given regarding embodiments in which the size of the sensor substrate 12 (base member 14) and the size of the elastic member 41 are the same as each other. However, the size of the sensor substrate 12 and the size of the elastic member 41 may be different to each other.

For example, in cases in which the radiation detector 10 is applied to the radiographic imaging device 1, the radiation detector 10 may be employed fixed to the case 120 (see FIG. 11, etc.) or the like that houses the radiation detector 10. In such cases, as in the example illustrated in FIG. 41A, the elastic member 41 may be made larger than the sensor substrate 12 and provided with a flap or the like such that the radiation detector 10 can be fixed at the location of the flap or the like. For example, an embodiment may be configured in which holes are provided in a flap portion of the elastic member 41, and screws are passed through the holes to fix the elastic member 41 to the case 120 (see FIG. 6A, etc.)

Figure 41A:
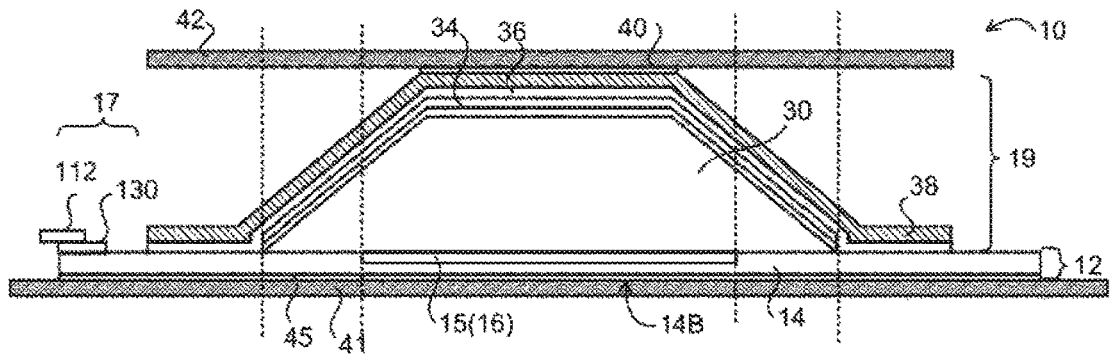
FIG. 41A is a cross-sectional view illustrating an example of configuration of a radiation detector of an exemplary embodiment of technology disclosed herein.
Figure 41B:
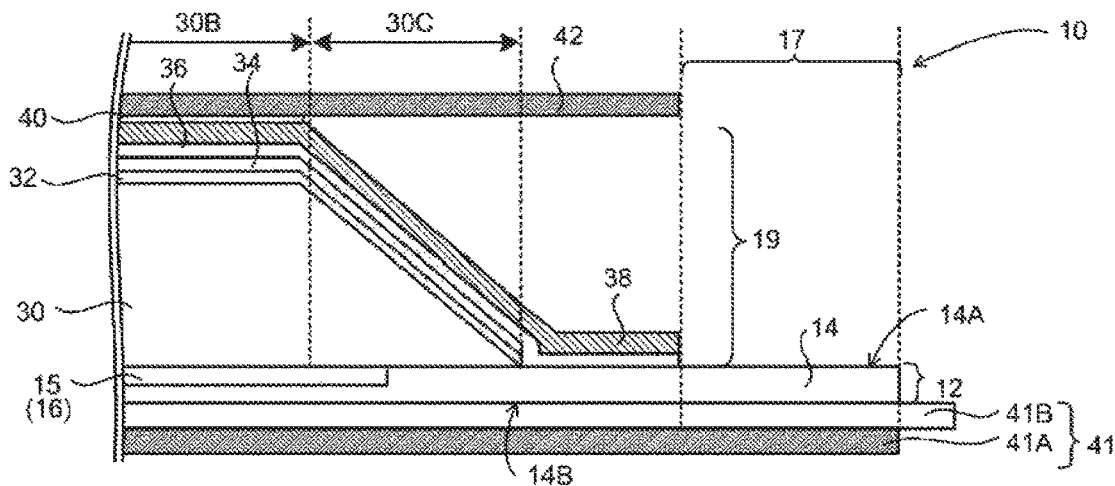
FIG. 41B is a cross-sectional view illustrating an example of configuration of a radiation detector of an exemplary embodiment of technology disclosed herein.

Note that embodiments in which the elastic member 41 is larger than the sensor substrate 12 are not limited to the embodiment illustrated in FIG. 41A. An embodiment may be configured in which the elastic member 41 is configured with plural stacked layers, with some of these layers being larger than the sensor substrate 12. For example, as illustrated in FIG. 41B, the elastic member 41 may be configured with a dual-layer structure including a first layer 41A of similar size to the sensor substrate 12 (the base member 14) and a second layer 41B that is larger than the sensor substrate 12. The first layer 41A is affixed to the second layer 41B using double-sided tape, an adhesion layer, or the like (not illustrated in the drawings). For example, the first layer 41A is preferably formed of similar materials to the elastic member 41 described above so as to possess similar characteristics to the elastic member 41. The second layer 41B is affixed to the second surface 14B of the base member 14 using double-sided tape, an adhesion layer, or the like (not illustrated in the drawings). For example, ALPET (registered trademark) may be applied as the second layer 41B. In cases in which the elastic member 41 is configured with plural layers, conversely to the embodiment illustrated in FIG. 41B, an embodiment may be configured in which the first layer 41A is affixed to the second surface 14B of the base member 14, as illustrated in FIG. 41C.

As described above, in cases in which the radiation detector 10 is fixed to the case 120 (see FIG. 6A, etc.) or the like using a flap or the like provided to the elastic member 41, such fixing may be performed in a state in which the flap portion is bent. The thinner the thickness thereof, the more easily the flap portion of the elastic member 41 will bend, enabling the flap portion alone to be bent without affecting the main body of the radiation detector 10. Accordingly, in cases in which the flap portion or the like is to be bent, an embodiment in which the elastic member 41 is configured of plural stacked layers with some of these layers being configured larger than the sensor substrate 12 as illustrated in the examples of FIG. 41B and FIG. 41C is preferable.

Figure 41C:
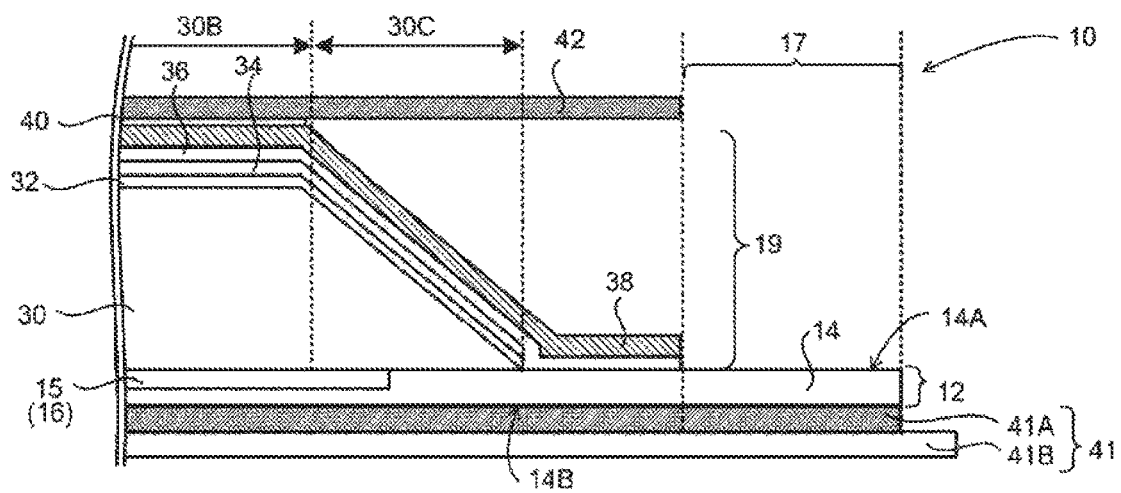
FIG. 41C is a cross-sectional view illustrating an example of configuration of a radiation detector of an exemplary embodiment of technology disclosed herein.
Figure 42:
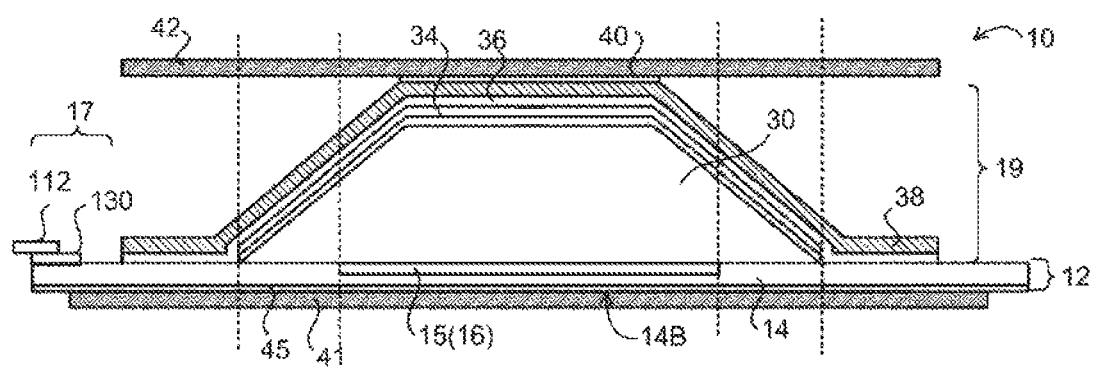
FIG. 42 is a cross-sectional view illustrating an example of configuration of a radiation detector of an exemplary embodiment of technology disclosed herein.

As in the example illustrated in FIG. 42, conversely to the radiation detectors 10 in FIG. 41A to FIG. 41C, the elastic member 41 may be smaller than the sensor substrate 12. Positioning an end portion of the sensor substrate 12 at the outer side of an end portion of the elastic member 41 facilitates checking of the position of the end portion of the sensor substrate 12 during assembly, for example when housing the radiation detector 10 inside the case 120 (see FIG. 7, etc.), thus enabling positioning precision to be improved. Note that there is no limitation to the embodiment illustrated in FIG. 42, since as long as at least a portion of the end portion of the sensor substrate 12 (the base member 14) is positioned at the outer side of the elastic member 41, similar preferable advantageous effects can be obtained.

The disclosures of Japanese Patent Application Nos. 2018-051690, 2018-219696, and 2019-022148 are incorporated in their entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

What is claimed is:
1. A radiation detector comprising:
a sensor substrate including a flexible base member and a layer provided on a first surface of the base member and formed with a plurality of pixels that accumulates electrical charge generated in response to light converted from radiation;
a conversion layer provided on the first surface side of the sensor substrate, the conversion layer converts radiation into the light;
a pad area provided at the first surface side of the sensor substrate in a predetermined range spanning from an outer edge portion toward a center of the sensor substrate, the pad area including pads to which cables are connected; and
an elastic layer provided on the opposite side of the conversion layer to a side provided with the sensor substrate, the elastic layer having a greater restoring force with respect to bending than the sensor substrate,
wherein the base member satisfies at least one selected from the following group of conditions:
having a heat shrinkage ratio in a machine direction at 400° C. and at a thickness of 25 µm of no greater than 0.5%, and
having a modulus of elasticity at 500° C. of no less than 1 GPa,
wherein the elastic layer has a bending elastic modulus of from 150 MPa to 2500 MPa, and
wherein the elastic layer projects parallel to the sensor substrate with the conversion layer sandwiched between, and does not project into a region corresponding to the pad area.

2. The radiation detector of claim 1, wherein a ratio of a coefficient of thermal expansion of the elastic layer with respect to a coefficient of thermal expansion of the conversion layer is from 0.5 to 4.

3. The radiation detector of claim 1, wherein the elastic layer has a coefficient of thermal expansion of from 30 ppm/K to 200 ppm/K.

4. The radiation detector of claim 1, wherein:
the sensor substrate further includes a terminal portion provided at an outer peripheral portion of the first surface of the base member, the terminal portion being connected to a cable for reading electrical charge from the pixels; and
an end portion of the elastic layer is positioned at an inner side of a region provided with the terminal portion.

5. The radiation detector of claim 4, wherein:
the conversion layer includes a peripheral edge portion having a slope that decreases in thickness on progression toward an outer side, and a central portion surrounded by the peripheral edge portion; and
the elastic layer covers at least the central portion.

6. The radiation detector of claim 4, wherein:
the conversion layer includes a peripheral edge portion having a slope that decreases in thickness on progression toward an outer side, and a central portion surrounded by the peripheral edge portion; and
the elastic layer covers the central portion and at least part of the peripheral edge portion.

7. The radiation detector of claim 4, wherein:
the conversion layer includes a peripheral edge portion having a slope that decreases in thickness on progression toward an outer side, and a central portion surrounded by the peripheral edge portion; and
an end portion of the elastic layer is provided to reach at least from a region covering the central portion to a region corresponding to an outer periphery of the peripheral edge portion.

8. The radiation detector of claim 1, wherein:
the sensor substrate further includes a terminal portion provided at an outer peripheral portion of the first surface of the base member, the terminal portion being connected to a cable for reading electrical charge from the pixels; and
the elastic layer is provided so as to reach a region opposing part or all of a region provided with the terminal portion.

9. The radiation detector of claim 1, wherein the elastic layer is provided in a wider region than a region of the sensor substrate provided with the conversion layer.

10. The radiation detector of claim 1, wherein an end portion of the elastic layer projects further toward an outer side than an end portion of the sensor substrate.

11. The radiation detector of claim 1, wherein the elastic layer is provided so as to reach a region outside the conversion layer, and the elastic layer further includes a support portion that supports between an end portion of the elastic layer and the sensor substrate.

12. The radiation detector of claim 1, further comprising a filler that fills a space between the sensor substrate and the elastic layer where the conversion layer is not present.

13. The radiation detector of claim 12, wherein the filler contacts the sensor substrate and the elastic layer.

14. The radiation detector of claim 1, further comprising a cohesion layer provided between the sensor substrate and the conversion layer.

15. The radiation detector of claim 1, further comprising an elastic member provided on a second surface side of the base member on the opposite side to the first surface, the elastic member having a greater restoring force with respect to bending than the sensor substrate.

16. The radiation detector of claim 15, wherein at least part of the elastic layer and at least part of the elastic member oppose each other across the sensor substrate and the conversion layer.

17. The radiation detector of claim 15, wherein a ratio of a coefficient of thermal expansion of the elastic member with respect to a coefficient of thermal expansion of the conversion layer is from 0.5 to 4.

18. The radiation detector of claim 15, wherein the elastic member has a coefficient of thermal expansion of from 30 ppm/K to 200 ppm/K.

19. A radiographic imaging device comprising:
the radiation detector of claim 1;
a control section that output a control signal in order to read the electrical charges accumulated in the plurality of pixels;
a drive section that output a drive signal in order to read the electrical charges from the plurality of pixels in response to the control signal; and
a signal processing section that generates and output image data in response to an input electrical signal in a case in which input with the electrical signal according to the electrical charges read from the plurality of pixels.

20. The radiographic imaging device of claim 19, wherein the control section and the radiation detector are provided arranged in a direction intersecting a stacking direction of the base member, the layer formed with the plurality of pixels, and the conversion layer in the radiation detector.

21. The radiographic imaging device of claim 19, further comprising a case that includes an irradiated face for irradiation with radiation, the case houses the radiation detector in a state in which out of the sensor substrate and the conversion layer of the radiation detector it is the sensor substrate that opposes the irradiated face.

22. The radiation detector of claim 1, further comprising an elastic member provided on a second surface side of the base member at an opposite side from the first surface, the elastic member being provided from the outer edge portion of the second surface side of the base member to a region at which the pad area is provided and to a part of a region at which the conversion layer is provided.

* * * * *